United States Patent
Shimamoto et al.

(10) Patent No.: US 10,263,285 B2
(45) Date of Patent: Apr. 16, 2019

(54) NONAQUEOUS ELECTROLYTE, CAPACITOR DEVICE USING SAME, AND CARBOXYLIC ACID ESTER COMPOUND USED IN SAME

(71) Applicant: UBE INDUSTRIES, LTD., Ube-shi (JP)

(72) Inventors: Kei Shimamoto, Shimonoseki (JP); Koji Abe, Ube (JP); Shoji Shikita, Ube (JP); Kazuhiro Miyoshi, Ube (JP)

(73) Assignee: UBE INDUSTRIES, LTD., Ube-shi (JP)

(*) Notice: Subject to any disclaimer, the term of this patent is extended or adjusted under 35 U.S.C. 154(b) by 330 days.

(21) Appl. No.: 15/103,220

(22) PCT Filed: Dec. 17, 2014

(86) PCT No.: PCT/JP2014/083415
§ 371 (c)(1),
(2) Date: Jun. 9, 2016

(87) PCT Pub. No.: WO2015/093532
PCT Pub. Date: Jun. 25, 2015

(65) Prior Publication Data
US 2018/0166746 A1    Jun. 14, 2018

(30) Foreign Application Priority Data

Dec. 19, 2013 (JP) ................................ 2013-262928
May 23, 2014 (JP) ................................ 2014-107584
Sep. 4, 2014 (JP) ................................ 2014-179897

(51) Int. Cl.
*H01M 10/0568* (2010.01)
*H01M 10/0567* (2010.01)
(Continued)

(52) U.S. Cl.
CPC ...... *H01M 10/0568* (2013.01); *C07D 317/36* (2013.01); *C07D 317/42* (2013.01); *C07D 327/00* (2013.01); *C07D 327/10* (2013.01); *H01G 11/62* (2013.01); *H01G 11/64* (2013.01); *H01M 10/052* (2013.01);
(Continued)

(58) Field of Classification Search
CPC combination set(s) only.
See application file for complete search history.

(56) References Cited

U.S. PATENT DOCUMENTS

2010/0092872 A1    4/2010 Abe et al.
2010/0119955 A1    5/2010 Abe et al.
(Continued)

FOREIGN PATENT DOCUMENTS

JP      7-285960 A       10/1995
JP      07285960 A   *   10/1995
(Continued)

OTHER PUBLICATIONS

International Search Report dated Mar. 24, 2015 in PCT/JP2014/083415 filed Dec. 17, 2014.
(Continued)

*Primary Examiner* — Carlos Barcena
(74) *Attorney, Agent, or Firm* — Oblon, McClelland, Maier & Neustadt, L.L.P.

(57) ABSTRACT

The present invention provides a nonaqueous electrolytic solution capable of improving electrochemical characteristics in the case of using an energy storage device at a high temperature and at a high voltage and further capable of inhibiting the gas generation while maintaining a capacity retention rate after storage at a high temperature and at a high voltage and also provides an energy storage device using the same. Disclosed is a nonaqueous electrolytic solution having an electrolyte salt dissolved in a nonaqueous solvent, the nonaqueous electrolytic solution containing a carboxylic acid ester compound represented by the following general formula (I).

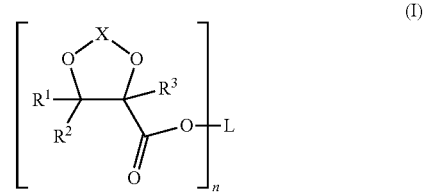

(I)

In the formula, each of $R^1$ and $R^2$ independently represents a hydrogen atom, a —C(=O)—$OR^4$ group, or the like, and $R^1$ and $R^2$ may be bonded to each other to form a ring structure. $R^3$ represents a hydrogen atom or the like, and n represents an integer of 1 to 3. When n is 1, then L and $R^4$ represent an alkyl group having 1 to 6 carbon atoms or the like; and when n is 2 or 3, then L represents an n-valent connecting group, X represents a —C(=O)— group, an —S(=O)— group, an —S(=O)$_2$— group, an —S(=O)$_2$—$R^5$—S(=O)$_2$— group or a $CR^6R^7$ group, $R^5$ represents an alkylene group having 1 to 4 carbon atoms, and each of $R^6$ and $R^7$ represents a hydrogen atom or an alkyl group having 1 to 6 carbon atoms.

9 Claims, No Drawings

(51) Int. Cl.
| | |
|---|---|
| H01M 10/052 | (2010.01) |
| H01G 11/62 | (2013.01) |
| H01G 11/64 | (2013.01) |
| C07D 317/36 | (2006.01) |
| C07D 317/42 | (2006.01) |
| H01M 10/42 | (2006.01) |
| C07D 327/00 | (2006.01) |
| C07D 327/10 | (2006.01) |

(52) U.S. Cl.
CPC ... *H01M 10/0567* (2013.01); *H01M 10/4235* (2013.01); *H01M 2300/0025* (2013.01); *Y02E 60/13* (2013.01); *Y02T 10/7011* (2013.01); *Y02T 10/7022* (2013.01)

(56) References Cited

U.S. PATENT DOCUMENTS

| | | |
|---|---|---|
| 2012/0088160 A1 | 4/2012 | Zhang et al. |
| 2013/0004862 A1 | 1/2013 | Miyoshi et al. |
| 2013/0216919 A1 | 8/2013 | Tokuda et al. |
| 2014/0154587 A1 | 6/2014 | Abe et al. |
| 2014/0356733 A1 | 12/2014 | Khasanov et al. |

FOREIGN PATENT DOCUMENTS

| | | |
|---|---|---|
| JP | 10-189042 A | 7/1998 |
| JP | 11-121032 A | 4/1999 |
| JP | 2000-40526 A | 2/2000 |
| JP | 2004-281368 A | 10/2004 |
| JP | 3586881 B2 | 11/2004 |
| JP | 2006-294414 A | 10/2006 |
| JP | 2012-64473 A | 3/2012 |
| JP | 2013-89390 A1 | 5/2013 |
| JP | 2014-72050 A | 4/2014 |
| WO | 2008/093837 A1 | 8/2008 |
| WO | 2011/122449 A1 | 10/2011 |
| WO | 2013/024748 A1 | 2/2013 |
| WO | 2013/099735 A1 | 7/2013 |

OTHER PUBLICATIONS

Extended European Search Report dated Jun. 20, 2017 in Patent Application No. 14871267.2.

Yang Yang, et al., "Total Synthesis of (−)-Jiadifenin", Natural Product Synthesis, Angewandte Chemie International Edition, XP055380226, vol. 51, No. 39, Aug. 24, 2012, pp. 9825-9828.

* cited by examiner

NONAQUEOUS ELECTROLYTE, CAPACITOR DEVICE USING SAME, AND CARBOXYLIC ACID ESTER COMPOUND USED IN SAME

TECHNICAL FIELD

The present invention relates to a nonaqueous electrolytic solution capable of improving electrochemical characteristics in using an energy storage device at a high voltage, an energy storage device using the same, and a carboxylic acid ester compound to be used for the same.

BACKGROUND ART

An energy storage device, especially a lithium secondary battery, has been widely used recently for a power source of a small-sized electronic device, such as a mobile telephone, a notebook personal computer, etc., and a power source for an electric vehicle or electric power storage. With respect to a thin electronic device, such as a tablet device, an ultrabook, etc., a laminate-type battery or a prismatic battery using a laminate film, such as an aluminum laminate film, etc., for an outer packaging member thereof is frequently used. In such a battery, the outer packaging member is thin, and therefore, there is involved such a problem that the battery is easily deformed even by a bit of expansion of the outer packaging member and the deformation very likely influences the electronic device.

A lithium secondary battery is mainly constituted of a positive electrode and a negative electrode, each containing a material capable of absorbing and releasing lithium, and a nonaqueous electrolytic solution including a lithium salt and a nonaqueous solvent; and a carbonate, such as ethylene carbonate (EC), propylene carbonate (PC), etc., is used as the nonaqueous solvent.

In addition, a lithium metal, a metal compound capable of absorbing and releasing lithium (e.g., a metal elemental substance, a metal oxide, an alloy with lithium, etc.), and a carbon material are known as the negative electrode of the lithium secondary battery. In particular, a nonaqueous electrolytic solution secondary battery using, as the carbon material, a carbon material capable of absorbing and releasing lithium, for example, coke or graphite (e.g., artificial graphite or natural graphite), etc., is widely put into practical use.

Since the aforementioned negative electrode material stores and releases lithium and an electron at an extremely electronegative potential equal to the lithium metal, it has a possibility that a lot of solvents are subjected to reductive decomposition, and a part of the solvent in the electrolytic solution is reductively decomposed on the negative electrode regardless of the kind of the negative electrode material, so that there were involved such problems that the movement of a lithium ion is disturbed due to deposition of decomposed products, generation of a gas, or expansion of the electrode, thereby worsening battery characteristics, such as cycle properties, etc., especially in the case of using the battery at a high temperature and at a high voltage; and that the battery is deformed due to expansion of the electrode. Furthermore, it is known that a lithium secondary battery using a lithium metal or an alloy thereof, a metal elemental substance, such as tin, silicon, etc., or a metal oxide thereof as the negative electrode material may have a high initial battery capacity, but the battery capacity and the battery performance thereof, such as cycle properties, may be largely worsened because the micronized powdering of the material may be promoted during cycles, which brings about accelerated reductive decomposition of the nonaqueous solvent, as compared with the negative electrode formed of a carbon material, and the battery may be deformed due to expansion of the electrode.

Meanwhile, since a material capable of absorbing and releasing lithium, which is used as a positive electrode material, such as $LiCoO_2$, $LiMn_2O_4$, $LiNiO_2$, $LiFePO_4$, etc., stores and releases lithium and an electron at an electropositive voltage of 3.5 V or more on the lithium basis, it has a possibility that a lot of solvents are subjected to oxidative decomposition especially in the case of using the battery at a high temperature and at a high voltage, and a part of the solvent in the electrolytic solution is oxidatively decomposed on the positive electrode regardless of the kind of the positive electrode material, so that there were involved such problems that the resistance is increased due to deposition of decomposed products; and that a gas is generated due to decomposition of the solvent, thereby expanding the battery.

Under such a situation, in electronic devices having a lithium secondary battery mounted therein, the electric power consumption increases, and the capacity increases steadily. The electrolytic solution is in the environment where the decomposition is apt to take place more and more due to an increase of temperature of the battery by the heat generation from the electronic device, an increase of voltage of charging setting voltage of the battery, and the like. Thus, there was involved such a problem that the battery becomes unable to be used due to expansion of the battery caused by the gas generation, actuation of a safety mechanism to cut off the current, etc., or the like.

Irrespective of the foregoing situation, the multifunctionality of electronic devices on which lithium secondary batteries are mounted is more and more advanced, and the electric power consumption tends to increase. The capacity of the lithium secondary battery is thus being much increased, and because of an increase of a density of the battery, a reduction of a useless space capacity within the battery, and so on, a volume occupied by the nonaqueous electrolytic solution in the battery is becoming small. In consequence, it is the present situation that in the case of using the battery at a high temperature and at a high voltage, the battery performance is apt to be worsened by decomposition of a bit of the nonaqueous electrolytic solution.

PTL 1 discloses dihydro-furo[3,4-d]-1,3-dioxole-2,4,6-trione as one of bicyclo compounds and suggests that when added to an electrolytic solution, the electrochemical characteristics of the battery, especially the cycle capacity retention rate at 55° C., is improved.

PTL 2 discloses diethyl 2-oxo-1,3-dioxolane-4,5-dicarboxylate having tetraethylammonium tetrafluoroborate dissolved therein as an electrolytic solution.

PTL 3 suggests that when an electrolytic solution containing methacryloxymethyl ethylene carbonate is used, even in the case of using high-crystalline carbon for a negative electrode, the reductive decomposition of the solvent is inhibited, and the charging and discharging efficiency is improved.

PTL 4 proposes a nonaqueous electrolytic solution containing a cyclic sulfuric acid ester, such as an ethylene glycol sulfuric acid ester, etc., and describes that the decomposition and deterioration of the electrolytic solution on the electrode surface are inhibited.

PTL 5 proposes a nonaqueous electrolytic solution containing ethylene sulfite and vinylene carbonate and describes that the 25° C. cycle characteristics are improved.

PTL 6 proposes a nonaqueous electrolytic solution containing a cyclic ether compound, such as 1,3-dioxane, 1,3-dioxolane, etc., and describes that a reaction of a positive electrode with the electrolytic solution at a high temperature is inhibited, so that the safety is improved.

PTL 7 proposes a nonaqueous electrolytic solution containing 1,5,2,4-dioxadithiepane 2,2,4,4-tetraoxide and suggests that the cycle characteristics and storage characteristics are improved.

PTL 1: US 2012/0088160A
PTL 2: JP-A 7-285960
PTL 3: JP-A 2000-40526
PTL 4: JP-A 10-189042
PTL 5: JP-A 11-121032
PTL 6: JP-A 2014-72050
PTL 7: JP-A 2004-281368

DISCLOSURE OF INVENTION

Technical Problem

Problems to be solved by the present invention are to provide a nonaqueous electrolytic solution capable of improving electrochemical characteristics in the case of using an energy storage device at a high temperature and at a high voltage and further capable of inhibiting the gas generation as well as improving a capacity retention rate after storage at a high voltage and at a high temperature, and also to provide an energy storage device using the same and a carboxylic acid ester compound to be used for the same.

Solution to Problem

The present inventors made extensive and intensive investigations regarding the performance of the nonaqueous electrolytic solutions of the aforementioned conventional technologies. As a result, according to the non aqueous electrolyte secondary batteries of PTLs 1 and 3, in fact, the effect could not be substantially exhibited against the problem of inhibiting the gas generation following charging and discharging in the case of using an energy storage device at a high temperature and at a high voltage.

According to the nonaqueous electrolyte secondary batteries of PTLs 4 and 5, in fact, the effect could not be substantially exhibited against the problem of inhibiting the gas generation following charging and discharging in the case of using an energy storage device at a high temperature and at a high voltage. In addition, according to the cyclic ether compound described in PTL 6, though it was perceived to make the gas generation gentle, its effect was insufficient.

Even according to the nonaqueous electrolyte secondary battery of PTL 7, in fact, the effect could not be substantially exhibited against the problem of inhibiting the gas generation following charging and discharging in the case of using an energy storage device at a high temperature and at a high voltage.

Then, in order to solve the foregoing problems, the present inventors made extensive and intensive investigations. As a result, it has been found that by adding a specified carboxylic acid ester compound, the capacity retention rate after storage in the case of using an energy storage device at a high temperature and at a high voltage can be improved, and also, the gas generation can be inhibited, leading to accomplishment of the present invention.

Specifically, the present invention provides the following (1) to (4).

(1) A nonaqueous electrolytic solution having an electrolyte salt dissolved in a nonaqueous solvent, the nonaqueous electrolytic solution containing a carboxylic acid ester compound represented by the following general formula (I).

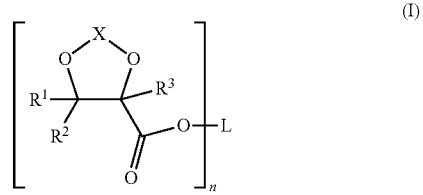

In the formula, each of $R^1$ and $R^2$ independently represents a hydrogen atom, a halogen atom, an alkyl group having 1 to 6 carbon atoms, a cycloalkyl group having 3 to 6 carbon atoms, an alkenyl group having 2 to 6 carbon atoms, an alkynyl group having 3 to 6 carbon atoms, an aralkyl group having 7 to 13 carbon atoms, an aryl group having 6 to 12 carbon atoms, or a —C(=O)—OR$^4$ group, and when $R^1$ and $R^2$ are each an alkyl group, then $R^1$ and $R^2$ may be bonded to each other to form a ring structure. $R^3$ represents a hydrogen atom, a halogen atom, or an alkyl group having 1 to 6 carbon atoms, and n represents an integer of 1 to 3.

When n is 1, then L and $R^4$ may be the same as or different from each other and represent an alkyl group having 1 to 6 carbon atoms, a cycloalkyl group having 3 to 6 carbon atoms, an alkenyl group having 2 to 6 carbon atoms, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, or an aryl group having 6 to 12 carbon atoms, and when n is 2 or 3, then L represents an n-valent connecting group constituted of a carbon atom and a hydrogen atom, which may contain an ether bond, a thioether bond, or an $SO_2$ bond, and $R^4$ is the same as described above.

X represents a —C(=O)— group, an —S(=O)— group, an —S(=O)$_2$— group, an —S(=O)$_2$—R$^5$—S(=O)$_2$— group or a CR$^6$R$^7$ group, R$^5$ represents an alkylene group having 1 to 4 carbon atoms, in which at least one hydrogen atom may be substituted with a halogen group or an alkyl group having 1 to 4 carbon atoms, and each of R$^6$ and R$^7$ independently represents a hydrogen atom or an alkyl group having 1 to 6 carbon atoms, in which at least one hydrogen atom may be substituted with a halogen atom.

At least one hydrogen atom of the alkyl group having 1 to 6 carbon atoms, the cycloalkyl group having 3 to 6 carbon atoms, the alkenyl group having 2 to 6 carbon atoms, the alkynyl group having 3 to 6 carbon atoms, the alkoxyalkyl group having 2 to 6 carbon atoms, the cyanoalkyl group having 2 to 6 carbon atoms, the aralkyl group having 7 to 13 carbon atoms, or the aryl group having 6 to 12 carbon atoms as $R^1$, $R^2$, $R^4$, or L, may be substituted with a halogen atom.

(2) An energy storage device including a positive electrode, a negative electrode, and a nonaqueous electrolytic solution having an electrolyte salt dissolved in a nonaqueous solvent, the nonaqueous electrolytic solution being the nonaqueous electrolytic solution as set forth above in (1).

(3) A carboxylic acid ester compound represented by the following general formula (II).

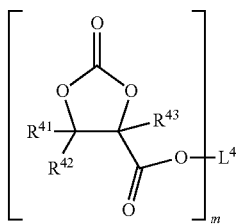

In the formula, each of $R^{41}$ and $R^{42}$ independently represents a hydrogen atom, a halogen atom, an alkyl group having 1 to 6 carbon atoms, in which at least one hydrogen atom may be substituted with a halogen atom, a cycloalkyl group having 3 to 6 carbon atoms, an alkenyl group having 2 to 6 carbon atoms, an alkynyl group having 3 to 6 carbon atoms, an aralkyl group having 7 to 13 carbon atoms, in which at least one hydrogen atom may be substituted with a halogen atom, an aryl group having 6 to 12 carbon atoms, in which at least one hydrogen atom may be substituted with a halogen atom, or a —C(=O)—$OR^{44}$ group, and when $R^{41}$ and $R^{42}$ are each an alkyl group, then $R^{41}$ and $R^{42}$ may be bonded to each other to form a ring structure. $R^{43}$ represents a hydrogen atom, a halogen atom, or an alkyl group having 1 to 6 carbon atoms, and m represents 1 or 2.

When m is 1, then $L^4$ and $R^{44}$ may be the same as or different from each other and represent a halogenated alkyl group having 1 to 6 carbon atoms, in which at least one hydrogen atom is substituted with a halogen atom, a halogenated cycloalkyl group having 3 to 6 carbon atoms, in which at least one hydrogen atom is substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 3 to 6 carbon atoms, a cyanoalkyl group having 2 to 6 carbon atoms, a halogenated aralkyl group having 7 to 13 carbon atoms, in which at least one hydrogen atom is substituted with a halogen atom, or a halogenated aryl group having 6 to 12 carbon atoms, in which at least one hydrogen atom is substituted with a halogen atom, and when in is 2, then $L^4$ represents an alkylene group having 2 to 6 carbon atoms, in which at least one hydrogen atom is substituted with a halogen atom, an alkenylene group having 4 to 8 carbon atoms, or an alkynylene group having 4 to 8 carbon atoms and $R^{44}$ is the same as described above, provided that when m is 1, then $L^4$ is not a 3-methyl-2-buten-1-yl group.

(4) A carboxylic acid ester compound represented by the following general formula (III).

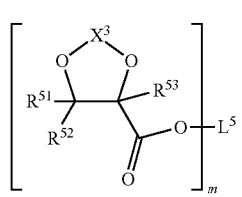

In the formula, each of $R^{51}$ and $R^{52}$ independently represents a hydrogen atom, a halogen atom, an alkyl group having 1 to 6 carbon atoms, a cycloalkyl group having 3 to 6 carbon atoms, an alkenyl group having 2 to 6 carbon atoms, an alkynyl group having 3 to 6 carbon atoms, an aralkyl group having 7 to 13 carbon atoms, an aryl group having 6 to 12 carbon atoms, or a —C(=O)—$OR^{54}$ group, and when $R^{51}$ and $R^{52}$ are each an alkyl group, then $R^{51}$ and $R^{52}$ may be bonded to each other to form a ring structure. $R^{53}$ represents a hydrogen atom, a halogen atom, or an alkyl group having 1 to 6 carbon atoms, and m represents 1 or 2.

When m is 1, then $L^5$ and $R^{54}$ may be the same as or different from each other and represent an alkyl group having 1 to 6 carbon atoms, a cycloalkyl group having 3 to 6 carbon atoms, an alkenyl group having 2 to 6 carbon atoms, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, or an aryl group having 6 to 12 carbon atoms, and when m is 2, then $L^5$ represents an alkylene group having 2 to 8 carbon atoms, an alkenylene group having 4 to 8 carbon atoms, or an alkynylene group having 4 to 8 carbon atoms, at least one hydrogen atom of $L^5$ may be substituted with a halogen atom, and $R^{54}$ is the same as described above.

$X^3$ represents an —S(=O)$_2$—$R^{55}$—S(=O)$_2$— group, and $R^{55}$ represents an alkylene group having 1 to 4 carbon atoms, in which at least one hydrogen atom may be substituted with a halogen atom or an alkyl group having 1 to 4 carbon atoms.

At least one hydrogen atom of the alkyl group having 1 to 6 carbon atoms, the cycloalkyl group having 3 to 6 carbon atoms, the alkenyl group having 2 to 6 carbon atoms, the alkynyl group having 3 to 6 carbon atoms, the alkoxyalkyl group having 2 to 6 carbon atoms, the cyanoalkyl group having 2 to 6 carbon atoms, the aralkyl group having 7 to 13 carbon atoms, or the aryl group having 6 to 12 carbon atoms as $R^{51}$, $R^{52}$, $R^{54}$, or $L^5$, may be substituted with a halogen atom.

Advantageous Effects of Invention

According to the present invention, it is possible to provide a nonaqueous electrolytic solution capable of not only improving a capacity retention rate after storage but also inhibiting the gas generation in the case of using an energy storage device at a high temperature and at a high voltage, and also to provide an energy storage device, such as a lithium battery, etc., using the same and a carboxylic acid ester compound to be used for the same.

DESCRIPTION OF EMBODIMENTS

The nonaqueous electrolytic solution of the present invention is concerned with a nonaqueous electrolytic solution having an electrolyte salt dissolved in a nonaqueous solvent, the nonaqueous electrolytic solution containing a carboxylic acid ester compound represented by the following general formula (I).

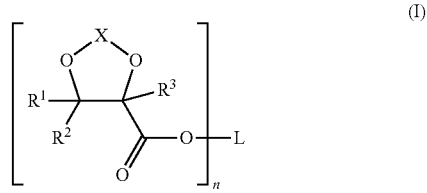

In the formula, $R^1$, $R^2$, $R^3$, X, L, and n are the same as described above.

In the nonaqueous electrolytic solution of the present invention, a content of the carboxylic acid ester compound represented by the foregoing general formula (I) is preferably 0.001% by mass or more, more preferably 0.01% by mass or more, and still more preferably 0.3% by mass or more, and preferably 30% by mass or less, more preferably 20% by mass or less, still more preferably 10% by mass or less, and yet still more preferably 5% by mass or less from the viewpoint of forming an appropriate surface film on an electrode, thereby enhancing an improving effect of storage characteristics in the case of using a battery at a high temperature and at a high voltage.

The nonaqueous electrolytic solution of the present invention preferably includes the following three embodiments.

[Embodiment 1]

Embodiment 1 is an embodiment of using, as the carboxylic acid ester compound represented by the foregoing general formula (I), a compound wherein X is a —C(=O)— group, and n is an integer of 1 to 3.

More specifically, the nonaqueous electrolytic solution having an electrolyte salt dissolved in a nonaqueous solvent is a nonaqueous electrolytic solution containing a carboxylic acid ester compound represented by the following general formula (I-1).

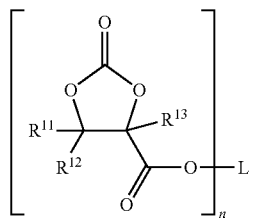

(I-1)

In the formula, each of $R^{11}$ and $R^{12}$ independently represents a hydrogen atom, a halogen atom, an alkyl group having 1 to 6 carbon atoms, in which at least one hydrogen atom may be substituted with a halogen atom, a cycloalkyl group having 3 to 6 carbon atoms, an alkenyl group having 2 to 6 carbon atoms, an alkynyl group having 2 to 6 carbon atoms, an aralkyl group having 7 to 13 carbon atoms, in which at least one hydrogen atom may be substituted with a halogen atom, an aryl group having 6 to 12 carbon atoms, in which at least one hydrogen atom may be substituted with a halogen atom, or a —C(=O)—$OR^{14}$ group, and when $R^{11}$ and $R^{12}$ are each an alkyl group, then $R^{11}$ and $R^{12}$ may be bonded to each other to form a ring structure. $R^{13}$ represents a hydrogen atom, a halogen atom, or an alkyl group having 1 to 6 carbon atoms, and n represents an integer of 1 to 3.

When n is 1, then L and $R^{14}$ may be the same as or different from each other and represent an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, in which at least one hydrogen atom may be substituted with a halogen atom, or an aryl group having 6 to 12 carbon atoms, in which at least one hydrogen atom may be substituted with a halogen atom, and when n is 2 or 3, then L represents an n-valent connecting group constituted of a carbon atom and a hydrogen atom, which may contain an ether bond, a thioether bond, or an $SO_2$ bond, at least one hydrogen atom of L may be substituted with a halogen atom, and $R^{14}$ is the same as described above.

[Embodiment 2]

Embodiment 2 is an embodiment of using, as the carboxylic acid ester compound represented by the foregoing general formula (I), a compound wherein X is an —S(=O)— group, an —S(=O)$_2$— group, or a —$CR^6R^7$ group, and n is 1.

More specifically, the nonaqueous electrolytic solution having an electrolyte salt dissolved in a nonaqueous solvent is a nonaqueous electrolytic solution containing a carboxylic acid ester compound represented by the following general formula (I-2).

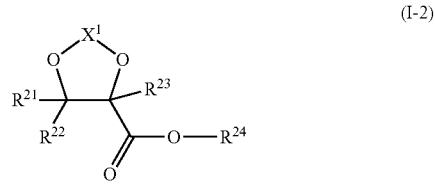

(I-2)

In the formula, each of $R^{21}$ and $R^{22}$ independently represents a hydrogen atom, a halogen atom, an alkyl group having 1 to 6 carbon atoms, in which at least one hydrogen atom may be substituted with a halogen atom, a cycloalkyl group having 3 to 6 carbon atoms, an alkenyl group having 2 to 6 carbon atoms, an alkynyl group having 3 to 6 carbon atoms, an aralkyl group having 7 to 13 carbon atoms, in which at least one hydrogen atom may be substituted with a halogen atom, an aryl group having 6 to 12 carbon atoms, in which at least one hydrogen atom may be substituted with a halogen atom, or a —C(=O)—$OR^{25}$ group, and when $R^{21}$ and $R^{22}$ are each an alkyl group, then $R^{21}$ and $R^{22}$ may be bonded to each other to form a ring structure. $R^{23}$ represents a hydrogen atom, a halogen atom, or an alkyl group having 1 to 6 carbon atoms, and $R^{24}$ and $R^{25}$ may be the same as or different from each other and represent an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, in which at least one hydrogen atom may be substituted with a halogen atom, or an aryl group having 6 to 12 carbon atoms, in which at least one hydrogen atom may be substituted with a halogen atom. $X^1$ represents an —S(=O) group, an —S(=O)$_2$ group, or a —$CR^{26}R^{27}$ group and each of $R^{26}$ and $R^{27}$ independently represents a hydrogen atom or an alkyl group having 1 to 6 carbon atoms, in which at least one hydrogen atom may be substituted with a halogen atom.

[Embodiment 3]

Embodiment 3 is an embodiment of using, as the carboxylic acid ester compound represented by the foregoing general formula (I), a compound wherein X is an —S(=O)$_2$—R$^5$—S(=O)$_2$— group, and n is 1 or 2.

More specifically, the nonaqueous electrolytic solution having an electrolyte salt dissolved in a nonaqueous solvent is a nonaqueous electrolytic solution containing a carboxylic acid ester compound represented by the following general formula (I-3).

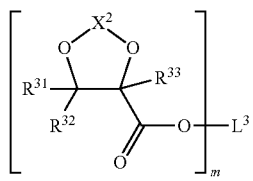

(I-3)

In the formula, each of R$^{31}$ and R$^{32}$ independently represents a hydrogen atom, a halogen atom, an alkyl group having 1 to 6 carbon atoms, in which at least one hydrogen atom may be substituted with a halogen atom, an aryl group having 6 to 12 carbon atoms, in which at least one hydrogen atom may be substituted with a halogen atom, or a —C(=O)—OR$^{34}$ group. R$^{33}$ represents a hydrogen atom, a halogen atom, or an alkyl group having 1 to 6 carbon atoms, and m represents 1 or 2.

When m is 1, then L$^3$ and R$^{34}$ may be the same as or different from each other and represent an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, in which at least one hydrogen atom may be substituted with a halogen atom, or an aryl group having 6 to 12 carbon atoms, in which at least one hydrogen atom may be substituted with a halogen atom, and when m is 2, then L$^3$ represents an alkylene group having 2 to 8 carbon atoms, an alkenylene group having 4 to 8 carbon atoms, or an alkynylene group having 4 to 8 carbon atoms, at least one hydrogen atom of L$^3$ may be substituted with a halogen atom, and R$^{34}$ is the same as described above.

X$^2$ represents an —S(=O)$_2$—R$^{35}$—S(=O)$_2$— group, and R$^{35}$ represents an alkylene group having 1 to 4 carbon atoms, in which at least one hydrogen atom may be substituted with a halogen atom or an alkyl group having 1 to 4 carbon atoms.

[Nonaqueous Electrolytic Solution of Embodiment 1]

According to the nonaqueous electrolytic solution of Embodiment 1 of the present invention, in the nonaqueous electrolytic solution having an electrolyte salt dissolved in a nonaqueous solvent, the compound represented by the foregoing general formula (I) wherein X is a —C(=O)— group, and n is an integer of 1 to 3, more specifically the carboxylic acid ester compound represented by the foregoing general formula (I-1) is contained in the nonaqueous electrolytic solution.

Although the reasons why the nonaqueous electrolytic solution of Embodiment 1 is able to greatly improve the electrochemical characteristics of an energy storage device when used at a high temperature and at a high voltage are not always elucidated yet, the following may be considered.

In view of the fact that the compound represented by the general formula (I-1), which is used in Embodiment 1, has a hetero ring which is reductively decomposed at the α-position of the carbonyl group to form a surface film, it has high reactivity and quickly reacts with active sites of both a positive electrode and a negative electrode, thereby forming a firmer surface film. Therefore, it may be considered that not only the storage characteristics at a high temperature and at a high voltage are improved, but also the gas generation to be caused due to decomposition of the solvent is inhibited.

The carboxylic acid ester compound which is contained in the nonaqueous electrolytic solution of Embodiment 1 is represented by the following general formula (I-1).

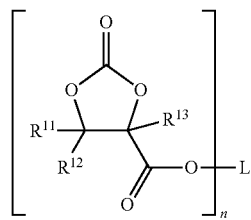

(I-1)

In the formula, each of R$^{11}$ and R$^{12}$ independently represents a hydrogen atom, a halogen atom, an alkyl group having 1 to 6 carbon atoms, in which at least one hydrogen atom may be substituted with a halogen atom, a cycloalkyl group having 3 to 6 carbon atoms, an alkenyl group having 2 to 6 carbon atoms, an alkynyl group having 2 to 6 carbon atoms, an aralkyl group having 7 to 13 carbon atoms, in which at least one hydrogen atom may be substituted with a halogen atom, an aryl group having 6 to 12 carbon atoms, in which at least one hydrogen atom may be substituted with a halogen atom, or a —C(=O)—OR$^{14}$ group, and when R$^{11}$ and R$^{12}$ are each an alkyl group, then R$^{11}$ and R$^{12}$ may be bonded to each other to form a ring structure. R$^{13}$ represents a hydrogen atom, a halogen atom, or an alkyl group having 1 to 6 carbon atoms, and n represents an integer of 1 to 3.

When n is 1, then L and R$^{14}$ may be the same as or different from each other and represent an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, in which at least one hydrogen atom may be substituted with a halogen atom, or an aryl group having 6 to 12 carbon atoms, in which at least one hydrogen atom may be substituted with a halogen atom, and when n is 2 or 3, then L represents an n-valent connecting group constituted of a carbon atom and a hydrogen atom, which may contain an ether bond, a thioether bond, or an SO$_2$ bond, at least one hydrogen atom of L may be substituted with a halogen atom, and R$^{14}$ is the same as described above.

In the foregoing general formula (I-1), each of R$^{11}$ and R$^{12}$ is independently preferably a hydrogen atom, a halogen atom, an alkyl group having 1 to 6 carbon atoms, in which at least one hydrogen atom may be substituted with a halogen atom, a cycloalkyl group having 3 to 6 carbon atoms, an alkenyl group having 2 to 6 carbon atoms, an alkynyl group having 3 to 6 carbon atoms, or a —C(=O)—OR$^{14}$ group, and more preferably a hydrogen atom, a halogen atom, an alkyl group having 1 to 4 carbon atoms, in which at least one hydrogen atom may be substituted with a halogen atom, or a —C(=O)—OR$^{14}$ group. When R$^{11}$ and R$^{12}$ are each an alkyl group, then R$^{11}$ and R$^{12}$ may be bonded to each other to form a ring structure.

R$^{13}$ is preferably a hydrogen atom or a halogen atom, and more preferably a hydrogen atom. n is preferably 1 or 2, and more preferably 1.

When n is 1, then L and R$^{14}$ may be the same as or different from each other and are preferably an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, or an aryl group having 6 to 12 carbon atoms, in which at least one hydrogen atom may be substituted with a halogen atom, and more preferably an alkenyl group having 2 to 6 carbon atoms or an alkynyl group having 3 to 6 carbon atoms.

As specific examples of R$^{11}$ and R$^{12}$, there are suitably exemplified a hydrogen atom; a halogen atom, such as a fluorine atom, a chlorine atom, a bromine atom, etc.; a straight-chain alkyl group, such as a methyl group, an ethyl group, an n-propyl group, an n-butyl group, an n-pentyl group, an n-hexyl group, etc.; a branched alkyl group, such as an isopropyl group, a sec-butyl group, a 2-pentyl group, a 3-pentyl group, a tert-butyl group, a tert-amyl group, etc.; a halogenated alkyl group, such as a fluoromethyl group, a difluoromethyl group, a trifluoromethyl group, a 2-chloroethyl group, a 2-fluoroethyl group, a 2,2-difluoroethyl group, a 2,2,2-trifluoroethyl group, a 3-fluoropropyl group, a 3-chloropropyl group, a 3,3-difluoropropyl group, a 3,3,3-trifluoropropyl group, a 2,2,3,3-tetrafluoropropyl group, a 2,2,3,3,3-pentafluoropropyl group, etc.; a cycloalkyl group, such as a cyclopropyl group, a cyclobutyl group, a cyclopentyl group, a cyclohexyl group, a cycloheptyl group, etc.; an alkenyl group, such as vinyl group, a 1-propen-1-yl group, a 2-propen-1-yl group, a 2-buten-1-yl group, a 3-buten-1-yl group, a 4-penten-1-yl group, a 5-hexen-1-yl group, a 1-propen-2-yl group, a 1-buten-2-yl group, a 2-methyl-2-propen-1-yl group, etc.; an alkynyl group, such as an ethynyl group, a 2-propynyl group, a 2-butynyl group, a 3-butynyl group, a 4-heptynyl group, a 1-methyl-2-propynyl group, a 1,1-dimethyl-2-propynyl group, a 1-methyl-3-butynyl group, a 1-methyl-4-heptynyl group, etc.; an aralkyl group, such as a benzyl group, a 4-methylbenzyl group, a 4-tert-butylbenzyl group, a 4-fluorobenzyl group, a 4-chlorobenzyl group, a 1-phenylethan-1-yl group, a 2-phenylethan-1-yl group, a 3-phenylpropan-1-yl group, etc.; and an aryl group, such as a phenyl group, a 2-methylphenyl group, a 3-methylphenyl group, a 4-methylphenyl group, a 4-tert-butylphenyl group, a 2-fluorophenyl group, a 4-fluorophenyl group, a 2-trifluoromethylphenyl group, a 3-trifluoromethylphenyl group, a 4-trifluoromethylphenyl group, a 4-fluoro-2-trifluoromethylphenyl group, a 4-fluoro-3-trifluoromethylphenyl group, a 2,6-difluorophenyl group, a 3,5-difluorophenyl group, a 2,4,6-trifluorophenyl group, a 2,3,5,6-tetrafluorophenyl group, a perfluorophenyl group, etc.; and also a methoxycarbonyl group, an ethoxycarbonyl group, a 2,2,2-trifluoroethoxycarbonyl group, a 2,2,3,3-tetrafluoropropoxycarbonyl group, a cyclopentyloxycarbonyl group, a cyclohexyloxycarbonyl group, a vinyloxycarbonyl group, a 1-propen-1-yloxycarbonyl group, a 2-propen-1-yloxycarbonyl group, a 2-propynyloxycarbonyl group, a 1-methyl-2-propynyloxycarbonyl group, a benzyloxycarbonyl group, a phenyloxycarbonyl group, a 4-fluorophenyloxycarbonyl group, a 2-trifluoromethylphenyloxycarbonyl group, a 4-fluoro-3-trifluoromethylphenyloxycarbonyl group, a 2,3,5,6-tetrafluorophenyloxycarbonyl group, a perfluorophenyloxycarbonyl group, and the like.

Of the foregoing, R$^{11}$ and R$^{12}$ are preferably a hydrogen atom, a fluorine atom, a chlorine atom, a methyl group, an ethyl group, an n-propyl group, an n-butyl group, an n-pentyl group, an n-hexyl group, an isopropyl group, a sec-butyl group, a tert-butyl group, a trifluoromethyl group, a 2,2,2-trifluoroethyl group, a 2,2,3,3-tetrafluoropropyl group, a cyclopentyl group, a cyclohexyl group, a vinyl group, a 1-propen-1-yl group, a 2-propen-1-yl group, a 2-buten-1-yl group, a 1-propen-2-yl group, a 2-methyl-2-propen-1-yl group, an ethynyl group, a 2-propynyl group, a 1-methyl-2-propynyl group, a methoxycarbonyl group, an ethoxycarbonyl group, a 2,2,2-trifluoroethoxycarbonyl group, a 2,2,3,3-tetrafluoropropoxycarbonyl group, a vinyloxycarbonyl group, a 1-propen-1-yloxycarbonyl group, a 2-propen-1-yloxycarbonyl group, a 2-propynyloxycarbonyl group, a 1-methyl-2-propynyloxycarbonyl group, a phenyloxycarbonyl group, a 2-trifluoromethylphenyloxycarbonyl group, a 4-fluoro-3-trifluoromethylphenyloxycarbonyl group, a 2,3,5,6-tetrafluorophenyloxycarbonyl group, or a perfluorophenyloxycarbonyl group; and more preferably a hydrogen atom, a fluorine atom, a methyl group, an ethyl group, a trifluoromethyl group, a 2-propen-1-yloxycarbonyl group, or a 2-propenyloxycarbonyl group.

When R$^{11}$ and R$^{12}$ are each an alkyl group, then R$^{11}$ and R$^{12}$ may be bonded to each other to form a ring structure. As specific examples thereof, there are suitably exemplified an ethane-1,2-diyl group, a propane-1,3-diyl group, a butane-1,4-diyl group, and a pentane-1,5-diyl group, with a butane-1,4-diyl group or a pentane-1,5-diyl group being preferred.

As specific examples of R$^{13}$, there are suitably exemplified a hydrogen atom; a halogen atom, such as a fluorine atom, a chlorine atom, a bromine atom, etc.; a straight-chain alkyl group, such as a methyl group, an ethyl group, an n-propyl group, an n-butyl group, an n-pentyl group, an n-hexyl group, etc.; and a branched alkyl group, such as an isopropyl group, a sec-butyl group, a 2-pentyl group, a pentan-3-yl group, a tert-butyl group, a tert-amyl group, etc. Above all, a hydrogen atom, a fluorine atom, a chlorine atom, a methyl group, an ethyl group, an n-propyl group, an n-butyl group, an isopropyl group, a sec-butyl group, or a tert-butyl group is preferred, with a hydrogen atom, a fluorine atom, a methyl group, or an ethyl group being more preferred.

As specific examples of L, there are suitably exemplified the following groups.

(i) In the case of n=1:

There are suitably exemplified a straight-chain alkyl group, such as a methyl group, an ethyl group, an n-propyl group, an n-butyl group, an n-pentyl group, an n-hexyl group, etc.; a branched alkyl group, such as an isopropyl group, a sec-butyl group, a 2-pentyl group, a 3-pentyl group, a tert-butyl group, a tert-amyl group, etc.; a halogenated alkyl group, such as a fluoromethyl group, a difluoromethyl group, a 2-chloroethyl group, a 2-fluoroethyl group, a 2,2-difluoroethyl group, a 2,2,2-trifluoroethyl group, a 3-fluoropropyl group, a 3-chloropropyl group, a 3,3-difluoropropyl group, a 3,3,3-trifluoropropyl group, a 2,2,3,3-tetrafluoropropyl group, a 2,2,3,3,3-pentafluoropropyl group, etc.; a cycloalkyl group, such as a cyclopropyl group, a cyclobutyl group, a cyclopentyl group, a cyclohexyl group, a cycloheptyl group, etc.; a halogenated cycloalkyl group, such as a 4-fluorocyclohexyl group, a 4-chlorocyclohexyl group, etc.; an alkenyl group, such as a vinyl group, a 1-propen-1-yl group, a 2-propen-1-yl group, a 2-buten-1-yl group, a 3-buten-1-yl group, a 4-penten-1-yl group, a 5-hexen-1-yl group, a 1-propen-2-yl group, a 1-buten-2-yl group, a 2-methyl-2-propen-1-yl group, etc.; a haloalkenyl group, such as a 3,3-difluoro-2-propen-1-yl group, a 4,4-difluoro-3-buten-1-yl group, a 3,3-dichloro-2-propen-1-yl group, a 4,4-dichloro-3-buten-1-yl group, etc.; an alkynyl group, such as a 2-propynyl group, a 2-butynyl group, a 3-butynyl group, a 4-heptynyl group, a 1-methyl-2-propynyl group, a 1,1-dimethyl-2-propynyl group, a 1-methyl-3-butynyl group, a 1-methyl-4-heptynyl group, etc.; an alkoxyalkyl group, such as a methoxymethyl group, an ethoxymethyl group, a methoxyethyl group, an ethoxyethyl group, an n-propoxyethyl group, an n-butoxyethyl group, a methoxypropyl group, an ethoxypropyl group, etc.; an aralkyl group, such as a benzyl group, a 4-methylbenzyl group, a 4-tert-butylbenzyl group, a 4-fluorobenzyl group, a 4-chlorobenzyl group, a 1-phenylethan-1-yl group, a 2-phenylethan-1-yl group, a 3-phenylpropan-1-yl group, etc.; an aryl group, such as a phenyl group, a 2-methylphenyl group, a 3-methylphenyl group, a 4-methylphenyl group, a 4-tert-butylphenyl group, a 2-fluorophenyl group, a 4-fluorophenyl group, a 2-trifluoromethylphenyl group, a 3-trifluoromethylphenyl group, a 4-trifluoromethylphenyl group, a 4-fluoro-2-trifluoromethylphenyl group, a 4-fluoro-3-trifluoromethylphenyl group, a 2,6-difluorophenyl group, a 3,5-difluorophenyl group, a 2,4,6-trifluorophenyl group, a 2,3,5,6-tetrafluorophenyl group, a perfluorophenyl group, etc.; and the like.

In the case of n=1, of the foregoing, L is preferably a methyl group, an ethyl group, an n-propyl group, an n-butyl group, an isopropyl group, a sec-butyl group, a 2,2,2-trifluoroethyl group, a 2,2,3,3-tetrafluoropropyl group, a cyclopropyl group, a cyclobutyl group, a cyclopentyl group, a cyclohexyl group, a vinyl group, a 1-propen-1-yl group, a 2-propen-1-yl group, a 2-buten-1-yl group, a 3-buten-1-yl group, a 1-propen-2-yl group, a 1-buten-2-yl group, a 2-methyl-2-propen-1-yl group, a 3,3-difluoro-2-propen-1-yl group, a 4,4-difluoro-3-buten-1-yl group, a 3,3-dichloro-2-propen-1-yl group, a 4,4-dichloro-3-buten-1-yl group, a 2-propynyl group, a 2-butynyl group, a 3-butynyl group, a 1-methyl-2-propynyl group, a 1,1-dimethyl-2-propynyl group, a 2,3,5,6-tetrafluorophenyl group, or a perfluorophenyl group; and more preferably a vinyl group, a 1-propen-1-yl group, a 2-propen-1-yl group, a 2-buten-1-yl group, a 1-propen-2-yl group, a 3,3-difluoro-2-propen-1-yl group, a 4,4-difluoro-3-buten-1-yl group, a 2-propynyl group, a 2-butynyl group, a 3-butynyl group, or a 1-methyl-2-propynyl group.

(ii) In the case of n=2:
There are suitably exemplified a straight-chain alkylene group, such as an ethylene group, a propane-1,3-diyl group, a butane-1,4-diyl group, a pentane-1,5-diyl group, a hexane-1,6-diyl group, etc.; a branched alkylene group, such as a propane-1,2-diyl group, a butane-1,3-diyl group, a butane-2,3-diyl group, a 2-methylpropane-1,2-diyl group, a 2,2-dimethylpropane-1,3-thyl group, etc.; a haloalkylene group, such as a 2,2-difluoropropane-1,3-diyl group, a 2,2,3,3-tetrafluorobutane-1,4-diyl group, a 2,2,3,3,4,4-hexafluoropentane-1,5-diyl group, a 2,2,3,3,4,4,5,5-octafluorohexane-1,6-diyl group, a 2,2-dichloropropane-1,3-diyl group, a 2,2,3,3-tetrachlorobutene-1,4-diyl group, etc.; an alkenylene group, such as a 2-butene-1,4-diyl group, a 2-pentene-1,5-diyl group, a 3-hexene-1,6-diyl group, a 3-hexene-2,5-group, a 2,5-dimethyl-3-hexene-2,5-diyl group, etc.; an alkynylene group, such as a 2-butyne-1,4-diyl group, a 2-pentyne-1,5-diyl group, a 3-hexyne-1,6-diyl group, a 3-hexyne-2,5-diyl group, a 2,5-dimethyl-3-hexyne-2,5-diyl group, etc.; a cycloalkylene group, such as a cyclopentane-1,2-thyl group, a cyclopentane-1,3-diyl group, a cyclohexane-1,2-diyl group, a cyclohexane-1,3-diyl group, a cycloheptane-1,3-diyl group, a cyclohexane-1,4-diyl group, a cycloheptane-1,4-diyl group, etc.; a connecting group having an ether group, such as —CH$_2$CH$_2$OCH$_2$CH$_2$—, —CH$_2$CH$_2$OCH$_2$CH$_2$OCH$_2$CH$_2$—, —CH$_2$CH$_2$CH$_2$OCH$_2$CH$_2$CH$_2$—, —CH(CH$_3$)CH$_2$OCH$_2$CH(CH$_3$)—, etc.; a connecting group having a thioether bond, such as —CH$_2$CH$_2$SCH$_2$CH$_2$—, —CH$_2$CH$_2$CH$_2$SCH$_2$CH$_2$CH$_2$—, etc.; a connecting group having an S(=O)$_2$ bond, such as —CH$_2$CH$_2$S(=O)$_2$CH$_2$CH$_2$—, —CH$_2$CH$_2$CH$_2$S(=O)$_2$CH$_2$CH$_2$CH$_2$—, etc.; and an aromatic connecting group, such as a benzene-1,2-diyl group, a benzene-1,3-diyl group, a benzene-1,4-diyl group, etc.

In the case of n=2, of the foregoing, L is preferably an ethylene group, a propane-1,3-diyl group, a butane-1,4-diyl group, a pentane-1,5-diyl group, a hexane-1,6-diyl group, a propane-1,2-diyl group, a butane-2,3-diyl group, a 2,2-dimethylpropane-1,3-diyl group, a 2-butene-1,4-diyl group, a 3-hexene-2,5-diyl group, a 2-butyne-1,4-diyl group, a 3-hexyne-2,5-diyl group, a cyclohexane-1,2-diyl group, a cyclohexane-1,4-diyl group, a cycloheptane-1,2-diyl group, —CH$_2$CH$_2$OCH$_2$CH$_2$—, —CH$_2$CH$_2$S(=O)$_2$CH$_2$CH$_2$—, or a benzene-1,4-diyl group, and more preferably a 2-butene-1,4-diyl group or a 2-butyne-1,4-diyl group.

(iii) In the case of n=3:
There are suitably exemplified groups having the following structures. ("*" in the following structures represents a bonding site.)

[Chem. 9]

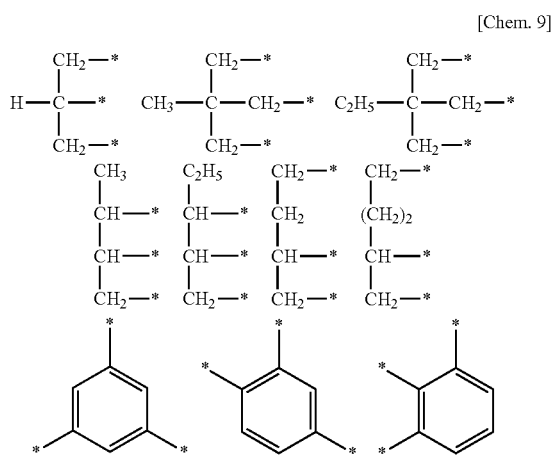

As the compound represented by the foregoing general formula (I-1), specifically, there are suitably exemplified the following compounds.

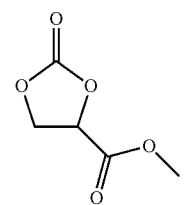

1

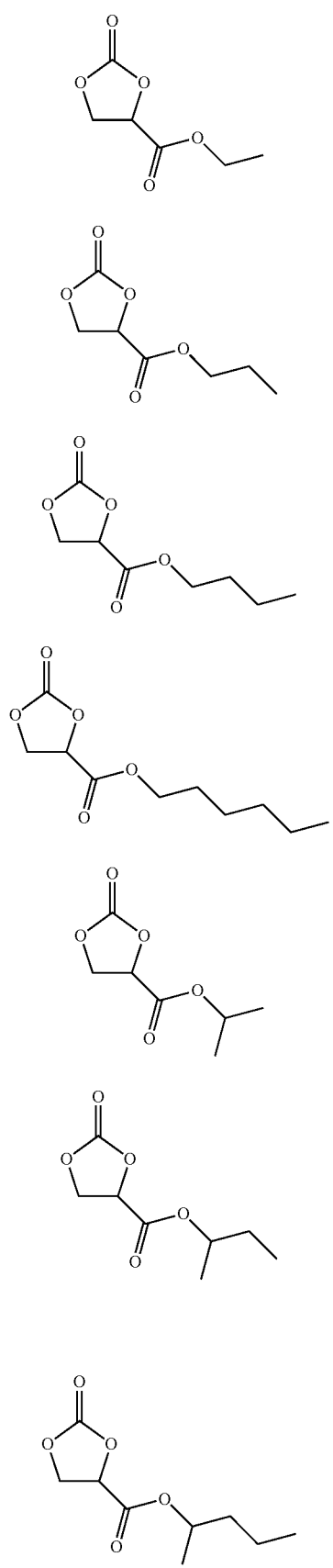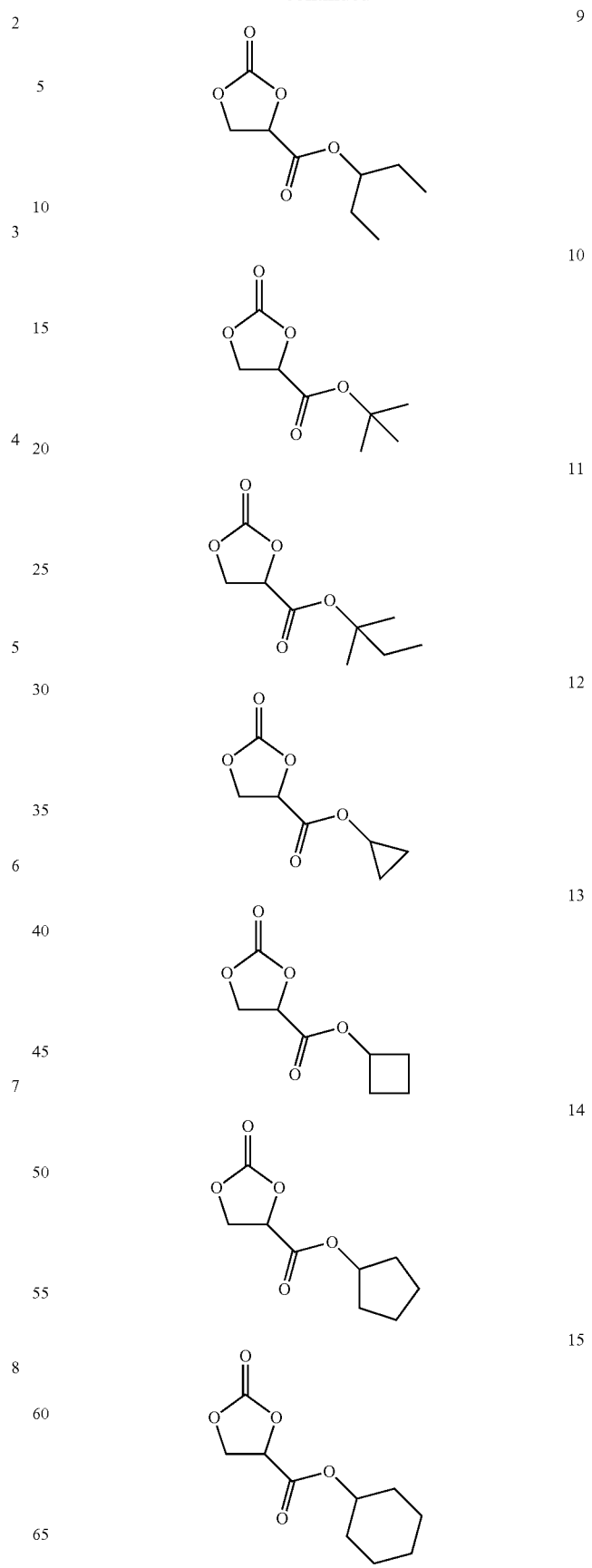

-continued
16
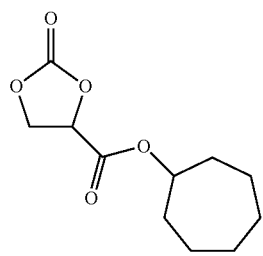
17
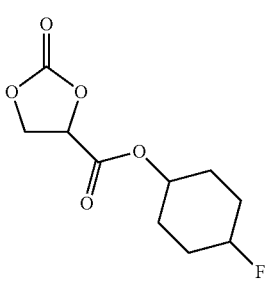
18
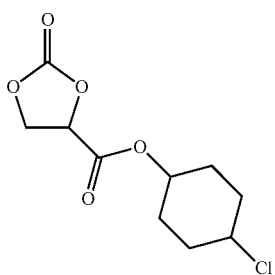
19
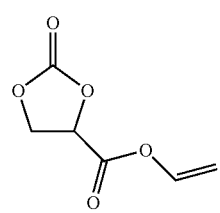
20
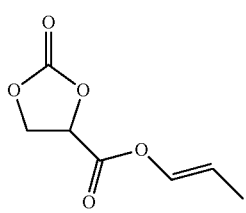
21
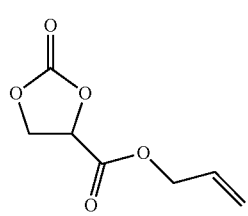
-continued
22
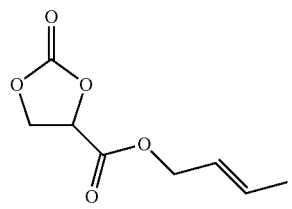
23
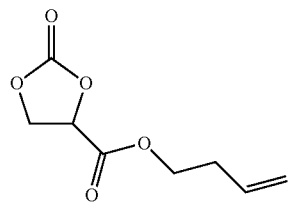
24
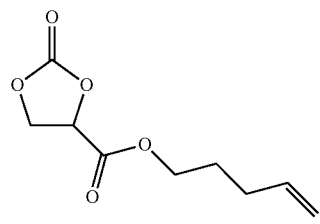
25
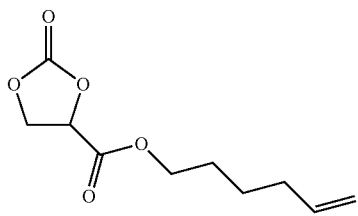
26
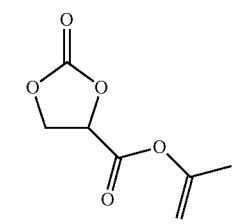
27
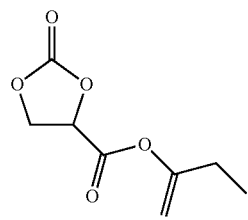
28
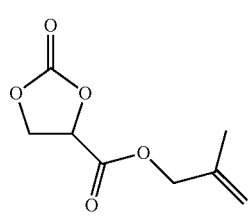

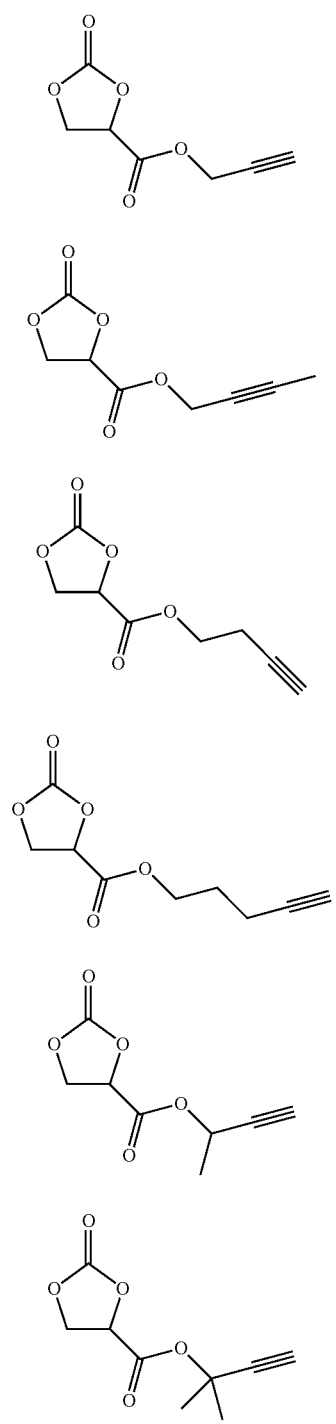
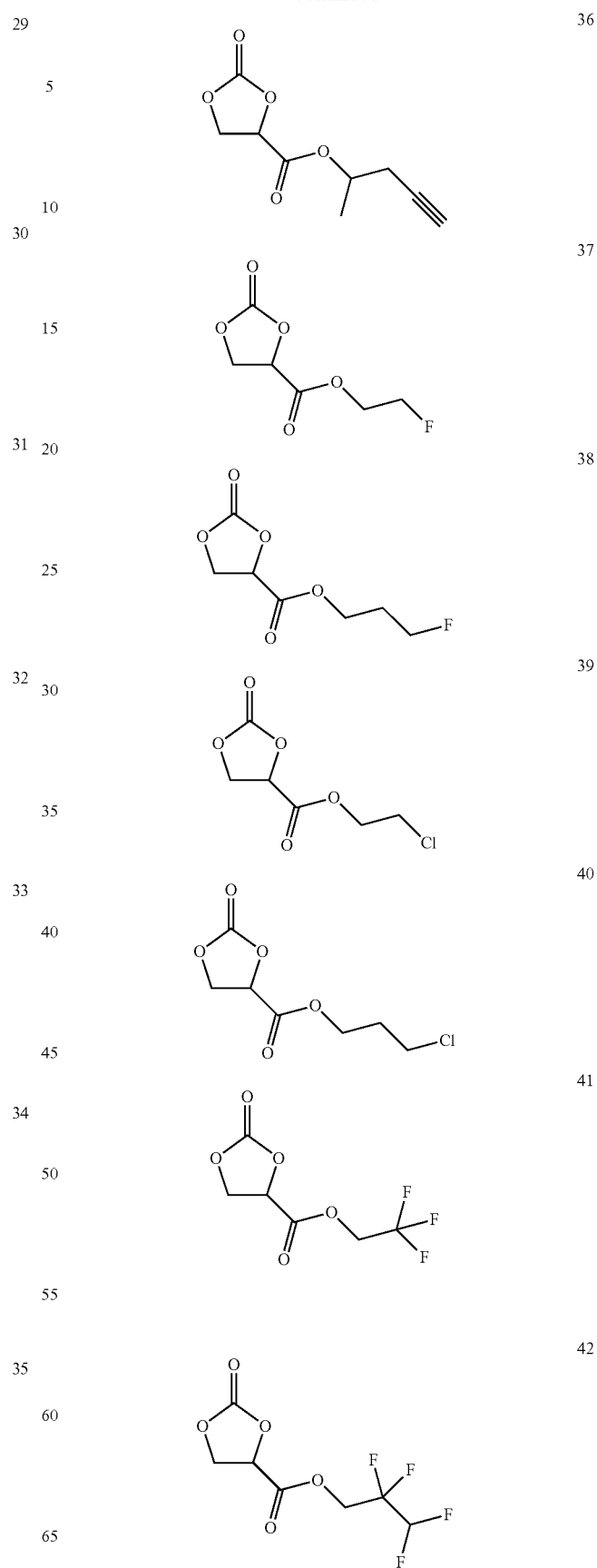

43
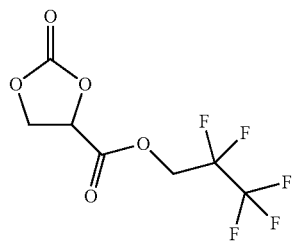
44
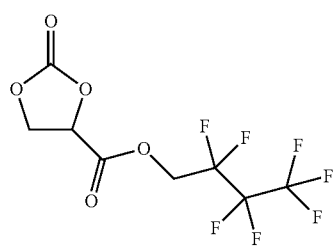
45
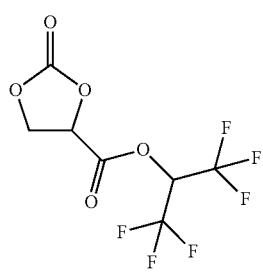
46
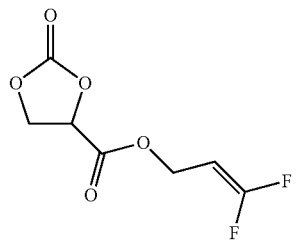
47
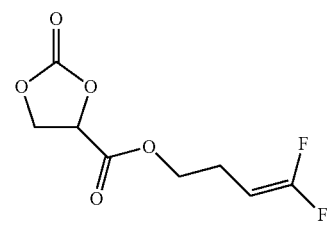
48
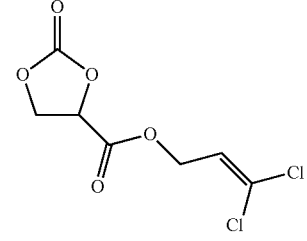
49
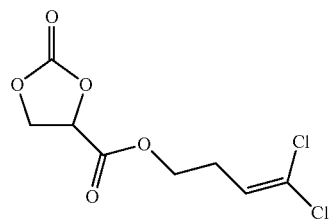
50
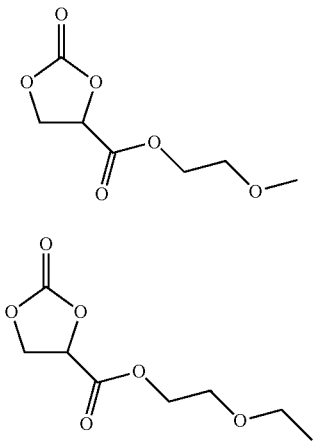
51
52
53
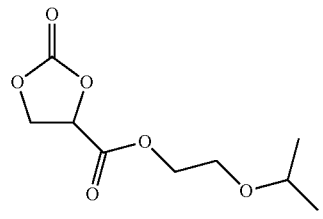
54
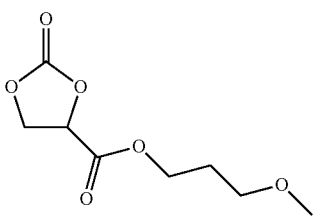
55
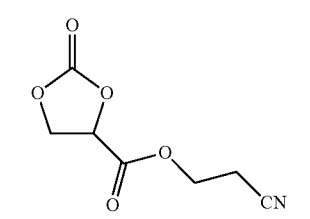
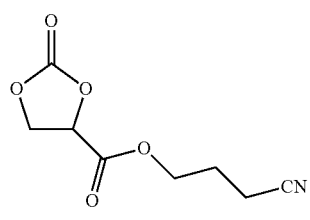

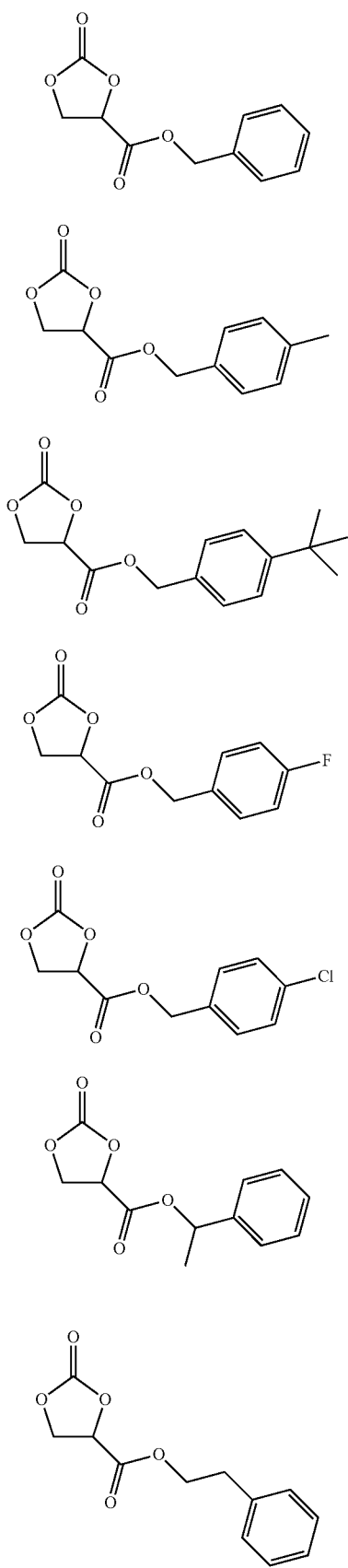
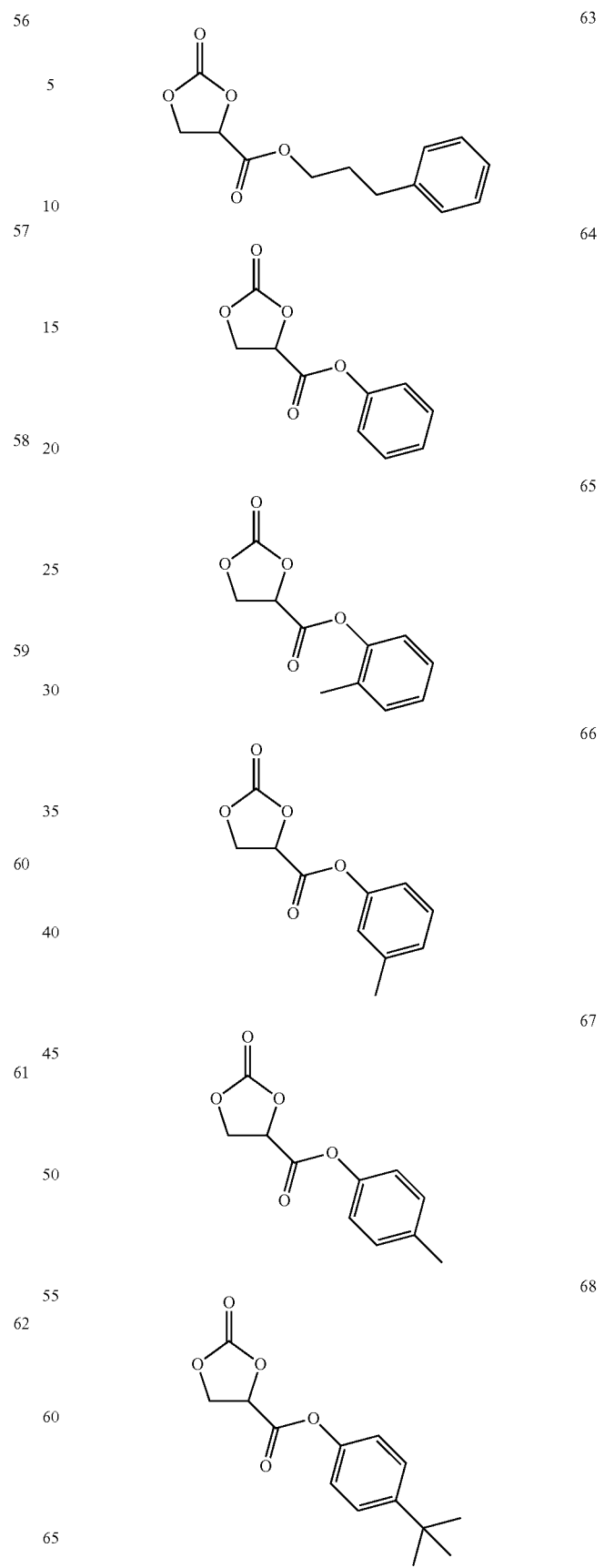

69
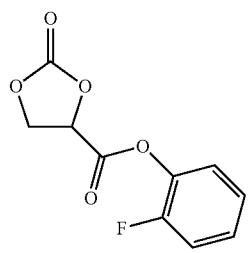
70
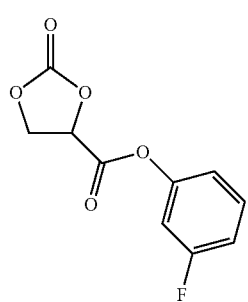
71
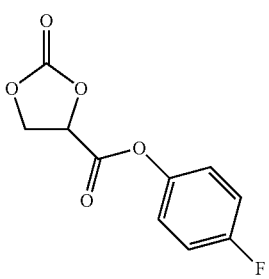
72
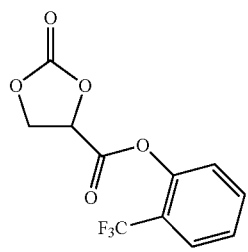
73
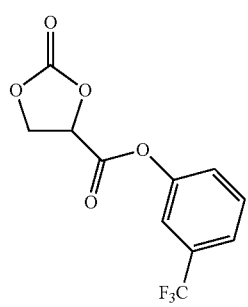
74
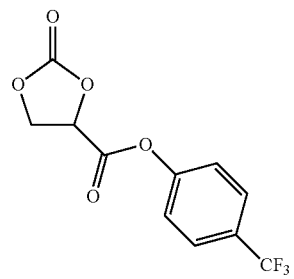
75
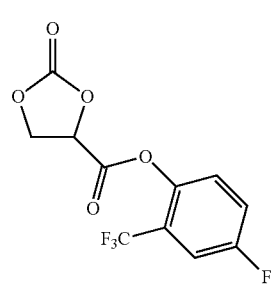
76
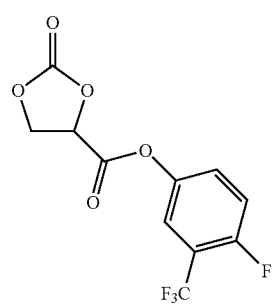
77
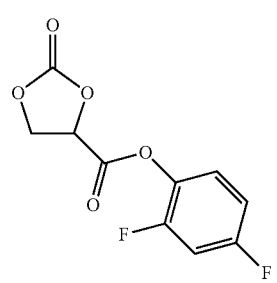
78
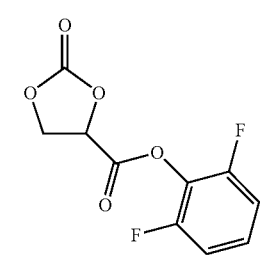

79
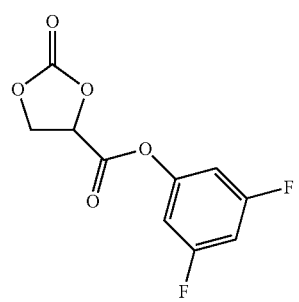
80
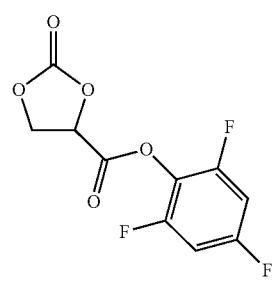
81
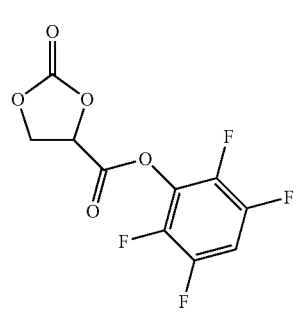
82
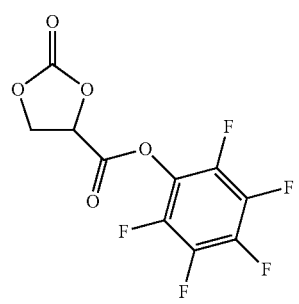
83
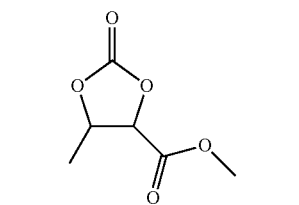
84
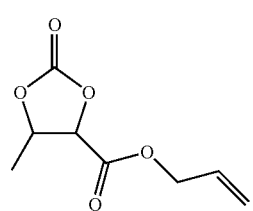
85
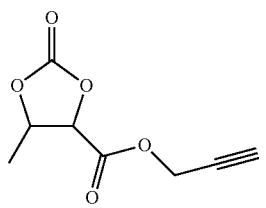
86
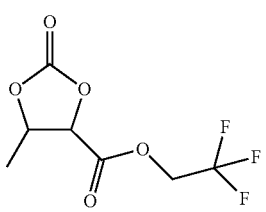
87
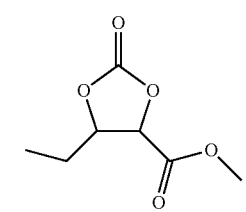
88
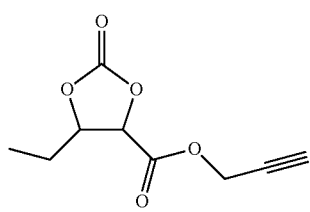
89
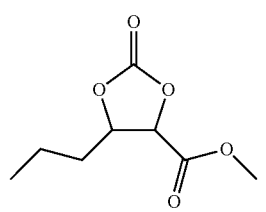
90
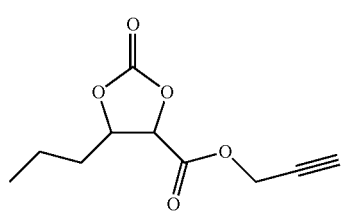
91
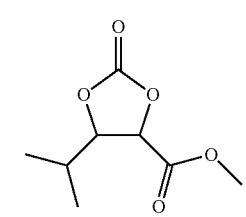

-continued
92 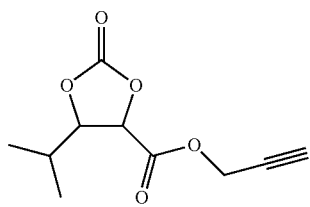
93 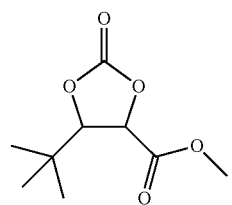
94 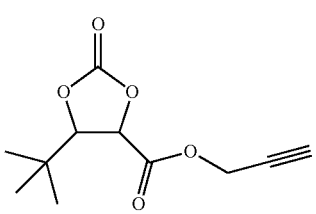
95 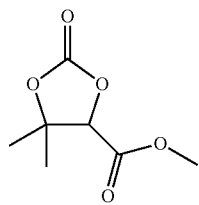
96 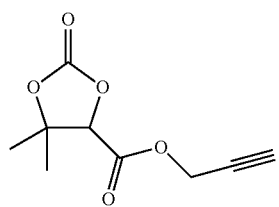
97 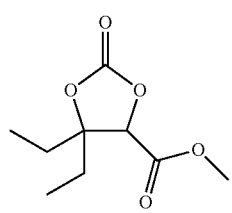
98 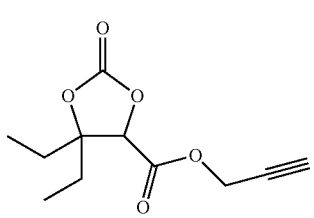
-continued
99 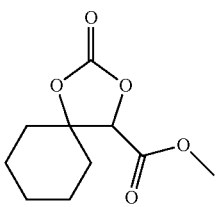
100 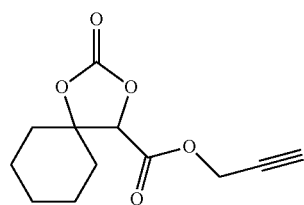
101 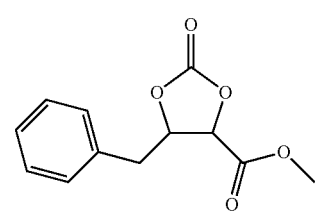
102 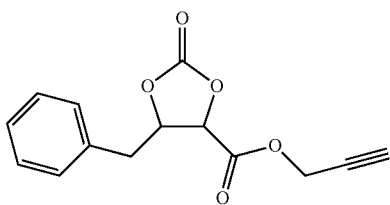
103 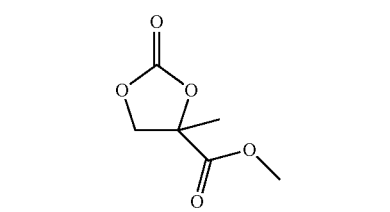
104 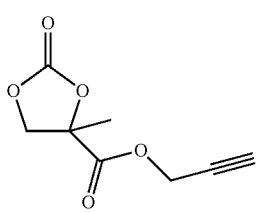
105 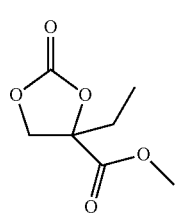

106 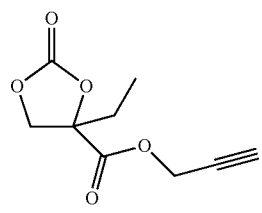
107 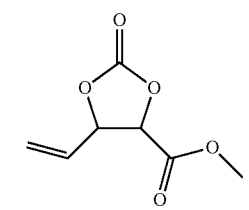
108 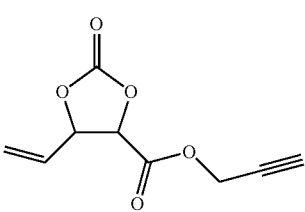
109 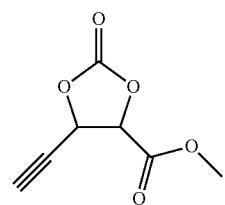
110 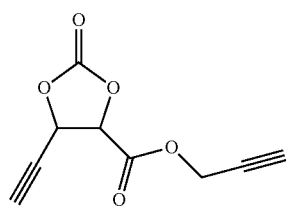
111 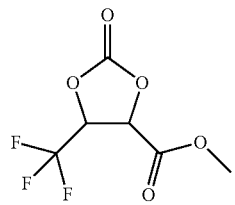
112 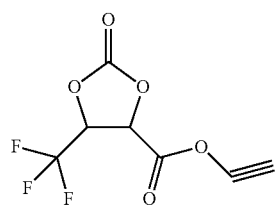
113 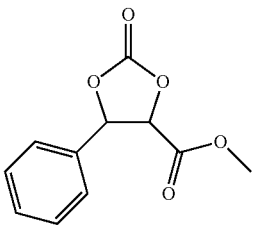
114 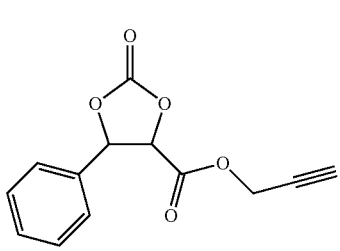
115 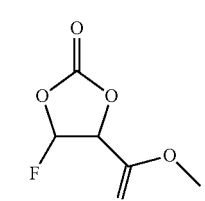
116 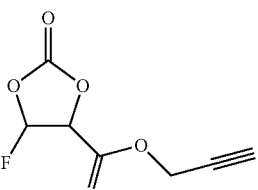
117 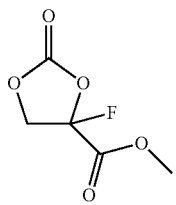
118 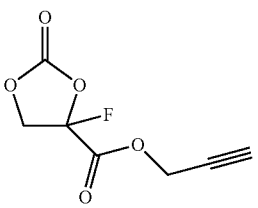
119 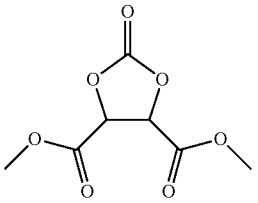

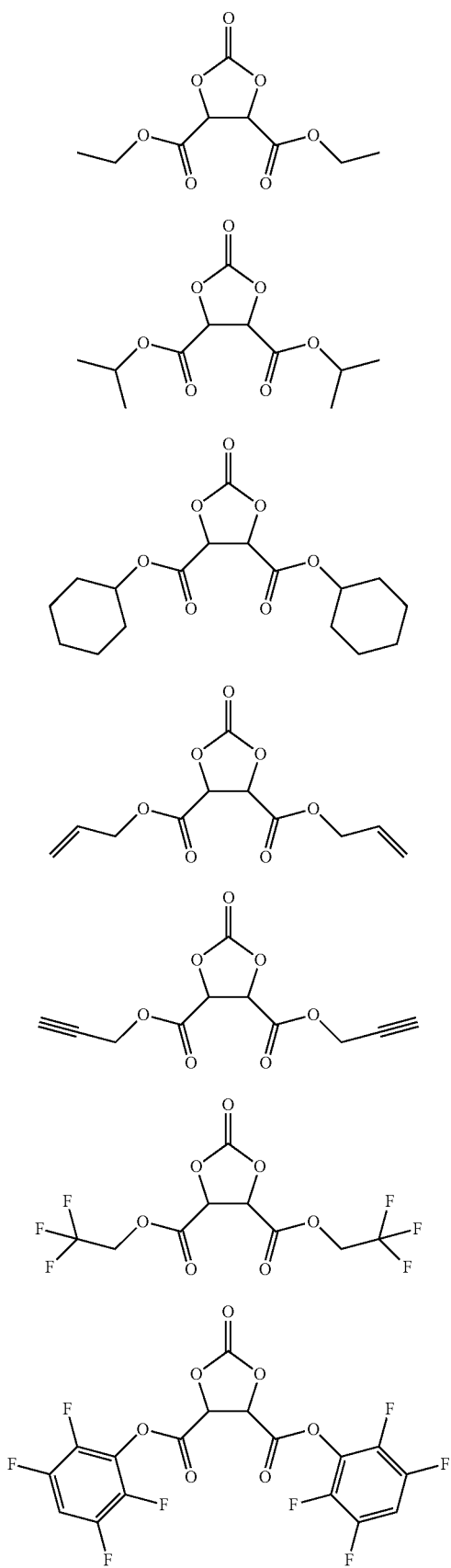
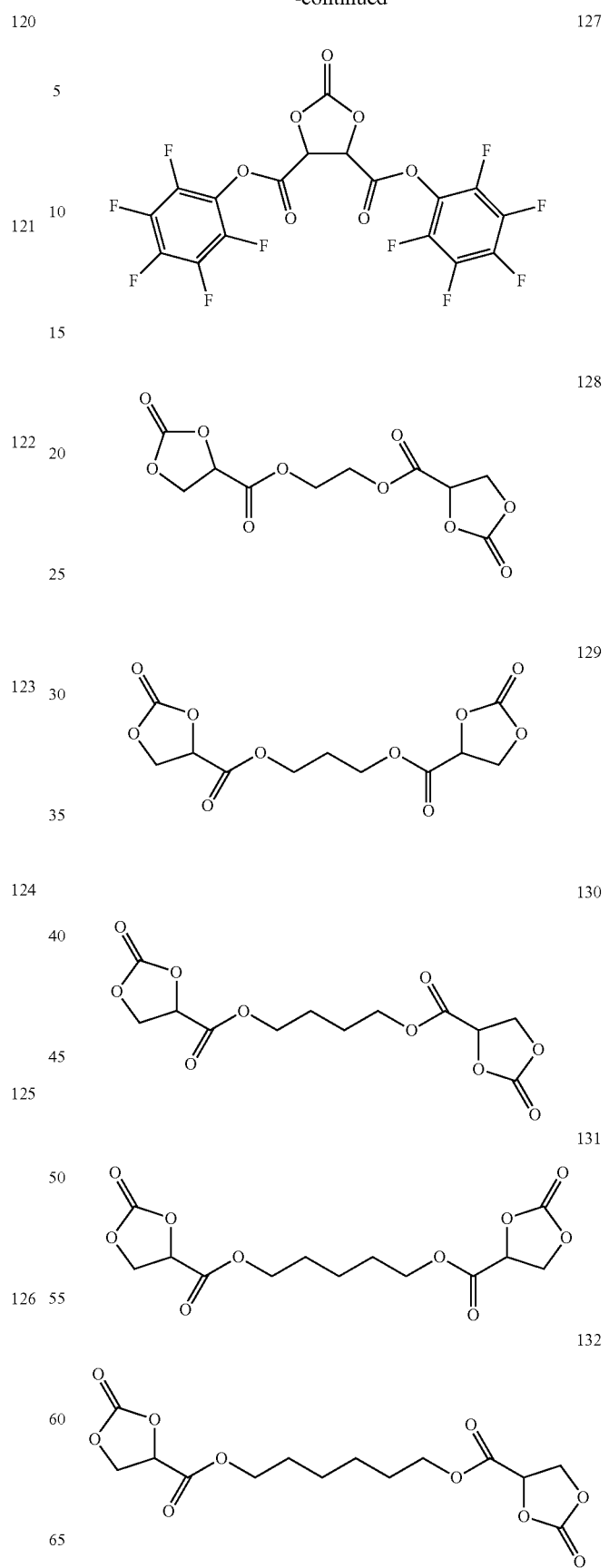

133
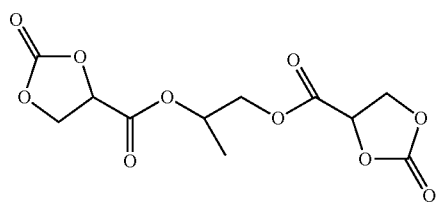
134
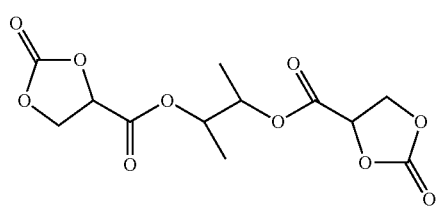
135
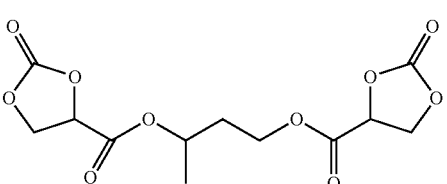
136
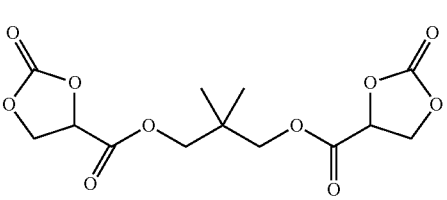
137
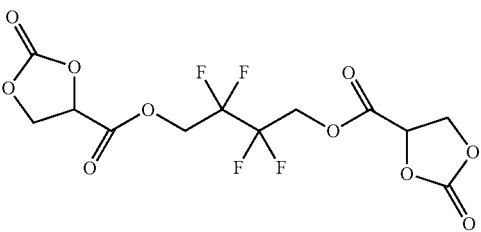
138
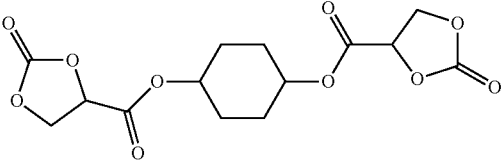
139
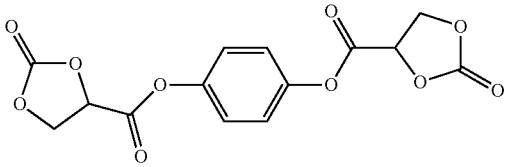
140
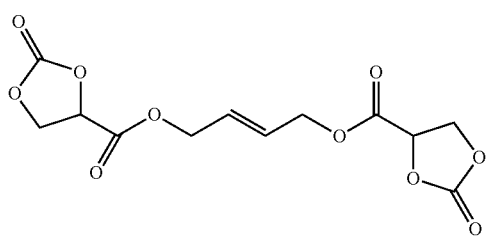
141
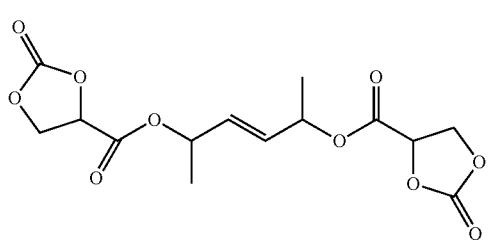
142
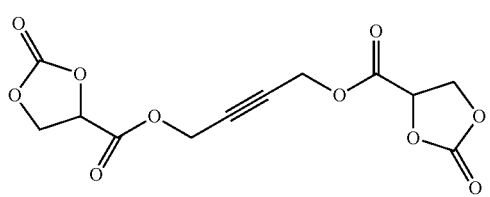
143
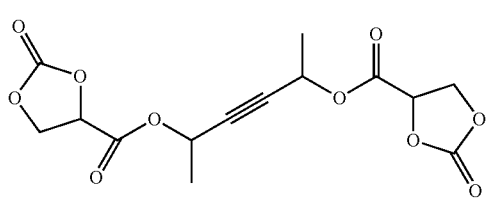
144
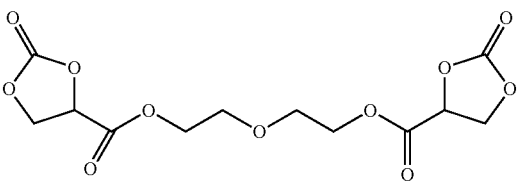
145
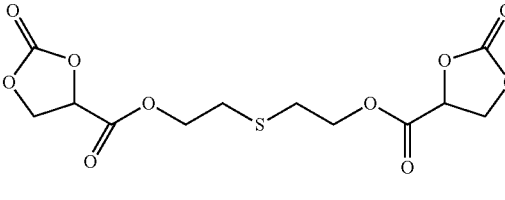
146
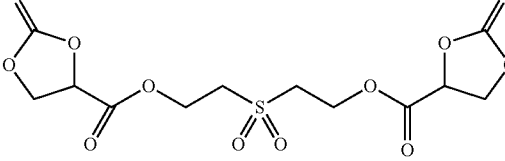

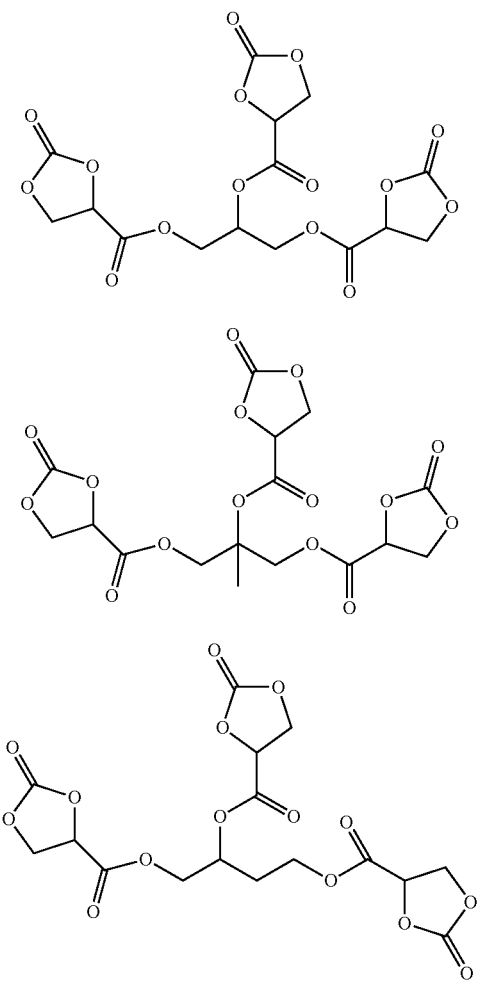

Among the aforementioned compounds, as the compound represented by the general formula (I-1), the compounds having any one of the structural formulae of 1 to 4, 6, 7, 12 to 15, 19 to 23, 26, 27, 29 to 31, 33, 34, 41, 42, 46 to 49, 81, 82, 84, 85, 88, 89, 112, 115 to 131, 133 to 136, 138, 140 to 143, 146, 147, and 148 are more preferred; the compounds having any one of the structural formulae of 19 to 21, 26, 29, 30, 33, 46, 47, 81, 82, 84, 85, 88, 115 to 118, 123, 124, and 140 to 143 are still more preferred; and 2-propenyl 2-oxo-1,3-dioxolane-4-carboxylate (structural formula 21), 2-propynyl 2-oxo-1,3-dioxolane-4-carboxylate (structural formula 29), 2-propynyl 5-fluoro-2-oxo-1,3-dioxolane-4-carboxylate (structural formula 116), 2-propynyl 4-fluoro-2-oxo-1,3-dioxolane-4-carboxylate (structural formula 118), di(2-propenyl) 2-oxo-1,3-dioxolane-4,5-dicarboxylate (structural formula 123), di(2-propynyl) 2-oxo-1,3-dioxolane-4,5-dicarboxylate (structural formula 124), 2-butene-1,4-diyl bis(2-oxo-1,3-dioxolane-4-carboxylate) (structural formula 140), and 2-butyne-1,4-bis(2-oxo-1,3-dioxolane-4-carboxylate) (structural formula 142) are especially preferred.

In the nonaqueous electrolytic solution of the present invention, a content of the carboxylic acid ester compound represented by the foregoing general formula (I-1) is preferably 0.001 to 30% by mass in the nonaqueous electrolytic solution. So long as the content is 30% by mass or less, there is less concern that a surface film is excessively formed on an electrode, so that in the case of using a battery at a high temperature and at a high voltage, the storage characteristics are worsened. So long as the content is 0.001% by mass or more, the formation of a surface film is sufficient, and in the case of using a battery at a high temperature and at a high voltage, an improving effect of the storage characteristics is enhanced. The content is preferably 0.01% by mass or more, and more preferably 0.3% by mass or more in the nonaqueous electrolytic solution. An upper limit thereof is preferably 20% by mass or less, more preferably 10% by mass or less, and especially preferably 5% by mass or less.

[Nonaqueous Electrolytic Solution of Embodiment 2]

According to the nonaqueous electrolytic solution of Embodiment 2 of the present invention, in the nonaqueous electrolytic solution having an electrolyte salt dissolved in a nonaqueous solvent, the compound represented by the foregoing general formula (I) wherein X is an —S(=O)— group, an —S(=O)$_2$— group, or a —CR$^6$R$^7$ group, and n is 1, more specifically the carboxylic acid ester compound represented by the foregoing general formula (I-2) is contained in the nonaqueous electrolytic solution.

Although the reasons why the nonaqueous electrolytic solution of Embodiment 2 is able to greatly improve the electrochemical characteristics of an energy storage device when used at a high temperature and at a high voltage are not always elucidated yet, the following may be considered.

The compound represented by the general formula (I-2), which is used in Embodiment 2, has an —S(=O)— group, an —S(=O)$_2$— group, or a —CR$^6$R$^7$ group and at least one carboxylic acid ester group that is an electron attractive group. For this reason, as compared with the compounds not having a carboxylic acid ester group but having only the ring structure as described in PTLs 4 to 6, it may be considered that the reactivity on the electrode becomes much higher, the compound represented by the general formula (I-2) quickly reacts with active sites of both the positive electrode and the negative electrode. Furthermore, it may be considered that in view of the fact that the carboxylic acid ester is contained in the surface film, the compound forms a firmer surface film, improves the storage characteristics at a high temperature and at a high voltage, and inhibits the gas generation to de caused due to decomposition of the solvent.

The carboxylic acid ester compound which is contained in the nonaqueous electrolytic solution of Embodiment 2 is represented by the following general formula (I-2).

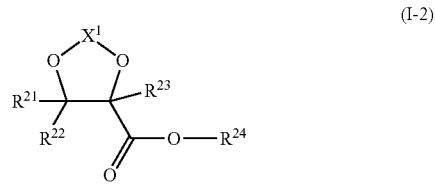

In the formula, each of $R^{21}$ and $R^{22}$ independently represents a hydrogen atom, a halogen atom, an alkyl group having 1 to 6 carbon atoms, in which at least one hydrogen atom may be substituted with a halogen atom, a cycloalkyl group having 3 to 6 carbon atoms, an alkenyl group having 2 to 6 carbon atoms, an alkynyl group having 3 to 6 carbon atoms, an aralkyl group having 7 to 13 carbon atoms, in which at least one hydrogen atom may be substituted with a halogen atom, an aryl group having 6 to 12 carbon atoms, in which at least one hydrogen atom may be substituted with a halogen atom, or a —C(=O)—OR$^{25}$ group, and when R$^{21}$ and R$^{22}$ are each an alkyl group, then R$^{21}$ and R$^{22}$ may be bonded to each other to form a ring structure. R$^{23}$ represents a hydrogen atom, a halogen atom, or an alkyl group having 1 to 6 carbon atoms, and R$^{24}$ and R$^{25}$ may be the same as or different from each other and represent an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, in which at least one hydrogen atom may be substituted with a halogen atom, or an aryl group having 6 to 12 carbon atoms, in which at least one hydrogen atom may be substituted with a halogen atom. X$^1$ represents an —S(=O) group, an —S(=O)$_2$ group, or a —CR$^{26}$R$^{27}$ group, and each of R$^{26}$ and R$^{27}$ independently represents a hydrogen atom or an alkyl group having 1 to 6 carbon atoms, in which at least one hydrogen atom may be substituted with a halogen atom.

As specific examples of R$^{21}$ and R$^{22}$, there are suitably exemplified a hydrogen atom; a halogen atom, such as a fluorine atom, a chlorine atom, a bromine atom, etc.; a straight-chain alkyl group, such as a methyl group, an ethyl group, an n-propyl group, an n-butyl group, an n-pentyl group, an n-hexyl group, etc.; a branched alkyl group, such as an isopropyl group, a sec-butyl group, a 2-pentyl group, a 3-pentyl group, a tert-butyl group, a tert-amyl group, etc.; a halogenated alkyl group, such as a fluoromethyl group, a difluoromethyl group, a trifluoromethyl group, a 2-chloroethyl group, a 2-fluoroethyl group, a 2,2-difluoroethyl group, a 2,2,2-trifluoroethyl group, a 3-fluoropropyl group, a 3-chloropropyl group, a 3,3-difluoropropyl group, a 3,3,3-trifluoropropyl group, a 2,2,3,3-tetrafluoropropyl group, a 2,2,3,3,3-pentafluoropropyl group, etc.; a cycloalkyl group, such as a cyclopropyl group, a cyclobutyl group, a cyclopentyl group, a cyclohexyl group, a cycloheptyl group, etc.; an alkenyl group, such as vinyl group, a 1-propen-1-yl group, a 2-propen-1-yl group, a 2-buten-1-yl group, a 3-buten-1-yl group, a 4-penten-1-yl group, a 5-hexen-1-yl group, a 1-propen-2-yl group, a 1-buten-2-yl group, a 2-methyl-2-propen-1-yl group, etc.; an alkynyl group, such as an ethynyl group, a 2-propynyl group, a 2-butynyl group, a 3-butynyl group, a 4-heptynyl group, a 1-methyl-2-propynyl group, a 1,1-dimethyl-2-propynyl group, a 1-methyl-3-butynyl group, a 1-methyl-4-heptynyl group, etc.; an aralkyl group, such as a benzyl group, a 4-methylbenzyl group, a 4-tert-butylbenzyl group, a 4-fluorobenzyl group, a 4-chlorobenzyl group, a 1-phenylethan-1-yl group, a 2-phenylethan-1-yl group, a 3-phenylpropan-1-yl group, etc.; and an aryl group, such as a phenyl group, a 2-methylphenyl group, a 3-methylphenyl group, a 4-methylphenyl group, a 4-tert-butylphenyl group, a 2-fluorophenyl group, a 4-fluorophenyl group, a 2-trifluoromethylphenyl group, a 3-trifluoromethylphenyl group, a 4-trifluoromethylphenyl group, a 4-fluoro-2-trifluoromethylphenyl group, a 4-fluoro-3-trifluoromethylphenyl group, a 2,6-difluorophenyl group, a 3,5-difluorophenyl group, a 2,4,6-trifluorophenyl group, a 2,3,5,6-tetrafluorophenyl group, a perfluorophenyl group, etc.; and also a methoxycarbonyl group, an ethoxycarbonyl group, a 2,2,2-trifluoroethoxycarbonyl group, a 2,2,3,3-tetrafluoropropoxycarbonyl group, a cyclopentyloxycarbonyl group, a cyclohexyloxycarbonyl group, a vinyloxycarbonyl group, a 1-propen-1-yloxycarbonyl group, a 2-propen-1-yloxycarbonyl group, a 2-propynyloxycarbonyl group, a 1-methyl-2-propynyloxycarbonyl group, a benzyloxycarbonyl group, a phenyloxycarbonyl group, a 4-fluorophenyloxycarbonyl group, a 2-trifluoromethylphenyloxycarbonyl group, a 4-fluoro-3-trifluoromethylphenyloxycarbonyl group, a 2,3,5,6-tetrafluorophenyloxycarbonyl group, a perfluorophenyloxycarbonyl group, and the like.

Of the foregoing, R$^{21}$ and R$^{22}$ are preferably a hydrogen atom, a fluorine atom, a chlorine atom, a methyl group, an ethyl group, an n-propyl group, an n-butyl group, an n-pentyl group, an n-hexyl group, an isopropyl group, a sec-butyl group, a tert-butyl group, a trifluoromethyl group, a 2,2,2-trifluoroethyl group, a 2,2,3,3-tetrafluoropropyl group, a cyclopentyl group, a cyclohexyl group, a vinyl group, a 1-propen-1-yl group, a 2-propen-1-yl group, a 2-buten-1-yl group, a 1-propen-2-yl group, a 2-methyl-2-propen-1-yl group, an ethynyl group, a 2-propynyl group, a 1-methyl-2-propynyl group, a methoxycarbonyl group, an ethoxycarbonyl group, a 2,2,2-trifluoroethoxycarbonyl group, a 2,2,3,3-tetrafluoropropoxycarbonyl group, a vinyloxycarbonyl group, a 1-propen-1-yloxycarbonyl group, a 2-propen-1-yloxycarbonyl group, a 2-propynyloxycarbonyl group, a 1-methyl-2-propynyloxycarbonyl group, a phenyloxycarbonyl group, a 2-trifluoromethylphenyloxycarbonyl group, a 4-fluoro-3-trifluoromethylphenyloxycarbonyl group, a 2,3,5,6-tetrafluorophenyloxycarbonyl group, or a perfluorophenyloxycarbonyl group; and more preferably a hydrogen atom, a fluorine atom, a methyl group, an ethyl group, a trifluoromethyl group, a methoxycarbonyl group, an ethoxycarbonyl group, a 2,2,2-trifluoroethoxycarbonyl group, a 2-propen-1-yloxycarbonyl group, or a 2-propynyloxycarbonyl group.

When R$^{21}$ and R$^{22}$ are each an alkyl group, as examples of a ring structure which R$^{21}$ and R$^{22}$ may be bonded to each other, there are suitably exemplified an ethane-1,2-diyl group, a propane-1,3-diyl group, a butane-1,4-diyl group, and a pentane-1,5-diyl group, with a butane-1,4-diyl group or a pentane-1,5-diyl group being preferred.

As specific examples of R$^{23}$, there are suitably exemplified a hydrogen atom; a halogen atom, such as a fluorine atom, a chlorine atom, a bromine atom, etc.; a straight-chain alkyl group, such as a methyl group, an ethyl group, an n-propyl group, an n-butyl group, an n-pentyl group, an n-hexyl group, etc.; and a branched alkyl group, such as an isopropyl group, a sec-butyl group, a 2-pentyl group, a pentan-3-yl group, a tert-butyl group, a tert-amyl group, etc. Above all, a hydrogen atom, a fluorine atom, a chlorine atom, a methyl group, an ethyl group, an n-propyl group, an n-butyl group, an isopropyl group, a sec-butyl group, or a tert-butyl group is preferred, with a hydrogen atom, a fluorine atom, a methyl group, or an ethyl group being more preferred.

As specific examples of R$^{24}$, there are suitably exemplified a straight-chain alkyl group, such as a methyl group, an ethyl group, an n-propyl group, an n-butyl group, an n-pentyl group, an n-hexyl group, etc.; a branched alkyl group, such as an isopropyl group, a sec-butyl group, a 2-pentyl group, a 3-pentyl group, a tert-butyl group, a tert-amyl group, etc.; a halogenated alkyl group, such as a fluoromethyl group, a difluoromethyl group, a 2-chloroethyl group, a 2-fluoroethyl group, a 2,2-difluoroethyl group, a 2,2,2-trifluoroethyl group, a 3-fluoropropyl group, a 3-chloropropyl group, a 3,3-difluoropropyl group, a 3,3,3-trifluoropropyl group, a 2,2,3,3-tetrafluoropropyl group, a 2,2,3,3,3-pentafluoropropyl group, etc.; a cycloalkyl group, such as a cyclopropyl group, a cyclobutyl group, a cyclopentyl group, a cyclohexyl group, a cycloheptyl group, etc.; a halogenated cycloalkyl group, such as a 4-fluorocyclohexyl group, a 4-chlorocyclohexyl group, etc.; an alkenyl group, such as a vinyl group, a 1-propen-1-yl group, a 2-propen-1-yl group, a 2-buten-1-yl group, a 3-buten-1-yl group, a 4-penten-1-yl group, a 5-hexen-1-yl group, a 1-propen-2-yl group, a 1-buten-2-yl group, a 2-methyl-2-propen-1-yl group, etc.; a haloalkenyl group, such as a 3,3-difluoro-2-propen-1-yl group, a 4,4-difluoro-3-buten-1-yl group, a 3,3-dichloro-2-propen-1-yl group, a 4,4-dichloro-3-buten-1-yl group, etc.; an alkynyl group, such as a 2-propynyl group, a 2-butynyl group, a 3-butynyl group, a 4-heptynyl group, a 1-methyl-2-propynyl group, a 1,1-dimethyl-2-propynyl group, a 1-methyl-3-butynyl group, a 1-methyl-4-heptynyl group, etc.; an alkoxyalkyl group, such as a methoxymethyl group, an ethoxymethyl group, a methoxyethyl group, an ethoxyethyl group, an n-propoxyethyl group, an n-butoxyethyl group, a methoxypropyl group, an ethoxypropyl group, etc.; an aralkyl group, such as a benzyl group, a 4-methylbenzyl group, a 4-tert-butylbenzyl group, a 4-fluorobenzyl group, a 4-chlorobenzyl group, a 1-phenylethan-1-yl group, a 2-phenylethan-1-yl group, a 3-phenylpropan-1-yl group, etc.; an aryl group, such as a phenyl group, a 2-methylphenyl group, a 3-methylphenyl group, a 4-methylphenyl group, a 4-tert-butylphenyl group, a 2-fluorophenyl group, a 4-fluorophenyl group, a 2-trifluoromethylphenyl group, a 3-trifluoromethylphenyl group, a 4-trifluoromethylphenyl group, a 4-fluoro-2-trifluoromethylphenyl group, a 4-fluoro-3-trifluoromethylphenyl group, a 2,4-difluorophenyl group, a 2,6-difluorophenyl group, a 3,5-difluorophenyl group, a 2,4,6-trifluorophenyl group, a 2,3,5,6-tetrafluorophenyl group, a perfluorophenyl group, etc.; and the like.

Of the foregoing, $R^{24}$ is preferably a methyl group, an ethyl group, an n-propyl group, an n-butyl group, an isopropyl group, a sec-butyl group, a 2,2,2-trifluoroethyl group, a 2,2,3,3-tetrafluoropropyl group, a cyclopropyl group, a cyclobutyl group, a cyclopentyl group, a cyclohexyl group, a vinyl group, a 1-propen-1-yl group, a 2-propen-1-yl group, a 2-buten-1-yl group, a 3-buten-1-yl group, a 1-propen-2-yl group, a 1-buten-2-yl group, a 2-methyl-2-propen-1-yl group, a 3,3-difluoro-2-propen-1-yl group, a 4,4-difluoro-3-buten-1-yl group, a 3,3-dichloro-2-propen-1-yl group, a 4,4-dichloro-3-buten-1-yl group, a 2-propynyl group, a 2-butynyl group, a 3-butynyl group, a 1-methyl-2-propynyl group, a 1,1-dimethyl-2-propynyl group, a 4-fluoro-3-trifluoromethylphenyl group, or a perfluorophenyl group, and more preferably a methyl group, an ethyl group, a 2,2,2-trifluoroethyl group, a 2,2,3,3-tetrafluoropropyl group, a 2-propen-1-yl group, a 2-propynyl group, a 2-butynyl group, or a 1-methyl-2-propynyl group.

$X^1$ represents an —S(=O) group, an —S(=O)$_2$ group, or a —CR$^{26}$R$^{27}$ group. Specific examples of R$^{26}$ and R$^{27}$ include a hydrogen atom; a straight-chain alkyl group, such as a methyl group, an ethyl group, an n-propyl group, an n-butyl group, an n-pentyl group, an n-hexyl group, etc.; a branched alkyl group, such as an isopropyl group, a sec-butyl group, a 2-pentyl group, a 3-pentyl group, a tert-butyl group, a tert-amyl group, etc.; or a halogenated alkyl group, such as a trifluoromethyl group, a 2,2,2-trifluoroethyl group, a 2,2,3,3-tetrafluoropropyl group, a perfluorobutyl group, a 1,1,1,3,3,3-hexafluoroisopropyl group, etc., with a hydrogen atom or a methyl group being preferred, and it is more preferred that R$^{26}$ and R$^{27}$ each are a hydrogen atom.

Among the foregoing, $X^1$ is more preferably an —S(=O) group or an —S(=O)$_2$ group, and especially preferably an —S(=O)$_2$ group.

As the compound represented by the foregoing general formula (I-2), specifically, there are suitably exemplified the following compounds.

(A) In the case where $X^1$ is an —S(=O) group:

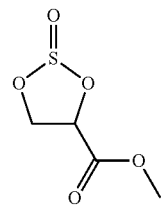

A1

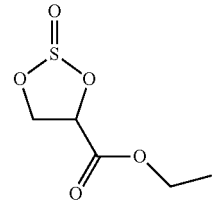

A2

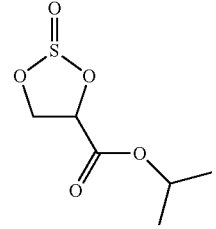

A3

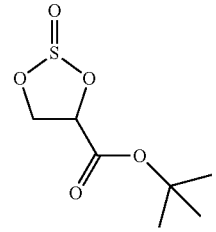

A4

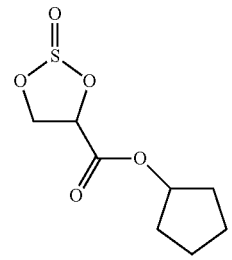

A5

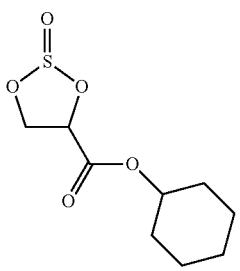

A6

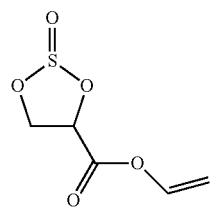 A7
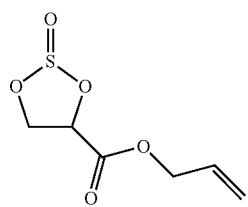 A8
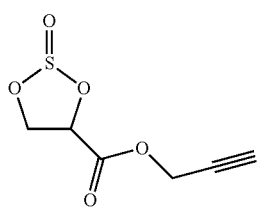 A9
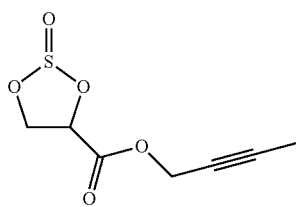 A10
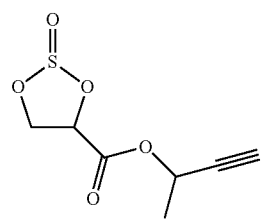 A11
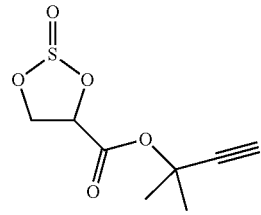 A12
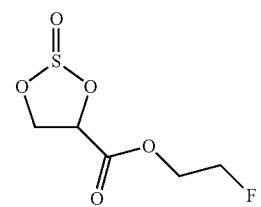 A13
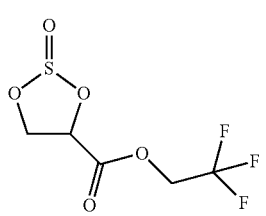 A14
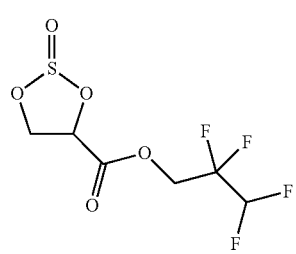 A15
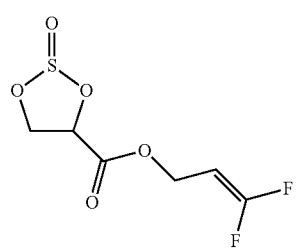 A16
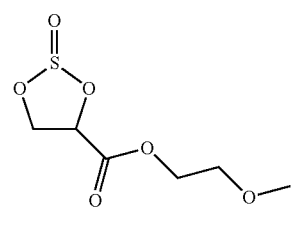 A17
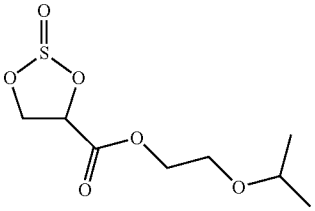 A18
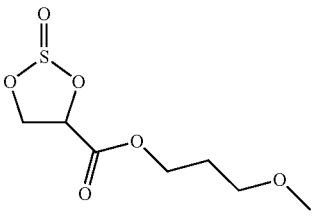 A19
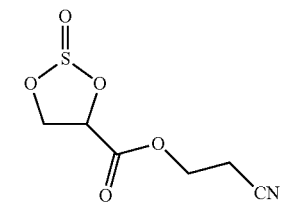 A20

A21 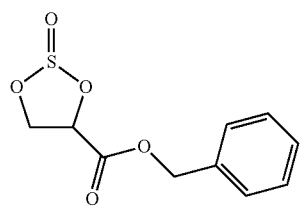
A22 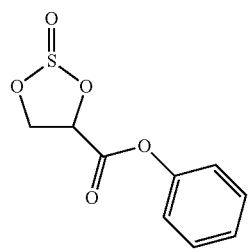
A23 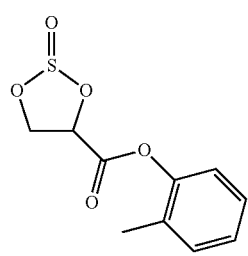
A24 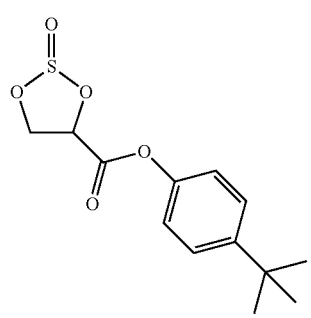
A25 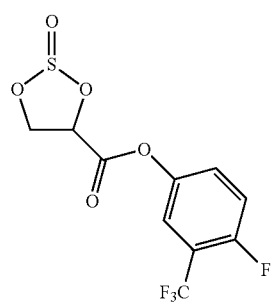
A26 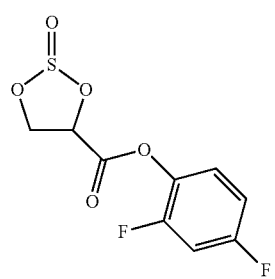
A27 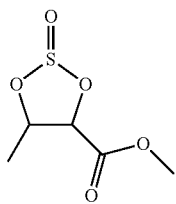
A28 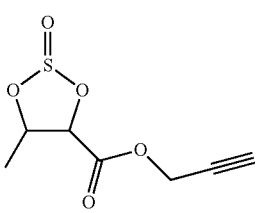
A29 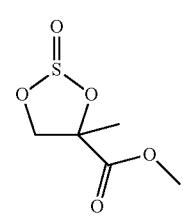
A30 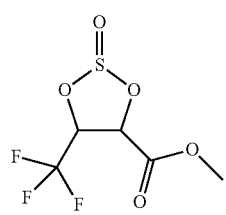
A31 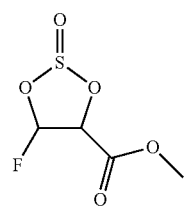
A32 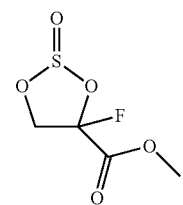
A33 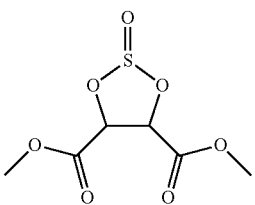

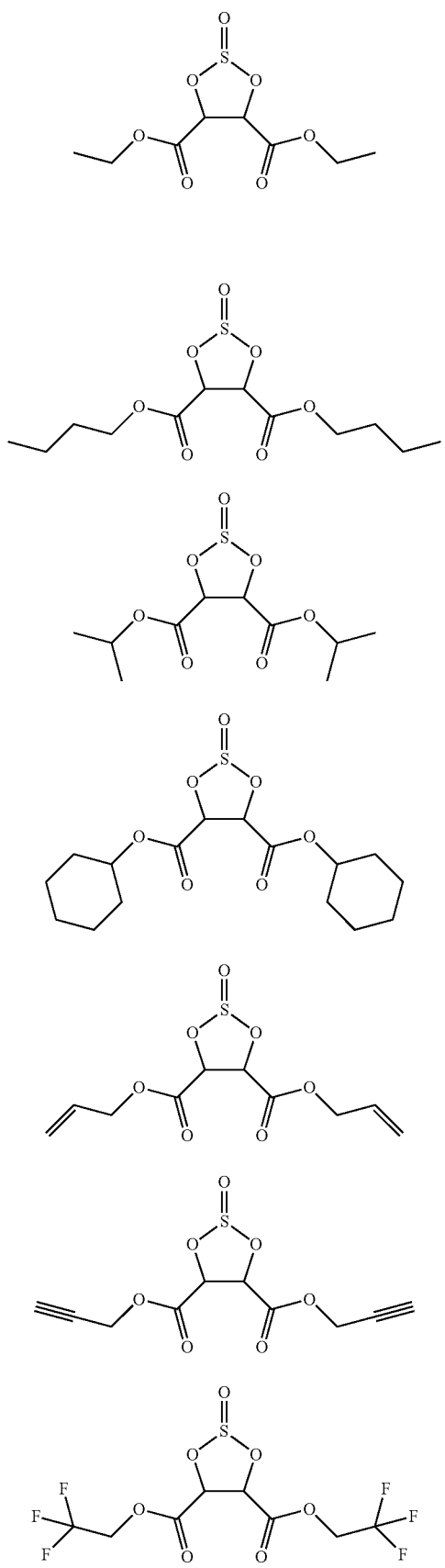
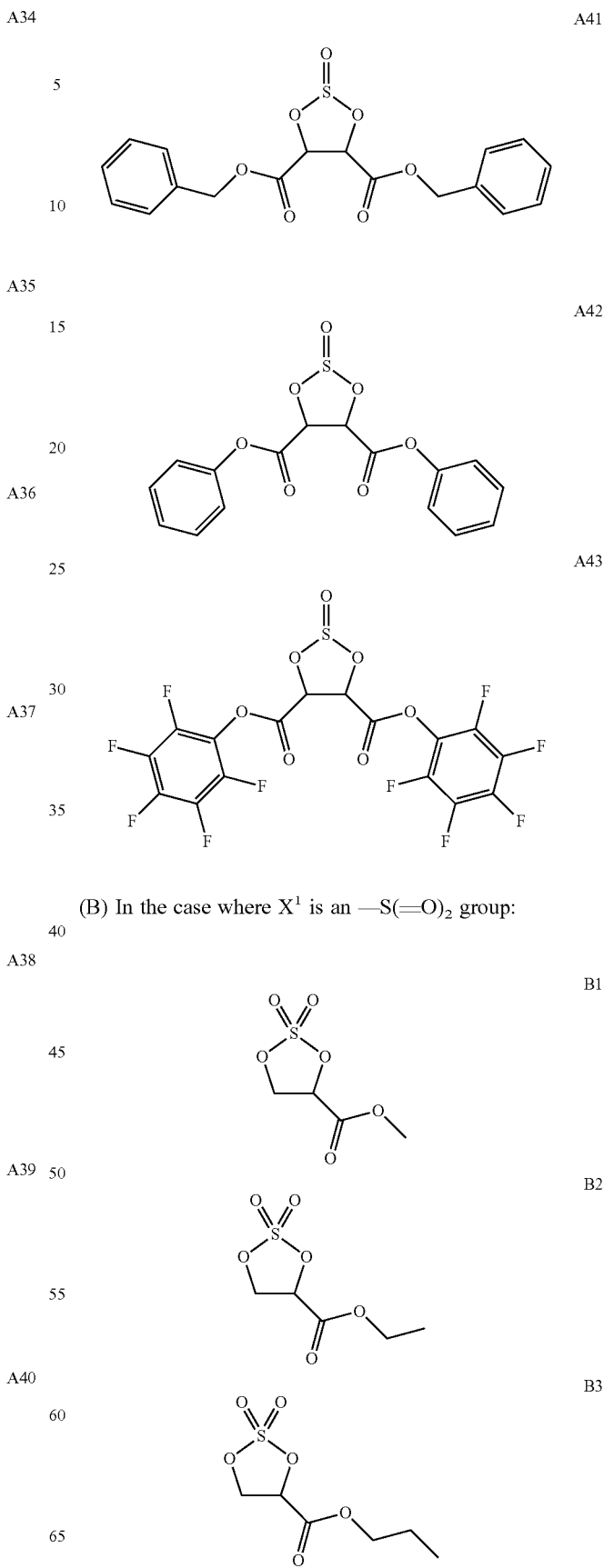
(B) In the case where $X^1$ is an $-S(=O)_2$ group:

-continued
B4
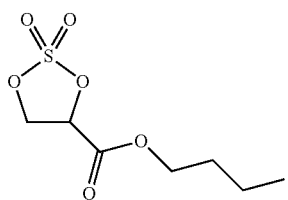
B5
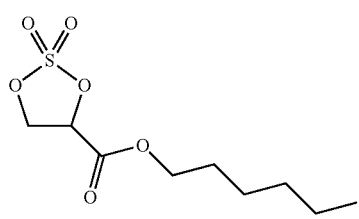
B6
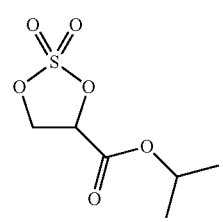
B7
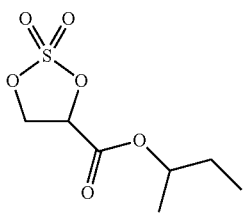
B8
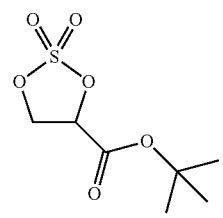
B9
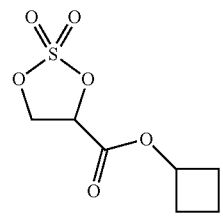
B10
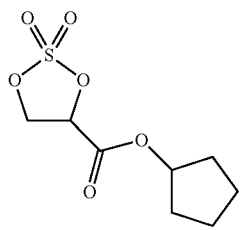
-continued
B11
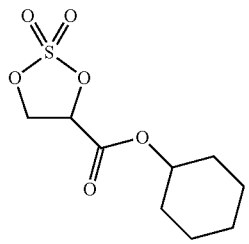
B12
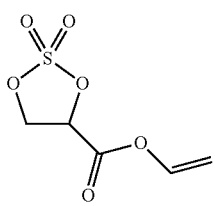
B13
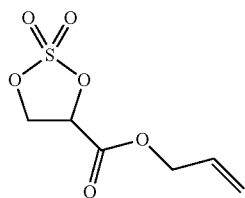
B14
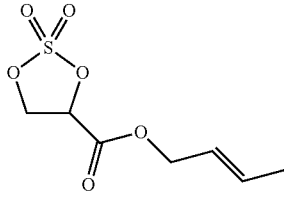
B15
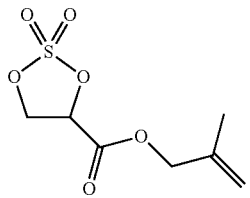
B16
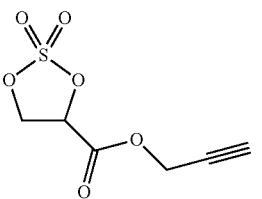
B17
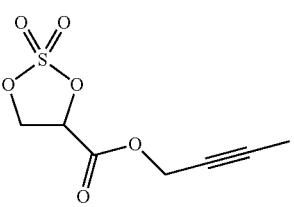

B18
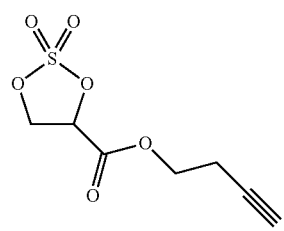
B19
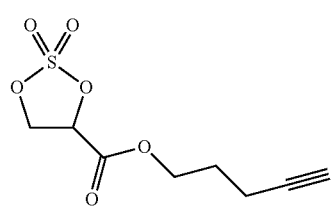
B20
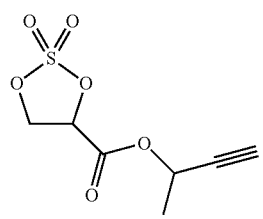
B21
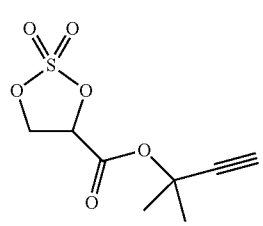
B22
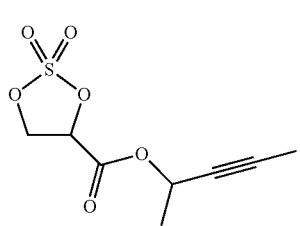
B23
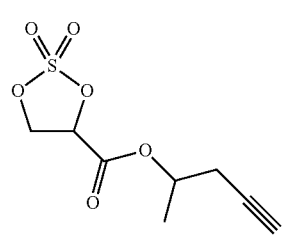
B24
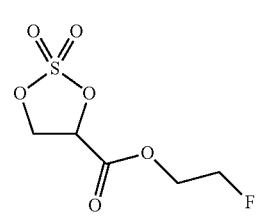
B25
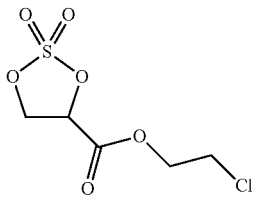
B26
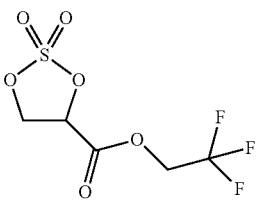
B27
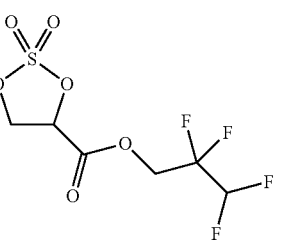
B28
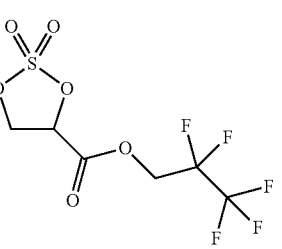
B29
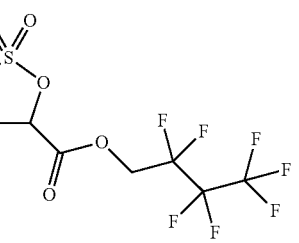
B30
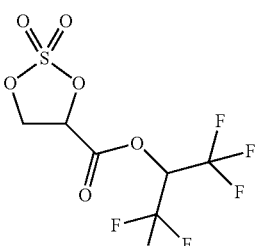
B31
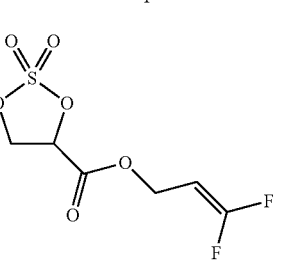

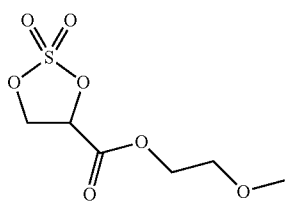 B32
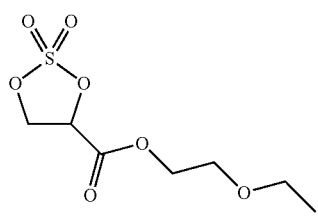 B33
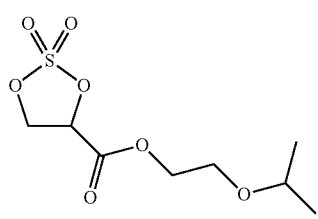 B34
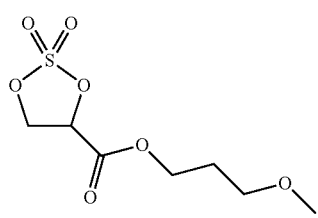 B35
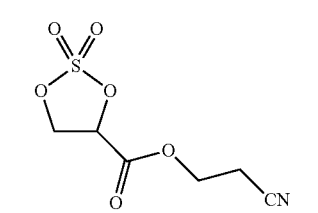 B36
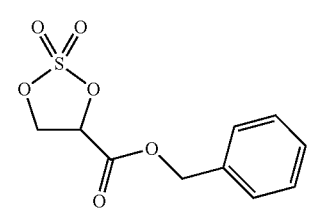 B37
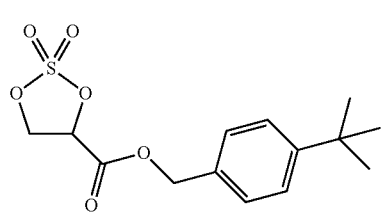 B38
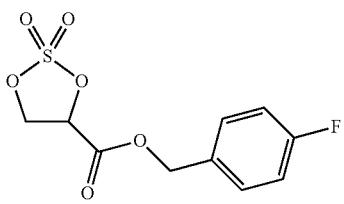 B39
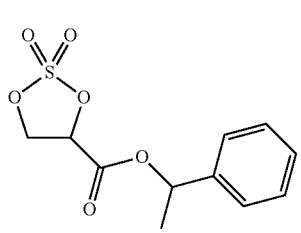 B40
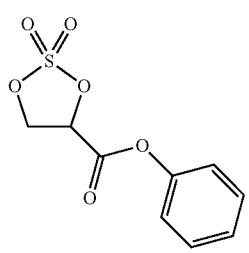 B41
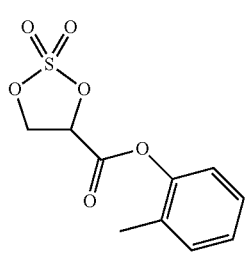 B42
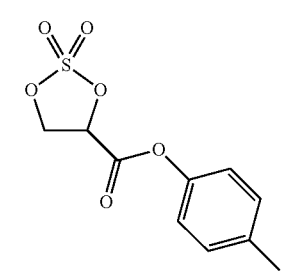 B43
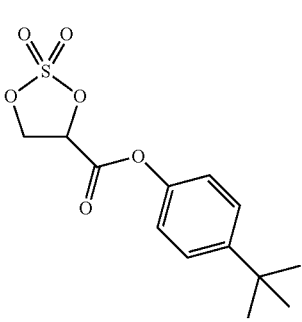 B44

B45 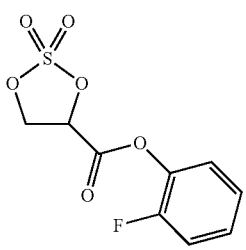
B46 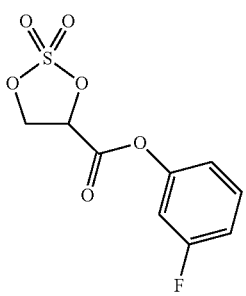
B47 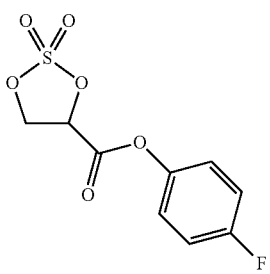
B48 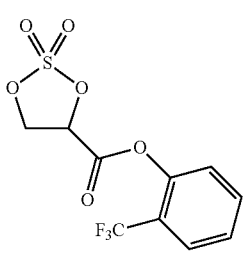
B49 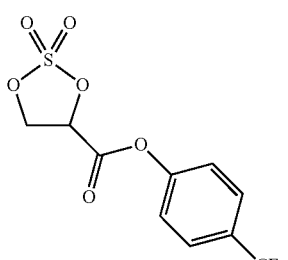
B50 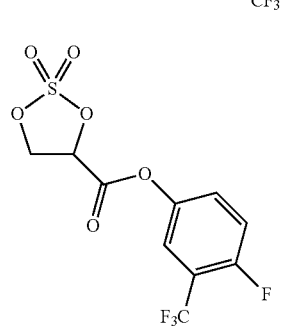
B51 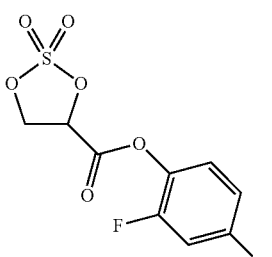
B52 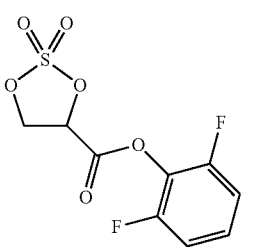
B53 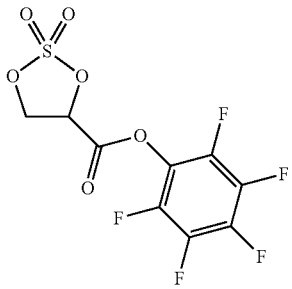
B54 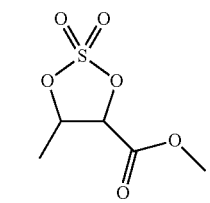
B55 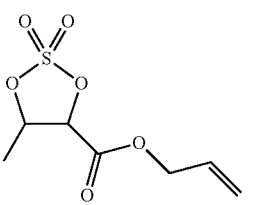
B56 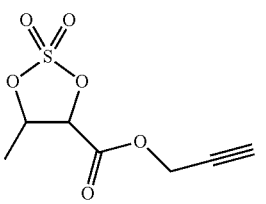
B57 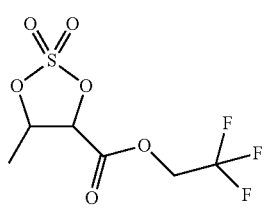

B58 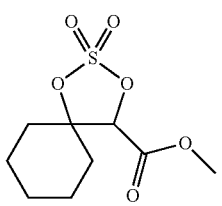
B59 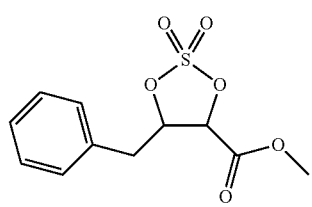
B60 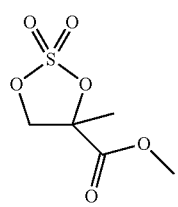
B61 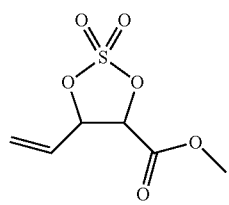
B62 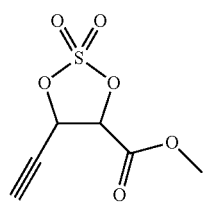
B63 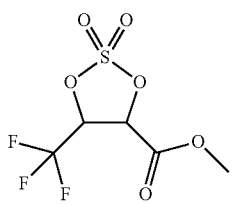
B64 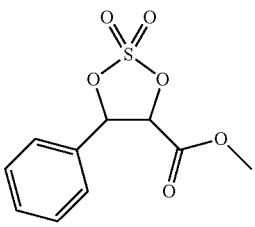
B65 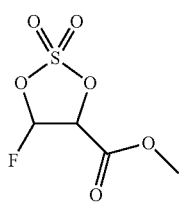
B66 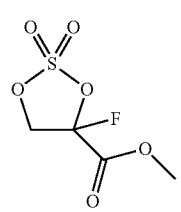
B67 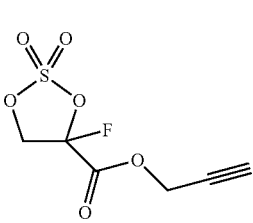
B68 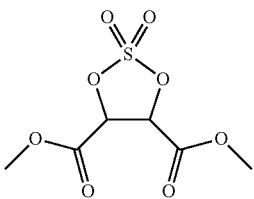
B69 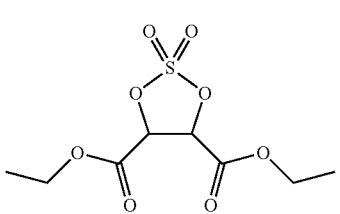
B70 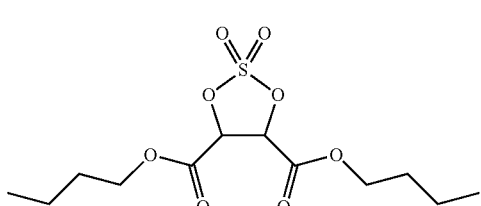
B71 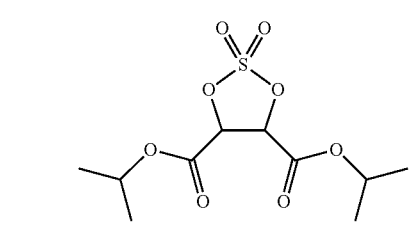

B72
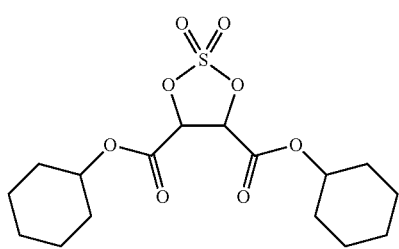
B73
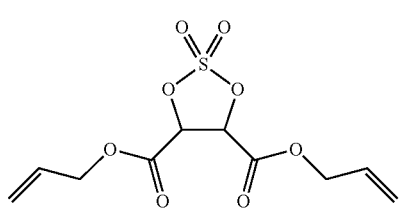
B74
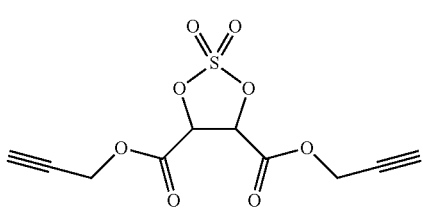
B75
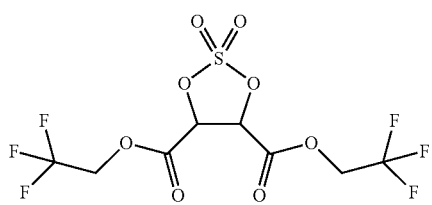
B76
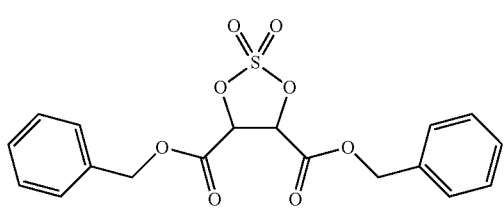
B77
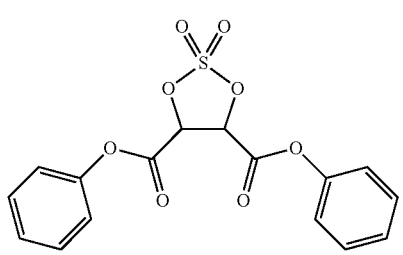
B78
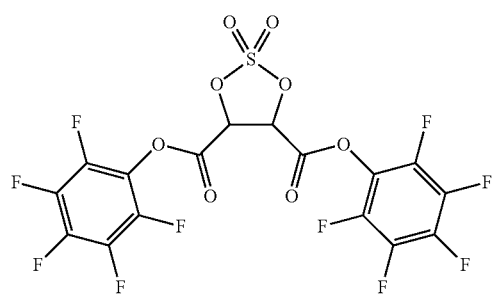
(C) In the case where $X^1$ is a —$CR^{26}R^{27}$ group:
C1
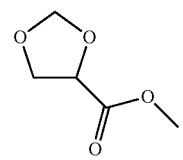
C2
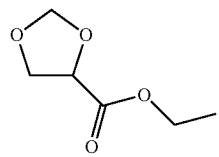
C3
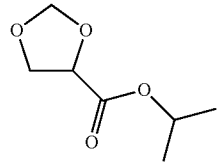
C4
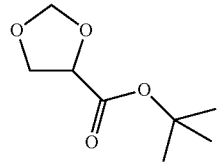
C5
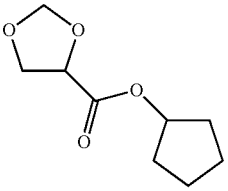
C6
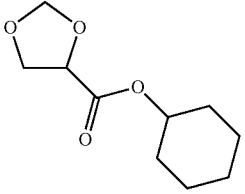

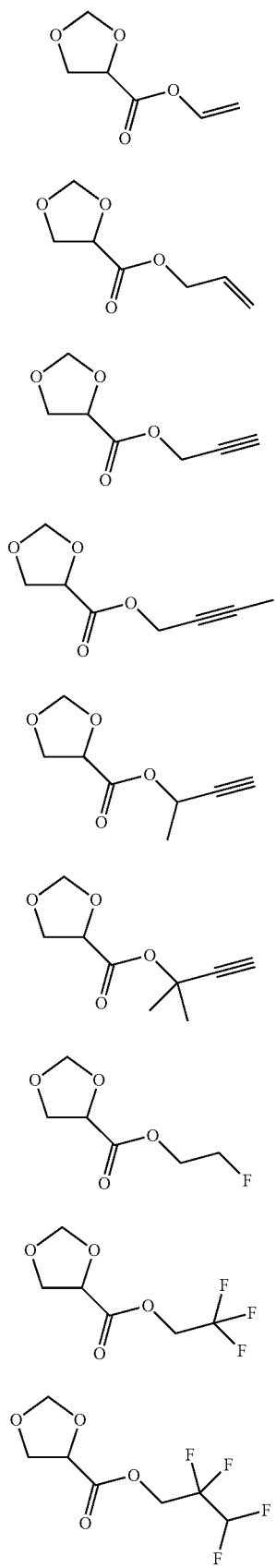
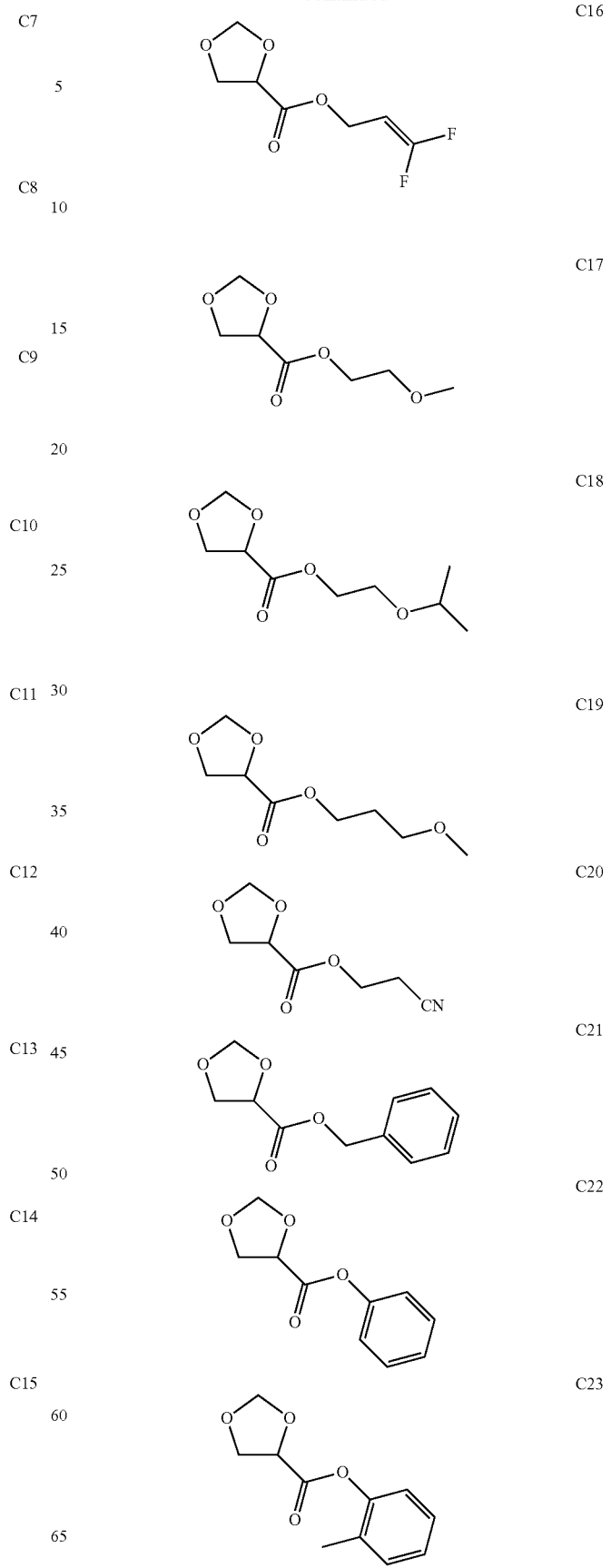

C24
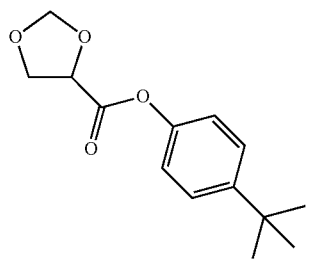
C25
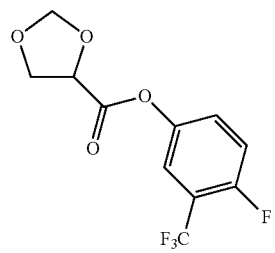
C26
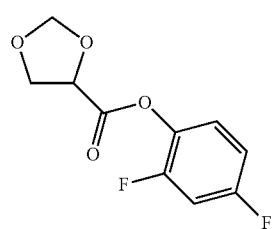
C27
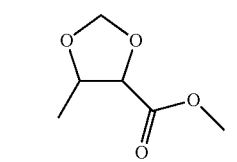
C28
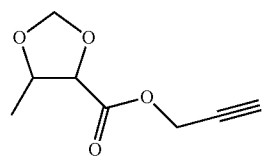
C29
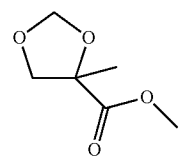
C30
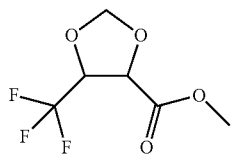
C31
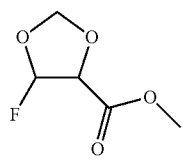
C32
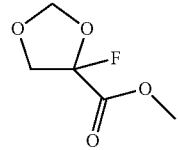
C33
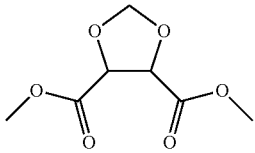
C34
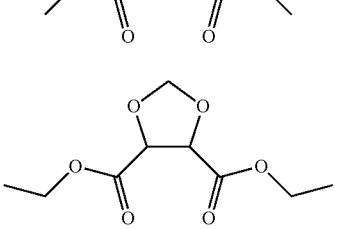
C35
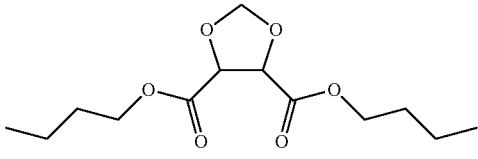
C36
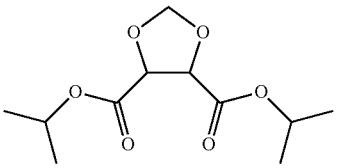
C37
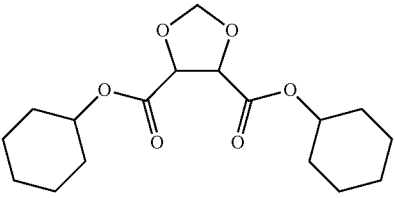
C38
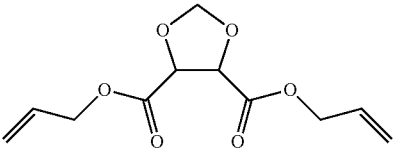
C39
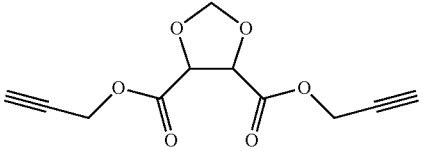
C40
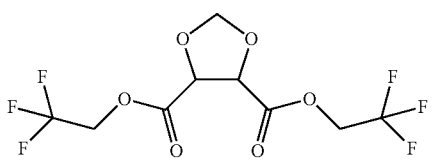

-continued

C41
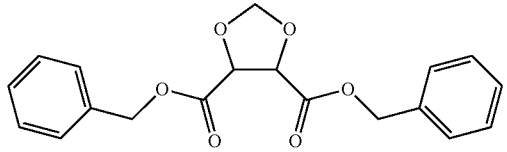

C42
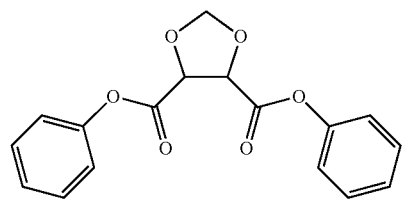

C43
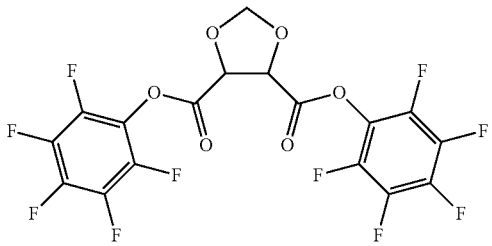

C44
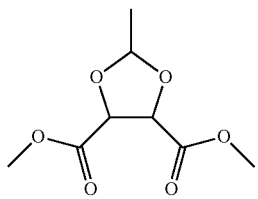

C45
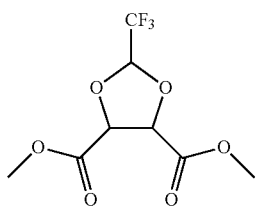

C46
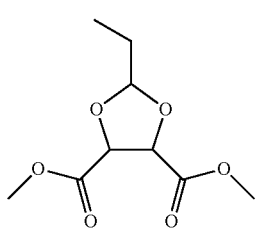

C47
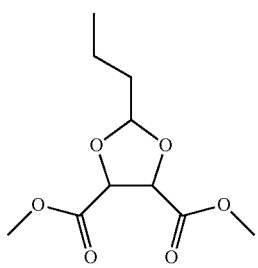

-continued

C48
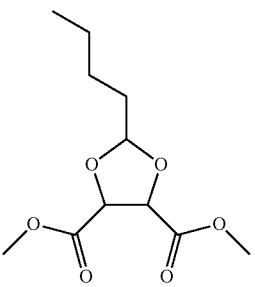

C49
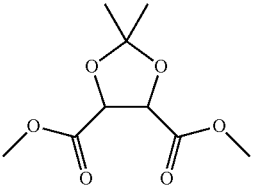

C50
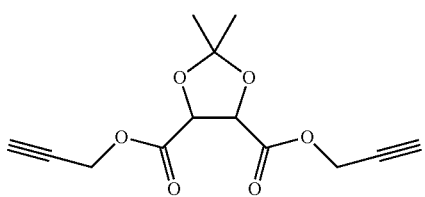

Among the aforementioned compounds, as the compound represented by the general formula (I-2), the compounds having any one of the structural formulae of A1 to A3, A7 to A17, A22 to A26, A30 to A40, A43, B1 to B4, B6, B12 to B13, B16 to B17, B20 to B22, B24, B26 to B33, B41 to B53, B63 to B78, C1 to C3, C7 to C17, C22 to C26, C30 to C46, and C49 to C50 are preferred; the compounds having any one of the structural formulae of A1 to A2, A8, A9, A14 to A15, A31 to A36, A39, A40, B1 to B2, B13, B16, B26 to B28, B65 to B70, B74 to B75, C1 to C2, C8, C9, C14, C31 to C35, C39 to C40, and C49 to C50 are more preferred; and at least one selected from methyl 1,3,2-dioxathiolane-4-carboxylate 2-oxide (structural formula A1), ethyl 1,3,2-dioxathiolane-4-carboxylate 2-oxide (structural formula A2), 2-propenyl 1,3,2-dioxathiolane-4-carboxylate 2-oxide (structural formula A8), 2-propynyl 1,3,2-dioxathiolane-4-carboxylate 2-oxide (structural formula A9), 2,2,2-trifluoro-ethyl 1,3,2-dioxathiolane-4-carboxylate 2-oxide (structural formula A14), methyl 5-fluorol-1,3,2-dioxathiolane-4-carboxylate 2-oxide (structural formula A31), dimethyl 1,3,2-dioxathiolane-4,5-dicarboxylate 2-oxide (structural formula A33), diethyl 1,3,2-dioxathiolane-4,5-dicarboxylate 2-oxide (structural formula A34), methyl 1,3,2-dioxathiolane-4-carboxylate 2,2-dioxide (structural formula B1), ethyl 1,3,2-dioxathiolane-4-carboxylate 2,2-dioxide (structural formula B2), 2-propenyl 1,3,2-dioxathiolane-4-carboxylate 2,2-dioxide (structural formula B13), 2-propynyl 1,3,2-dioxathiolane-4-carboxylate 2,2-dioxide (structural formula B16), 2,2,2-trifluoroethyl 1,3,2-dioxathiolane-4-carboxylate 2,2-dioxide (structural formula B26), methyl 5-fluoro-1,3,2-dioxathiolane-4-carboxylate 2,2-dioxide (structural formula B65), dimethyl 1,3,2-dioxathiolane-4,5-dicarboxylate 2,2-dioxide (structural formula B68), diethyl 1,3,2-dioxathiolane-4,5-dicarboxylate 2,2-dioxide (structural formula B69), methyl 1,3-dioxolane-4-carboxylate (structural formula C1), ethyl 1,3-dioxolane-4-carboxylate (structural formula C2), 2-propenyl 1,3-dioxolane-4-carboxylate (structural formula C8), 2-propynyl 1,3-dioxolane-4-carboxylate (structural formula C9), 2,2,2-trifluoroethyl 1,3-dioxolane-4-carboxylate (structural formula C14), methyl 5-fluoro-1,3-dioxolane-4-carboxylate (structural formula C31), dimethyl 1,3-dioxolane-4,5-dicarboxylate (structural formula C33), diethyl 1,3-dioxolane-4,5-dicarboxylate (structural formula C34), and dimethyl 2,2-dimethyl-1,3-dioxolane-4,5-dicarboxylate (structural formula C49) is especially preferred.

In the nonaqueous electrolytic solution of the present invention, a content of the carboxylic acid ester compound represented by the general formula (I-2) is preferably 0.001 to 10% by mass in the nonaqueous electrolytic solution. So long as the content is 10% by mass or less, there is less concern that a surface film is excessively formed on an electrode, so that in the case of using a battery at a high temperature and at a high voltage, the storage characteristics are worsened. So long as the content is 0.001% by mass or more, the formation of a surface film is sufficient, and in the case of using a battery at a high temperature and at a high voltage, an improving effect of the storage characteristics is enhanced. The content is preferably 0.05% by mass or more, and more preferably 0.3% by mass or more in the nonaqueous electrolytic solution. An upper limit thereof is preferably 8% by mass or less, more preferably 5% by mass or less, and especially preferably 3% by mass or less.

[Nonaqueous Electrolytic Solution of Embodiment 3]

According to the nonaqueous electrolytic solution of Embodiment 3 of the present invention, in the nonaqueous electrolytic solution having an electrolyte salt dissolved in a nonaqueous solvent, the compound represented by the foregoing general formula (I) wherein X is an —S(=O)$_2$—R$^5$—S(=O)$_2$— group, and n is 1 or 2, more specifically the carboxylic acid ester compound represented by the foregoing general formula (I-3) is contained in the nonaqueous electrolytic solution.

Although the reasons why the nonaqueous electrolytic solution of Embodiment 3 is able to greatly improve the electrochemical characteristics of an energy storage device when used at a high temperature and at a high voltage are not always elucidated yet, the following may be considered.

In view of the fact that the compound represented by the general formula (I-3), which is used in Embodiment 3, has a hetero ring which is reductively decomposed at the α-position of the carbonyl group to form a surface film, it has high reactivity and quickly reacts with active sites of both a positive electrode and a negative electrode, thereby forming a firmer surface film. Therefore, it may be considered that not only the storage characteristics at a high temperature and at a high voltage are improved, but also the gas generation to be caused due to decomposition of the solvent is inhibited.

The carboxylic acid ester compound which is contained in the nonaqueous electrolytic solution of Embodiment 3 is represented by the following general formula (I-3).

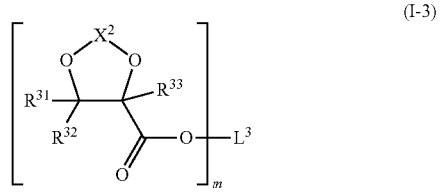

(I-3)

In the formula, each of R$^{31}$ and R$^{32}$ independently represents a hydrogen atom, a halogen atom, an alkyl group having 1 to 6 carbon atoms, in which at least one hydrogen atom may be substituted with a halogen atom, an aryl group having 6 to 12 carbon atoms, in which at least one hydrogen atom may be substituted with a halogen atom, or a —C(=O)—OR$^{34}$ group. R$^{33}$ represents a hydrogen atom, a halogen atom, or an alkyl group having 1 to 6 carbon atoms, and m represents 1 or 2.

When m is 1, then L$^3$ and R$^{34}$ may be the same as or different from each other and represent an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, in which at least one hydrogen atom may be substituted with a halogen atom, or an aryl group having 6 to 12 carbon atoms, in which at least one hydrogen atom may be substituted with a halogen atom, and when m is 2, then L$^3$ represents an alkylene group having 2 to 8 carbon atoms, an alkenylene group having 4 to 8 carbon atoms, or an alkynylene group having 4 to 8 carbon atoms, at least one hydrogen atom of L$^3$ may be substituted with a halogen atom, and R$^{34}$ is the same as described above.

X$^2$ represents an —S(=O)$_2$—R$^{35}$—S(=O)$_2$— group, and R$^{35}$ represents an alkylene group having 1 to 4 carbon atoms, in which at least one hydrogen atom may be substituted with a halogen atom or an alkyl group having 1 to 4 carbon atoms.

In the foregoing general formula (I-3), each of R$^{31}$ and R$^{32}$ is independently preferably a hydrogen atom, a halogen atom, an alkyl group having 1 to 6 carbon atoms, in which at least one hydrogen atom may be substituted with a halogen atom, or a —C(=O)—OR$^{34}$ group, and more preferably a hydrogen atom, a halogen atom, an alkyl group having 1 to 4 carbon atoms, in which at least one hydrogen atom may be substituted with a halogen atom, or a —C(=O)—OR$^{34}$ group.

R$^{33}$ is preferably a hydrogen atom or a halogen atom, and more preferably a hydrogen atom. m represents 1 or 2, and preferably 1. When m is 1, then L$^3$ and R$^{34}$ may be the same as or different from each other and are preferably an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, or an aryl group having 6 to 12 carbon atoms, in which at least one hydrogen atom may be substituted with a halogen atom, and more preferably an alkenyl group having 2 to 6 carbon atoms or an alkynyl group having 3 to 6 carbon atoms. When m is 2, then L$^3$ is preferably an alkylene group having 2 to 6 carbon atoms, an alkenylene group having 4 to 8 carbon atoms, or an alkynylene group having 4 to 8 carbon atoms, and more preferably an alkylene group having 2 to 4 carbon atoms, an alkenylene group having 4 to 6 carbon atoms, or an alkynylene group having 4 to 6 carbon atoms.

R$^{35}$ is preferably an alkylene group having 1 to 2 carbon atoms, in which at least one hydrogen atom may be substituted with a fluorine atom or a methyl group, and more preferably a methylene group.

As specific examples of $R^{31}$ and $R^{32}$, there are suitably exemplified a hydrogen atom; a halogen atom, such as a fluorine atom, a chlorine atom, a bromine atom, etc.; a straight-chain alkyl group, such as a methyl group, an ethyl group, an n-propyl group, an n-butyl group, an n-pentyl group, an n-hexyl group, etc.; a branched alkyl group, such as an isopropyl group, a sec-butyl group, a 2-pentyl group, a 3-pentyl group, a tert-butyl group, a tert-amyl group, etc.; a halogenated alkyl group, such as a fluoromethyl group, a difluoromethyl group, a trifluoromethyl group, a 2-chloroethyl group, a 2-fluoroethyl group, a 2,2-difluoroethyl group, a 2,2,2-trifluoroethyl group, a 3-fluoropropyl group, a 3-chloropropyl group, a 3,3-difluoropropyl group, a 3,3,3-trifluoropropyl group, a 2,2,3,3-tetrafluoropropyl group, a 2,2,3,3,3-pentafluoropropyl group, etc.; and an aryl group, such as a phenyl group, a 2-methylphenyl group, a 3-methylphenyl group, a 4-methylphenyl group, a 4-tert-butylphenyl group, a 2-fluorophenyl group, a 4-fluorophenyl group, a 2-trifluoromethylphenyl group, a 3-trifluoromethylphenyl group, a 4-trifluoromethylphenyl group, a 4-fluoro-2-trifluoromethylphenyl group, a 4-fluoro-3-trifluoromethylphenyl group, a 2,6-difluorophenyl group, a 3,5-difluorophenyl group, a 2,4,6-trifluorophenyl group, a 2,3,5,6-tetrafluorophenyl group, a perfluorophenyl group, etc.; and also a methoxycarbonyl group, an ethoxycarbonyl group, a 2,2,2-trifluoroethoxycarbonyl group, a 2,2,3,3-tetrafluoropropoxycarbonyl group, a cyclopentyloxycarbonyl group, a cyclohexyloxycarbonyl group, a vinyloxycarbonyl group, a 1-propen-1-yloxycarbonyl group, a 2-propen-1-yloxycarbonyl group, a 2-propynyloxycarbonyl group, a 1-methyl-2-propynyloxycarbonyl group, a benzyloxycarbonyl group, a phenyloxycarbonyl group, a 4-fluorophenyloxycarbonyl group, a 2-trifluoromethylphenyloxycarbonyl group, a 4-fluoro-3-trifluoromethylphenyloxycarbonyl group, a 2,3,5,6-tetrafluorophenyloxycarbonyl group, a perfluorophenyloxycarbonyl group, and the like.

Of the foregoing, $R^{31}$ and $R^{32}$ are preferably a hydrogen atom, a fluorine atom, a chlorine atom, a methyl group, an ethyl group, an n-propyl group, an n-butyl group, an n-pentyl group, an n-hexyl group, an isopropyl group, a sec-butyl group, a tert-butyl group, a trifluoromethyl group, a 2,2,2-trifluoroethyl group, a 2,2,3,3-tetrafluoropropyl group, a methoxycarbonyl group, an ethoxycarbonyl group, a 2,2,2-trifluoroethoxycarbonyl group, a 2,2,3,3-tetrafluoropropoxycarbonyl group, a vinyloxycarbonyl group, a 1-propen-1-yloxycarbonyl group, a 2-propen-1-yloxycarbonyl group, a 2-propynyloxycarbonyl group, a 1-methyl-2-propynyloxycarbonyl group, a phenyloxycarbonyl group, a 2-trifluoromethylphenyloxycarbonyl group, a 4-fluoro-3-trifluoromethylphenyloxycarbonyl group, a 2,3,5,6-tetrafluorophenyloxycarbonyl group, or a perfluorophenyloxycarbonyl group; and more preferably a hydrogen atom, a fluorine atom, a methyl group, an ethyl group, a trifluoromethyl group, a 2-propen-1-yloxycarbonyl group, or a 2-propynyloxycarbonyl group.

As specific examples of $R^{33}$, there are suitably exemplified a hydrogen atom; a halogen atom, such as a fluorine atom, a chlorine atom, a bromine atom, etc.; a straight-chain alkyl group, such as a methyl group, an ethyl group, an n-propyl group, an n-butyl group, an n-pentyl group, an n-hexyl group, etc.; and a branched alkyl group, such as an isopropyl group, a sec-butyl group, a 2-pentyl group, a pentan-3-yl group, a tert-butyl group, a tert-amyl group, etc. Above all, a hydrogen atom, a fluorine atom, a chlorine atom, a methyl group, an ethyl group, an n-propyl group, an n-butyl group, an isopropyl group, a sec-butyl group, or a tert-butyl group is preferred, with a hydrogen atom, a fluorine atom, a methyl group, or an ethyl group being more preferred.

As specific examples of $L^3$, there are suitably exemplified the following groups.

(i) In the case of m=1:

There are suitably exemplified a straight-chain alkyl group, such as a methyl group, an ethyl group, an n-propyl group, an n-butyl group, an n-pentyl group, an n-hexyl group, etc.; a branched alkyl group, such as an isopropyl group, a sec-butyl group, a 2-pentyl group, a 3-pentyl group, a tert-butyl group, a tert-amyl group, etc.; a halogenated alkyl group, such as a fluoromethyl group, a difluoromethyl group, a 2-chloroethyl group, a 2-fluoroethyl group, a 2,2-difluoroethyl group, a 2,2,2-trifluoroethyl group, a 3-fluoropropyl group, a 3-chloropropyl group, a 3,3-difluoropropyl group, a 3,3,3-trifluoropropyl group, a 2,2,3,3-tetrafluoropropyl group, a 2,2,3,3,3-pentafluoropropyl group, etc.; a cycloalkyl group, such as a cyclopropyl group, a cyclobutyl group, a cyclopentyl group, a cyclohexyl group, a cycloheptyl group, etc.; a halogenated cycloalkyl group, such as a 4-fluorocyclohexyl group, a 4-chlorocyclohexyl group, etc.; an alkenyl group, such as a vinyl group, a 1-propen-1-yl group, a 2-propen-1-yl group, a 2-buten-1-yl group, a 3-buten-1-yl group, a 4-penten-1-yl group, a 5-hexen-1-yl group, a 1-propen-2-yl group, a 1-buten-2-yl group, a 2-methyl-2-propen-1-yl group, etc.; a haloalkenyl group, such as a 3,3-difluoro-2-propen-1-yl group, a 4,4-difluoro-3-buten-1-yl group, a 3,3-dichloro-2-propen-1-yl group, a 4,4-dichloro-3-buten-1-yl group, etc.; an alkynyl group, such as a 2-propynyl group, a 2-butynyl group, a 3-butynyl group, a 4-heptynyl group, a 1-methyl-2-propynyl group, a 1,1-dimethyl-2-propynyl group, a 1-methyl-3-butynyl group, a 1-methyl-4-heptynyl group, etc.; an alkoxyalkyl group, such as a methoxymethyl group, an ethoxymethyl group, a methoxyethyl group, an ethoxyethyl group, an n-propoxyethyl group, an n-butoxyethyl group, a methoxypropyl group, an ethoxypropyl group, etc.; a cyanoalkyl group, such as a cyanomethyl group, a 2-cyanoethyl group, a 3-cyanopropyl group, a 4-cyanobutyl group. etc.; an aralkyl group, such as a benzyl group, a 4-methylbenzyl group, a 4-tert-butylbenzyl group, a 4-fluorobenzyl group, a 4-chlorobenzyl group, a 1-phenylethan-1-yl group, a 2-phenylethan-1-yl group, a 3-phenylpropan-1-yl group, etc.; an aryl group, such as a phenyl group, a 2-methylphenyl group, a 3-methylphenyl group, a 4-methylphenyl group, a 4-tert-butylphenyl group, a 2-fluorophenyl group, a 4-fluorophenyl group, a 2-trifluoromethylphenyl group, a 3-trifluoromethylphenyl group, a 4-trifluoromethylphenyl group, a 4-fluoro-2-trifluoromethylphenyl group, a 4-fluoro-3-trifluoromethylphenyl group, a 2,6-difluorophenyl group, a 3,5-difluorophenyl group, a 2,4,6-trifluorophenyl group, a 2,3,5,6-tetrafluorophenyl group, a perfluorophenyl group, etc.; and the like.

In the case of m=1, of the foregoing, $L^3$ is preferably a methyl group, an ethyl group, an n-propyl group, an n-butyl group, an isopropyl group, a sec-butyl group, a 2,2,2-trifluoroethyl group, a 2,2,3,3-tetrafluoropropyl group, a cyclopropyl group, a cyclobutyl group, a cyclopentyl group, a cyclohexyl group, a vinyl group, a 1-propen-1-yl group, a 2-propen-1-yl group, a 2-buten-1-yl group, a 3-buten-1-yl group, a 1-propen-2-yl group, a 1-buten-2-yl group, a 2-methyl-2-propen-1-yl group, a 3,3-difluoro-2-propen-1-yl group, a 4,4-difluoro-3-buten-1-yl group, a 3,3-dichloro-2-propen-1-yl group, a 4,4-dichloro-3-buten-1-yl group, a 2-propynyl group, a 2-butynyl group, a 3-butynyl group, a 1-methyl-2-propynyl group, a 1,1-dimethyl-2-propynyl group, a 2,3,5,6-tetrafluorophenyl group, or a perfluorophenyl group; and more preferably a methyl group, an ethyl group, a 2,2,2-trifluoroethyl group, a 2,2,3,3-tetrafluoropropyl group, a 2-propen-1-yl group, a 2-propynyl group, a 2-butynyl group, or a 1-methyl-2-propynyl group.

(ii) In the case of m=2:

There are suitably exemplified a straight-chain alkylene group, such as an ethylene group, a propane-1,3-diyl group, a butane-1,4-diyl group, a pentane-1,5-diyl group, a hexane-1,6-diyl group, etc.; a branched alkylene group, such as a propane-1,2-diyl group, a butane-1,3-diyl group, a butane-2,3-diyl group, a 2-methylpropane-1,2-diyl group, a 2,2-dimethylpropane-1,3-thyl group, etc.; a haloalkylene group, such as a 2,2-difluoropropane-1,3-diyl group, a 2,2,3,3-tetrafluorobutane-1,4-diyl group, a 2,2,3,3,4,4-hexafluoropentane-1,5-diyl group, a 2,2,3,3,4,4,5,5-octafluorohexane-1,6-diyl group, a 2,2-dichloropropane-1,3-diyl group, a 2,2,3,3-tetrachlorobutene-1,4-diyl group, etc.; an alkenylene group, such as a 2-butene-1,4-diyl group, a 2-pentene-1,5-diyl group, a 3-hexene-1,6-diyl group, a 3-hexene-2,5-diyl group, a 2,5-dimethyl-3-hexene-2,5-diyl group, etc.; and an alkynylene group, such as a 2-butyne-1,4-diyl group, a 2-pentyne-1,5-diyl group, a 3-hexyne-1,6-diyl group, a 3-hexyne-2,5-diyl group, a 2,5-dimethyl-3-hexyne-2,5-diyl group, etc.

In the case of m=2, of the foregoing, $L^3$ is preferably an ethylene group, a propane-1,3-diyl group, a butane-1,4-diyl group, a pentane-1,5-diyl group, a hexane-1,6-diyl group, a propane-1,2-diyl group, a butane-2,3-diyl group, a 2,2-dimethylpropane-1,3-diyl group, a 2-butene-1,4-diyl group, a 3-hexene-2,5-diyl group, a 2-butyne-1,4-diyl group, or a 3-hexyne-2,5-diyl group; and more preferably a 2-buten-1,4-diyl group or a 2-butyne-1,4-diyl group.

As specific examples of $X^2$, there are suitably exemplified a bis(sulfonyl)methyl group, a 1,1-bis(sulfonyl)ethyl group, a 1,1-bis(sulfonyl)propyl group, a 1,1-bis(sulfonyl)butyl group, a 2,2-bis(sulfonyl)propyl group, a 2,2-bis(sulfonyl)butyl group, a 3,3-bis(sulfonyl)pentyl group, a bis(sulfonyl)fluoromethyl group, a bis(sulfonyl)difluoromethyl group, a 1,2-bis(sulfonyl)ethyl group, a 1,2-bis(sulfonyl)propyl group, a 2,3-bis(sulfonyl)butyl group, a 1,3-bis(sulfonyl)propyl group, and a 1,4-bis(sulfonyl)butyl group. Among those, a bis(sulfonyl)methyl group, a 1,1-bis(sulfonyl)ethyl group, a bis(sulfonyl)fluoromethyl group, or a 1,2-bis(sulfonyl)ethyl group is preferred, with a bis(sulfonyl)methyl group being more preferred.

As the carboxylic acid ester compound represented by the foregoing general formula (I-3), specifically, there are suitably exemplified the following compounds.

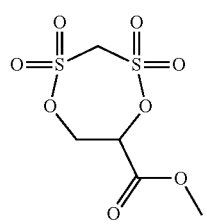
D1

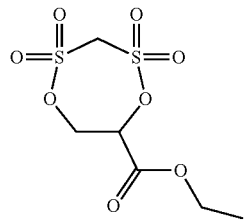
D2

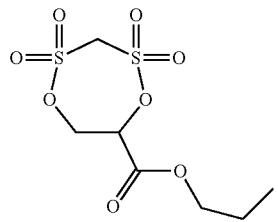
D3

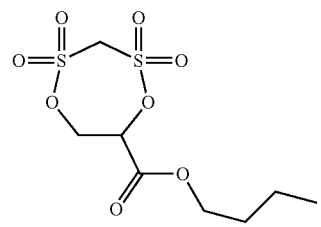
D4

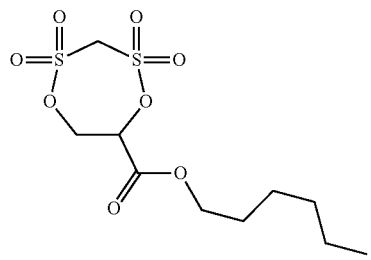
D5

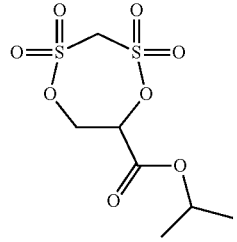
D6

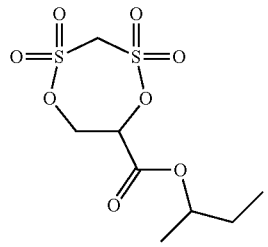
D7

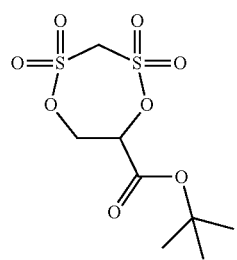
D8
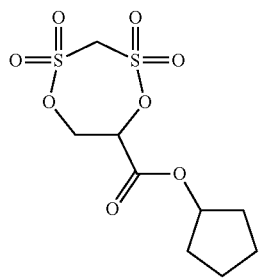
D9
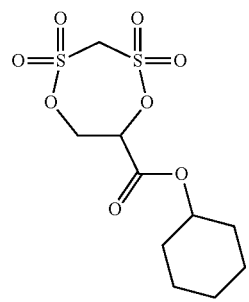
D10
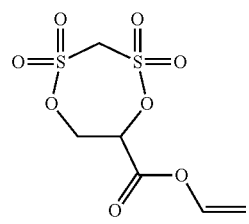
D11
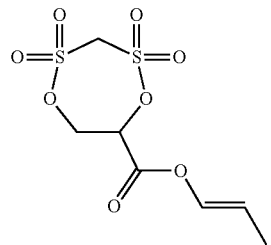
D12
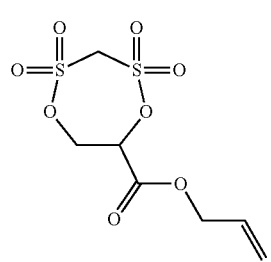
D13
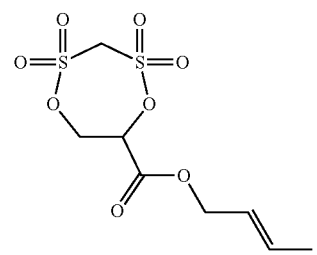
D14
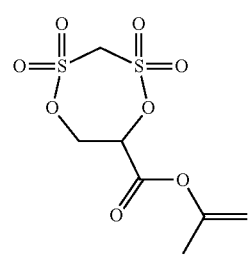
D15
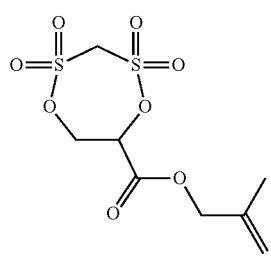
D16
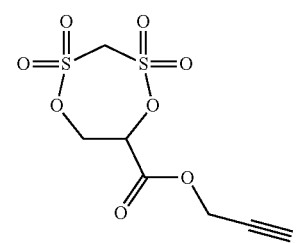
D17
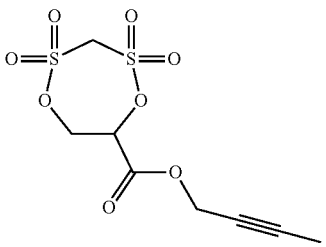
D18
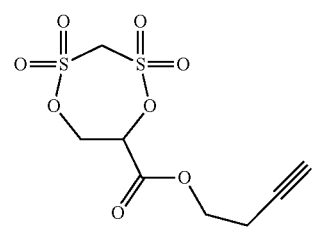
D19

-continued
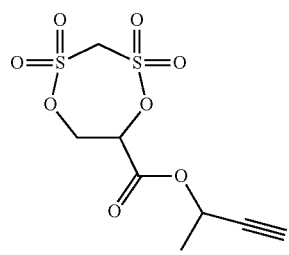
D20
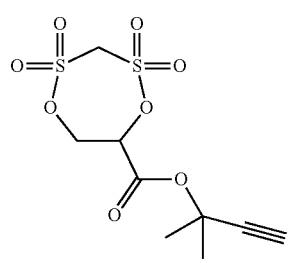
D21
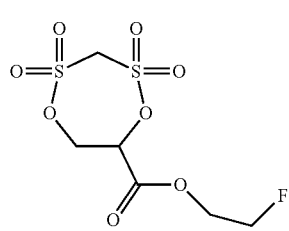
D22
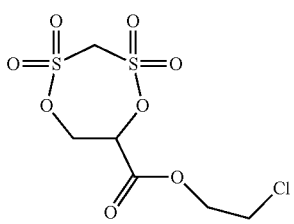
D23
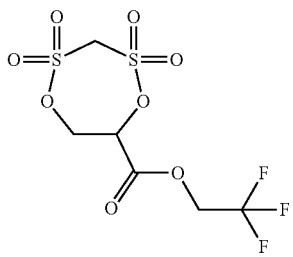
D24
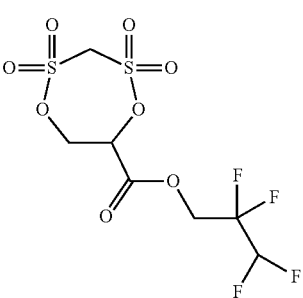
D25
-continued
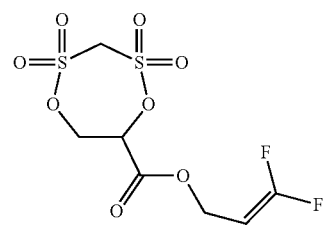
D26
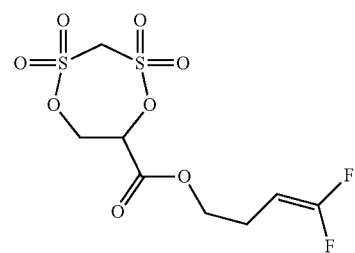
D27
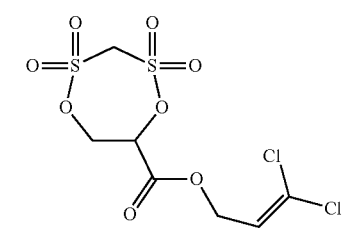
D28
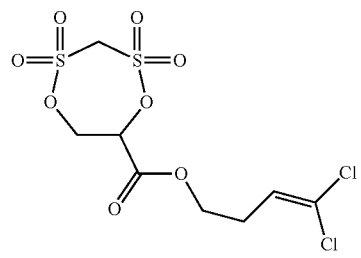
D29
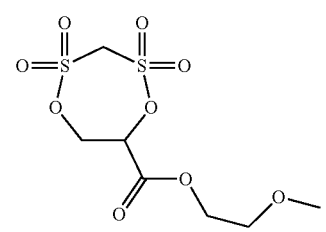
D30
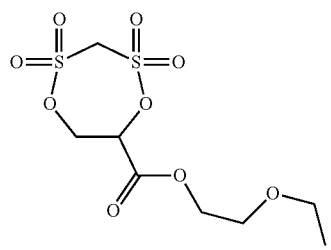
D31

-continued
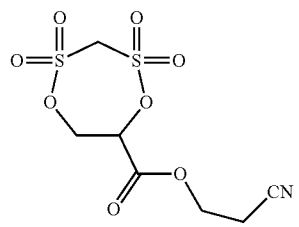
D32
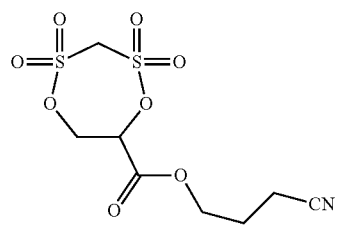
D33
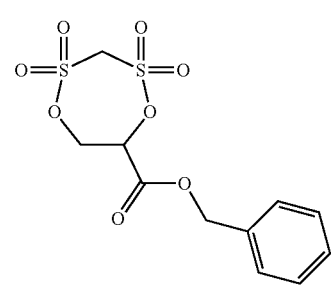
D34
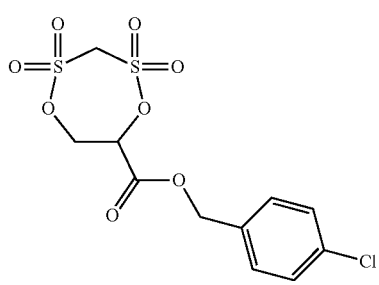
D35
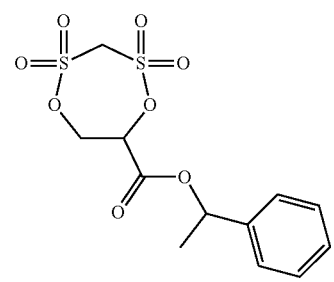
D36
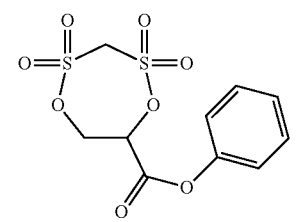
D37
-continued
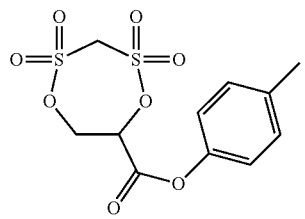
D38
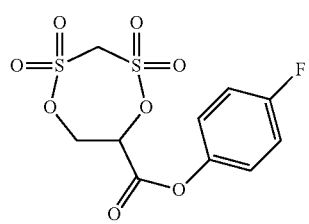
D39
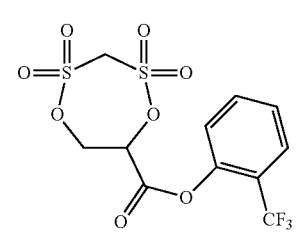
D40
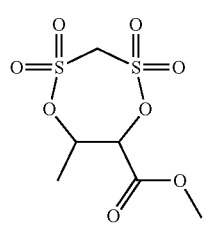
D41
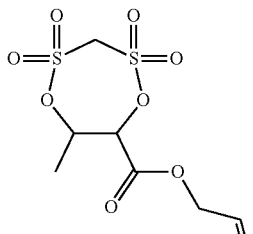
D42
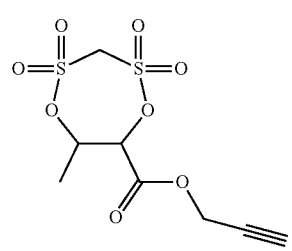
D43

-continued
D44 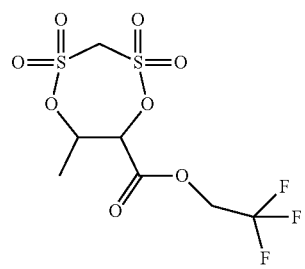
D45 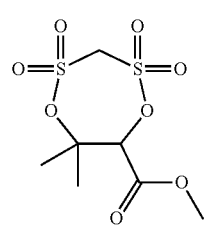
D46 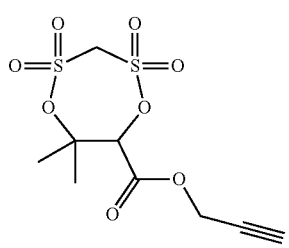
D47 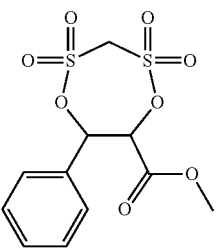
D48 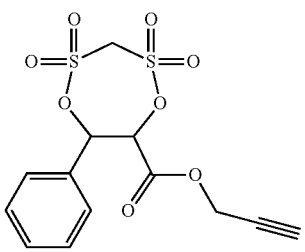
D49 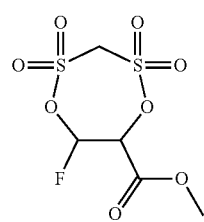
D50 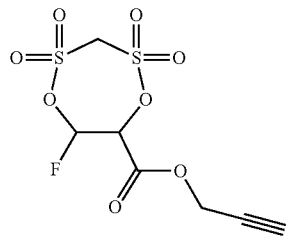
D51 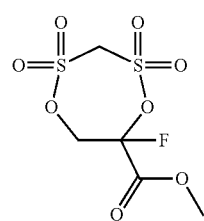
D52 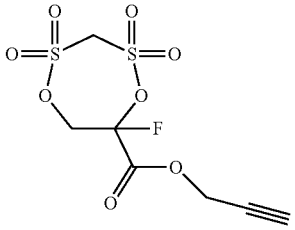
D53 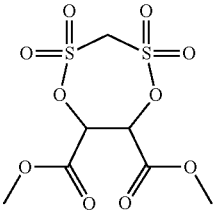
D54 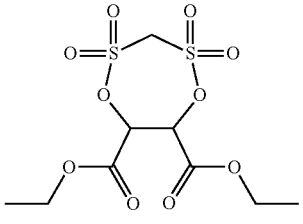
D55 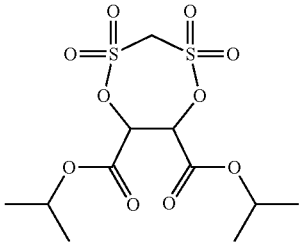

-continued
D56
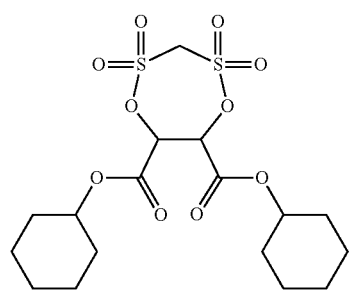
D57
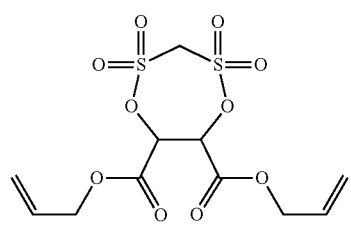
D58
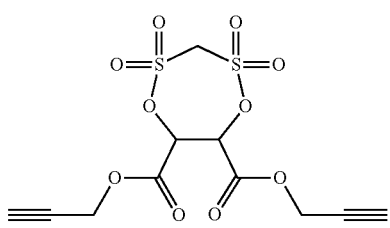
D59
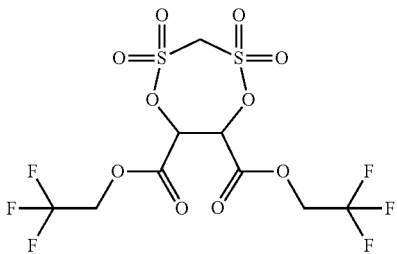
D60
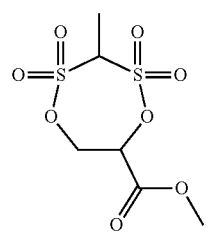
D61
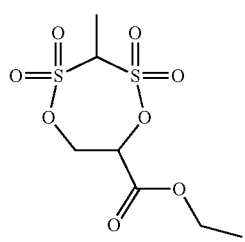
-continued
D62
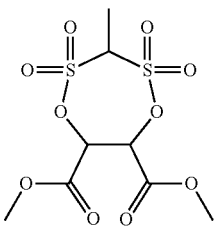
D63
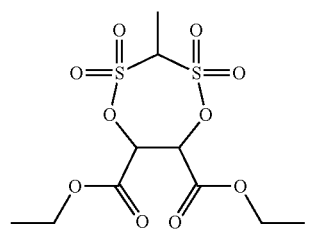
D64
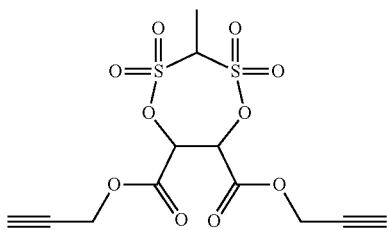
D65
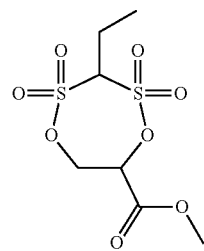
D66
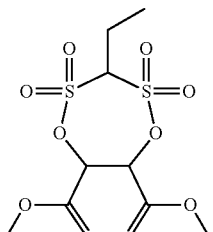
D67
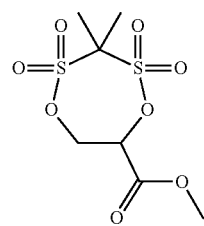

-continued

D68 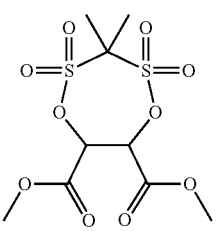

D69 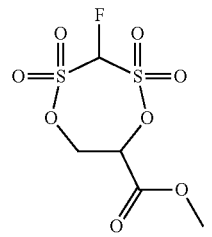

D70 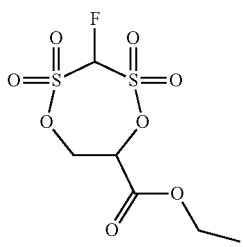

D71 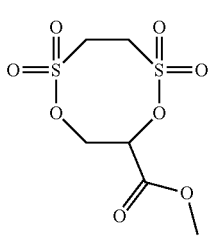

D72 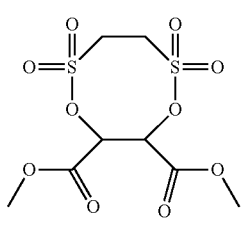

D73 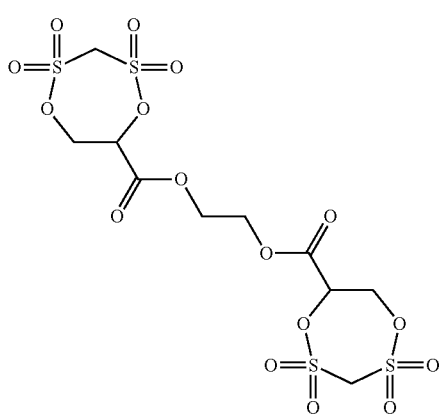

-continued

D74 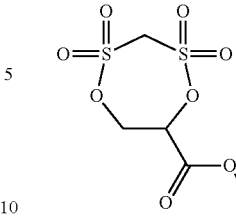

D75 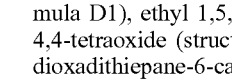

Among the aforementioned compounds, as the compound represented by the general formula (I-3), the compounds having any one of the structural formulae of D1 to D4, D6, D11 to D13, D17, D18, D20 to D22, D24 to D26, D30, D31, D37 to D40, D49 to D64, and D73 to D75 are more preferred; the compounds having any one of the structural formulae of D1, D2, D13, D17, D24, D25, D49 to D55, D58, and D59 are still more preferred; and methyl 1,5,2,4-dioxadithiepane-6-carboxylate 2,2,4,4-tetraoxide (structural formula D1), ethyl 1,5,2,4-dioxadithiepane-6-carboxylate 2,2,4,4-tetraoxide (structural formula D2), 2-propenyl 1,5,2,4-dioxadithiepane-6-carboxylate 2,2,4,4-tetraoxide (structural formula D13), 2-propynyl 1,5,2,4-dioxadithiepane-6-carboxylate 2,2,4,4-tetraoxide (structural formula D17), 2,2,2-trifluoroethyl 1,5,2,4-dioxadithiepane-6-carboxylate 2,2,4,4-tetraoxide (structural formula D24), methyl 1,5,2,4-dioxadithiepane-7-fluoro-6-carboxylate 2,2,4,4-tetraoxide (structural formula D49), dimethyl 1,5,2,4-dioxadithiepane-6,7-dicarboxylate 2,2,4,4-tetraoxide (structural formula D53), and diethyl 1,5,2,4-dioxadithiepane-6,7-dicarboxylate 2,2,4,4-tetraoxide (structural formula D54) are especially preferred.

In the nonaqueous electrolytic solution of the present invention, a content of the carboxylic acid ester compound represented by the foregoing general formula (I-3) is preferably 0.001 to 10% by mass in the nonaqueous electrolytic solution. So long as the content is 10% by mass or less, there is less concern that a surface film is excessively formed on an electrode, so that in the case of using a battery at a high temperature and at a high voltage, the storage characteristics are worsened. So long as the content is 0.001% by mass or more, the formation of a surface film is sufficient, and in the case of using a battery at a high temperature and at a high voltage, an improving effect of the storage characteristics is enhanced. The content is preferably 0.01% by mass or more, and more preferably 0.3% by mass or more in the nonaqueous electrolytic solution. An upper limit thereof is preferably 8% by mass or less, more preferably 7% by mass or less, and especially preferably 5% by mass or less.

[Nonaqueous Solvent]

As the nonaqueous solvent which is used for the nonaqueous electrolytic solution of the present invention, there are suitably exemplified one or more selected from cyclic carbonates, linear esters, lactones, ethers, and amides. In order that the electrochemical characteristics may be synergistically improved at a high temperature, it is preferred to include a linear ester, it is more preferred to include a linear carbonate, and it is most preferred to include both a cyclic carbonate and a linear carbonate.

The term "linear ester" is used as a concept including a linear carbonate and a linear carboxylic acid ester.

As the cyclic carbonate, there is exemplified one or more selected from ethylene carbonate (EC), propylene carbonate (PC), 1,2-butylene carbonate, 2,3-butylene carbonate, 4-fluoro-1,3-dioxolan-2-one (FEC), trans- or cis-4,5-difluoro-1,3-dioxolan-2-one (the both will be hereunder named generically as "DFEC"), vinylene carbonate (VC), vinyl ethylene carbonate (VEC), and 4-ethynyl-1,3-dioxolan-2-one (EEC). One or more selected from ethylene carbonate, propylene carbonate, 4-fluoro-1,3-dioxolan-2-one, vinylene carbonate, and 4-ethynyl-1,3-dioxolan-2-one (EEC) are more suitable.

Use of at least one of cyclic carbonates having an unsaturated bond, such as a carbon-carbon double bond, a carbon-carbon triple bond, etc., or a fluorine atom is preferred because the electrochemical characteristics are much more improved at a high temperature, and it is more preferred to contain both a cyclic carbonate having an unsaturated bond, such as a carbon-carbon double bond, a carbon-carbon triple bond, etc., and a cyclic carbonate having a fluorine atom. As the cyclic carbonate having an unsaturated bond, such as a carbon-carbon double bond, a carbon-carbon triple bond, etc., VC, VEC, or EEC is more preferred, and as the cyclic carbonate having a fluorine atom, FEC or DFEC is more preferred.

A content of the cyclic carbonate having an unsaturated bond, such as a carbon-carbon double bond, a carbon-carbon triple bond, etc., is preferably 0.07% by volume or more, more preferably 0.2% by volume or more, and still more preferably 0.7% by volume or more relative to a total volume of the nonaqueous solvent, and when an upper limit thereof is preferably 7% by volume or less, more preferably 4% by volume or less, and still more preferably 2.5% by volume or less, stability of a surface film can be much more increased at a high temperature without impairing Li ion permeability, and hence, such is preferred.

A content of the cyclic carbonate having a fluorine atom is preferably 0.07% by volume or more, more preferably 4% by volume or more, and still more preferably 7% by volume or more relative to a total volume of the nonaqueous solvent, and when an upper limit thereof is preferably 35% by volume or less, more preferably 25% by volume or less, and still more preferably 15% by volume or less, stability of a surface film can be much more increased at a high temperature without impairing Li ion permeability, and hence, such is preferred.

In the case where the nonaqueous solvent includes both the cyclic carbonate having an unsaturated bond, such as a carbon-carbon double bond, a carbon-carbon triple bond, etc., and the cyclic carbonate having a fluorine atom, the content of the cyclic carbonate having an unsaturated bond, such as a carbon-carbon double bond, a carbon-carbon triple bond, etc., is preferably 0.2% by volume or more, more preferably 3% by volume or more, and still more preferably 7% by volume or more relative to the content of the cyclic carbonate having a fluorine atom, and when an upper limit thereof is preferably 40% by volume or less, more preferably 30% by volume or less, and still more preferably 15% by volume or less, stability of a surface film can be much more increased at a high temperature without impairing Li ion permeability, and hence, such is especially preferred.

When the nonaqueous solvent includes both ethylene carbonate and the cyclic carbonate having an unsaturated bond, such as a carbon-carbon double bond, a carbon-carbon triple bond, etc., stability of a surface film to be formed on an electrode at a high temperature is increased, and hence, such is preferred. A content of ethylene carbonate and the cyclic carbonate having an unsaturated bond, such as a carbon-carbon double bond, a carbon-carbon triple bond, etc., is preferably 3% by volume or more, more preferably 5% by volume or more, and still more preferably 7% by volume relative to a total volume of the nonaqueous solvent. An upper limit thereof is preferably 45% by volume or less, more preferably 35% by volume or less, and still more preferably 25% by volume or less.

These solvents may be used solely; in the case where a combination of two or more of the solvents is used, the electrochemical characteristics at a high temperature are more improved, and hence, such is preferred; and use of a combination of three or more thereof is especially preferred. As suitable combinations of these cyclic carbonates, EC and PC; EC and VC; PC and VC; VC and FEC; EC and FEC; PC and FEC; FEC and DFEC; EC and DFEC; PC and DFEC; VC and DFEC; VEC and DFEC; VC and EEC; EC and EEC; EC, PC and VC; EC, PC and FEC; EC, VC and FEC; EC, VC and VEC; EC, VC and EEC; EC, EEC and FEC; PC, VC and FEC; EC, VC and DFEC; PC, VC and DFEC; EC, PC, VC and FEC; EC, PC, VC and DFEC; and the like are preferred. Among the aforementioned combinations, combinations, such as EC and VC; EC and FEC; PC and FEC; EC, PC and VC; EC, PC and FEC; EC, VC and FEC; EC, VC and EEC; EC, EEC and FEC; PC, VC and FEC; EC, PC, VC and FEC; etc., are more preferred.

In the case of Embodiment 2, namely in the case of using the carboxylic acid ester compound represented by the foregoing general formula (I-2), combinations including PC, such as PC and FEC; EC, PC and VC; EC, PC and FEC; PC, VC and FEC; EC, PC, VC and FEC; etc., are still more preferred because battery characteristics at a high voltage are improved.

As the linear ester, there are suitably exemplified one or more asymmetric linear carbonates selected from methyl ethyl carbonate (MEC), methyl propyl carbonate (MPC), methyl isopropyl carbonate (MIPC), methyl butyl carbonate, and ethyl propyl carbonate; one or more symmetric linear carbonates selected from dimethyl carbonate (DMC), diethyl carbonate (DEC), dipropyl carbonate, and dibutyl carbonate; one or more linear carboxylic acid esters selected from methyl pivalate (MPiv), ethyl pivalate (EPiv), propyl pivalate (PPiv), methyl propionate (MP), ethyl propionate (EP), propyl propionate (PP), methyl acetate (MA), and ethyl acetate (EA); one or more asymmetric fluorinated linear carbonates selected from methyl (2,2,2-trifluoroethyl)

carbonate (MTFEC), ethyl (2,2,2-trifluoroethyl) carbonate, fluoromethyl (methyl) carbonate (FMMC), methyl (2,2,3,3-tetrafluoropropyl) carbonate (MTEFPC), ethyl (2,2,3,3-tetrafluoropropyl) carbonate, 2-fluoroethyl (methyl) carbonate (2-FEMC), and difluoromethyl (fluoromethyl) carbonate; and one or more symmetric fluorinated linear carbonates selected from bis(2-fluoroethyl) carbonate, bis(2,2,3,3-tetrafluoropropyl) carbonate, bis(2,2,2-trifluoroethyl) carbonate, and bis(fluoromethyl) carbonate.

Among the aforementioned linear esters, linear esters having a methyl group selected from linear carbonates, such as dimethyl carbonate (DMC), methyl ethyl carbonate (MEC), methyl propyl carbonate (MPC), methyl isopropyl carbonate (MIPC), methyl butyl carbonate, etc.; and linear carboxylic acid esters, such as methyl propionate (MP), ethyl propionate (EP), propyl propionate (PP), methyl acetate (MA), ethyl acetate (EA), etc., are preferred, and linear carbonates having a methyl group are especially preferred.

In the case of using a linear carbonate, it is preferred to use two or more thereof. Furthermore, it is more preferred that both the symmetric linear carbonate and the asymmetric linear carbonate are included, and it is still more preferred that a content of the symmetric linear carbonate is more than a content of the asymmetric linear carbonate.

Although the content of the linear ester is not particularly limited, it is preferred to use the linear ester in an amount in the range of from 60 to 90% by volume relative to a total volume of the nonaqueous solvent. When the content is 60% by volume or more, the viscosity of the nonaqueous electrolytic solution does not become excessively high, and when it is 90% by volume or less, there is less concern that an electroconductivity of the nonaqueous electrolytic solution is decreased, whereby the electrochemical characteristics at a high temperature are worsened, and therefore, it is preferred that the content of the linear ester falls within the aforementioned range.

From the viewpoint of improving the electrochemical characteristics at a high voltage, it is preferred that at least one selected from symmetric fluorinated linear carbonates and asymmetric fluorinated linear carbonates is included, and an asymmetric fluorinated linear carbonate having a methyl group, which is selected from methyl (2,2,2-trifluoroethyl) carbonate (MTFEC), 2-fluoroethyl (methyl) carbonate (2-FEMC), methyl (2,2,3,3-tetrafluoropropyl) carbonate (MTEFPC), and difluoromethyl (fluoromethyl) carbonate, is more preferred.

A proportion of the volume occupied by the symmetric linear carbonate in the linear carbonate is preferably 51% by volume or more, and more preferably 55% by volume or more. An upper limit thereof is preferably 95% by volume or less, and more preferably 85% by volume or less. It is especially preferred that dimethyl carbonate is included in the symmetric linear carbonate. It is more preferred that the asymmetric linear carbonate has a methyl group, and methyl ethyl carbonate is especially preferred. The aforementioned case is preferred because the electrochemical characteristics at a high temperature are much more improved.

As for a proportion of the cyclic carbonate and the linear ester, from the viewpoint of improving the electrochemical characteristics at a high temperature, a ratio of the cyclic carbonate to the linear ester (volume ratio) is preferably from 10/90 to 45/55, more preferably from 15/85 to 40/60, and especially preferably from 20/80 to 35/65.

As other nonaqueous solvents, there are suitably exemplified one or more selected from cyclic ethers, such as tetrahydrofuran, 2-methyltetrahydrofuran, 1,4-dioxane, etc.; linear ethers, such as 1,2-dimethoxyethane, 1,2-diethoxyethane, 1,2-butoxyethane, etc.; amides, such as dimethylformamide, etc.; sulfones, such as sulfolane, etc.; and lactones, such as γ-butyrolactone (GBL), γ-valerolactone, α-angelicalactone, etc.

The aforementioned nonaqueous solvents are generally mixed and used for the purpose of achieving appropriate physical properties. As for a combination thereof, for example, there are suitably exemplified a combination of a cyclic carbonate and a linear carbonate, a combination of a cyclic carbonate and a linear carboxylic acid ester, a combination of a cyclic carbonate, a linear carbonate, and a lactone, a combination of a cyclic carbonate, a linear carbonate, and an ether, a combination of a cyclic carbonate, a linear carbonate, and a linear carboxylic acid ester, and the like.

For the purpose of much more improving stability of a surface film at a high temperature, it is preferred to further add other additives in the nonaqueous electrolytic solution.

As specific examples of other additives, there are exemplified compounds of the following (A) to (I).

(A) One or more nitriles selected from acetonitrile, propionitrile, succinonitrile, glutaronitrile, adiponitrile, pimelonitrile, suberonitrile, and sebaconitrile.

(B) Aromatic compounds having a branched alkyl group, such as cyclohexylbenzene, fluorocyclohexylbenzene compounds 1-fluoro-2-cyclohexylbenzene, 1-fluoro-3-cyclohexylbenzene, and 1-fluoro-4-cyclohexylbenzene), tert-butylbenzene, tert-amylbenzene, 1-fluoro-4-tert-butylbenzene, etc., and aromatic compounds, such as biphenyl, terphenyl (including o-, m-, and p-forms), diphenyl ether, fluorobenzene, difluorobenzene (including o-, m-, and p-forms), anisole, 2,4-difluoroanisole, a partial hydride of terphenyl (e.g., 1,2-dicyclohexylbenzene, 2-phenylbicyclohexyl, 1,2-diphenylcyclohexane, and o-cyclohexylbiphenyl), etc.

(C) One or more isocyanate compounds selected from methyl isocyanate, ethyl isocyanate, butyl isocyanate, phenyl isocyanate, tetramethylene diisocyanate, hexamethylene diisocyanate, octamethylene diisocyanate, 1,4-phenylene diisocyanate, 2-isocyanatoethyl acrylate, and 2-isocyanatoethyl methacrylate.

(D) One or more triple bond-containing compounds selected from 2-propynyl methyl carbonate, 2-propynyl acetate, 2-propynyl formate, 2-propynyl methacrylate, 2-propynyl methanesulfonate, 2-propynyl vinylsulfonate, 2-propynyl 2-(methanesulfonyloxy)propionate, di(2-propynyl) oxalate, methyl 2-propynyl oxalate, ethyl 2-propynyl oxalate, di(2-propynyl) glutarate, 2-butyne-1,4-diyl dimethanesulfonate, 2-butyne-1,4-diyl diformate, and 2,4-hexadiyne-1,6-diyl dimethanesulfonate.

(E) One or more cyclic or linear S=O group-containing compounds selected from sultones, such as 1,3-propanesultone, 1,3-butanesultone, 2,4-butanesultone, 1,4-butanesultone, 1,3-propenesultone, 2,2-dioxide-1,2-oxathiolane-4-yl acetate, 5,5-dimethyl-1,2-oxathiolane-4-one 2,2-dioxide, etc.; cyclic sulfites, such as ethylene sulfite, hexahydrobenzo[1,3,2]dioxathiolane-2-oxide (also called 1,2-cyclohexanediol cyclic sulfite), 5-vinyl-hexahydro-1,3,2-benzodioxathiol-2-oxide, 4-(methylsulfonylmethyl)-1,3,2-dioxathiolane-2-oxide, etc.; sulfonic acid esters, such as butane-2,3-diyl dimethanesulfonate, butane-1,4-diyl dimethanesulfonate, methylene methanedisulfonate, dimethyl methanedisulfonate, pentafluorophenyl methanesulfonate, etc.; and vinylsulfone compounds, such as divinylsulfone, 1,2-bis(vinylsulfonyl)ethane, bis(2-vinylsulfonylethyl) ether, etc.

(F) Cyclic acetal compounds, such as 1,3-dioxolane, 1,3-dioxane, 1,3,5-trioxane, etc.

(G) One or more phosphorus-containing compounds selected from trimethyl phosphate, tributyl phosphate, trioctyl phosphate, tris(2,2,2-trifluoroethyl) phosphate, bis(2,2,2-trifluoroethyl) methyl phosphate, bis(2,2,2-trifluoroethyl) ethyl phosphate, bis(2,2,2-trifluoroethyl) 2,2-difluoroethyl phosphate, bis(2,2,2-trifluoroethyl) 2,2,3,3-tetrafluoropropyl phosphate, bis(2,2-difluoroethyl) 2,2,2-trifluoroethyl phosphate, bis(2,2,3,3-tetrafluoropropyl) 2,2,2-trifluoroethyl phosphate, (2,2,2-trifluoroethyl) (2,2,3,3-tetrafluoropropyl)methyl phosphate, tris(1,1,1,3,3,3-hexafluoropropan-2-yl) phosphate, methyl methylenebisphosphonate, ethyl methylenebisphosphonate, methyl ethylenebisphosphonate, ethyl ethylenebisphosphonate, methyl butylenebisphosphonate, ethyl butylenebisphosphonate, methyl 2-(dimethylphosphoryl)acetate, ethyl 2-(dimethylphosphoryl)acetate, methyl 2-(diethylphosphoryl)acetate, ethyl 2-(diethylphosphoryl)acetate, 2-propynyl 2-(dimethylphosphoryl)acetate, 2-propynyl 2-(diethylphosphoryl)acetate, methyl 2-(dimethoxyphosphoryl)acetate, ethyl 2-(dimethoxyphosphoryl)acetate, methyl 2-(diethoxyphosphoryl)acetate, ethyl 2-(diethoxyphosphoryl)acetate, 2-propynyl 2-(dimethoxyphosphoryl)acetate, 2-propynyl 2-(diethoxyphosphoryl)acetate, methyl pyrophosphate, and ethyl pyrophosphate.

(H) Linear carboxylic acid anhydrides, such as acetic anhydride, propionic anhydride, etc., and cyclic acid anhydrides, such as succinic anhydride, maleic anhydride, 3-allylsuccinic anhydride, glutaric anhydride, itaconic anhydride, 3-sulfo-propionic anhydride, etc.

(I) Cyclic phosphazene compounds, such as methoxypentafluorocyclotriphosphazene, ethoxypentafluorocyclotriphosphazene, phenoxypentafluorocyclotriphosphazene, ethoxyheptafluorocyclotetraphosphazene, etc.

Of the foregoing, when at least one selected from (A) the nitriles, (B) the aromatic compounds, and (C) the isocyanate compounds is included, the electrochemical characteristics at a high temperature and at a high voltage are much more improved, and hence, such is preferred.

Of (A) the nitriles, one or more selected from succinonitrile, glutaronitrile, adiponitrile, and pimelonitrile are more preferred.

Of (B) the aromatic compounds, one or more selected from biphenyl, terphenyl (including o-, m-, and p-forms), fluorobenzene, cyclohexylbenzene, tert-butylbenzene, and tert-amylbenzene are more preferred; and one or more selected from biphenyl, o-terphenyl, fluorobenzene, cyclohexylbenzene, and tert-amylbenzene are especially preferred.

Of (C) the isocyanate compounds, one or more selected from hexamethylene diisocyanate, octamethylene diisocyanate, 2-isocyanatoethyl acrylate, and 2-isocyanatoethyl methacrylate are more preferred.

A content of each of the aforementioned additives (A) to (C) is preferably 0.01 to 7% by mass in the nonaqueous electrolytic solution. When the content falls within this range, a surface film is sufficiently formed without causing an excessive increase of the thickness, and stability of the surface film at a high temperature is much more improved. The content is more preferably 0.05% by mass or more, and still more preferably 0.1% by mass or more in the nonaqueous electrolytic solution, and an upper limited thereof is more preferably 5% by mass or less, and still more preferably 3% by mass or less.

When (D) the triple bond-containing compound, (E) the cyclic or linear S=O group-containing compound selected from sultones, cyclic sulfites, sulfonic acid esters, and vinylsulfones, (F) the cyclic acetal compound, (G) the phosphorus-containing compound, (H) the cyclic acid anhydride, or (I) the cyclic phosphazene compound is included, stability of a surface film at a high temperature is much more improved, and hence, such is preferred.

As (D) the triple bond-containing compound, one or more selected from 2-propynyl methyl carbonate, 2-propynyl methacrylate, 2-propynyl methanesulfonate, 2-propynyl vinylsulfonate, 2-propynyl 2-(methanesulfonyloxy)propionate, di(2-propynyl) oxalate, methyl 2-propynyl oxalate, ethyl 2-propynyl oxalate, and 2-butyne-1,4-diyl dimethanesulfonate are preferred; and one or more selected from 2-propynyl methanesulfonate, 2-propynyl vinylsulfonate, 2-propynyl 2-(methanesulfonyloxy)propionate, di(2-propynyl) oxalate, and 2-butyne-1,4-diyl dimethanesulfonate are more preferred.

It is preferred to use (E) the cyclic or linear S=O group-containing compound selected from sultones, cyclic sulfites, sulfonic acid esters, and vinylsulfones, (provided that triple bond-containing compounds are not included).

As the cyclic S=O group-containing compound, there are suitably exemplified one or more selected from sultones, such as 1,3-propanesultone, 1,3-butanesultone, 1,4-butanesultone, 2,4-butanesultone, 1,3-propenesultone, 2,2-dioxide-1,2-oxathiolane-4-yl acetate, 5,5-dimethyl-1,2-oxathiolane-4-one 2,2-dioxide, etc.; sulfonic acid esters, such as methylene methanedisulfonate, etc.; and cyclic sulfites, such as ethylene sulfite, 4-(methylsulfonylmethyl)-1,3,2-dioxathiolane 2-oxide, etc.

As the linear S=O group-containing compound, there are suitably exemplified one or more selected from butane-2,3-diyl dimethanesulfonate, butane-1,4-diyl dimethanesulfonate, dimethyl methanedisulfonate, pentafluorophenyl methanesulfonate, divinylsulfone, and bis(2-vinylsulfonylethyl) ether.

Of the aforementioned cyclic or linear S=O group-containing compounds, one or more selected from 1,3-propanesultone, 1,4-butanesultone, 2,4-butanesultone, 2,2-dioxide-1,2-oxathiolane-4-yl acetate, 5,5-dimethyl-1,2-oxathiolane-4-one 2,2-dioxide, butane-2,3-diyl dimethanesulfonate, pentafluorophenyl methanesulfonate, and divinylsulfone are more preferred.

As (F) the cyclic acetal compound, 1,3-dioxolane and 1,3-dioxane are preferred, and 1,3-dioxane is more preferred.

As (G) the phosphorus-containing compound, tris(2,2,2-trifluoroethyl) phosphate, tris(1,1,1,3,3,3-hexafluoropropan-2-yl) phosphate, methyl 2-(dimethylphosphoryl)acetate, ethyl 2-(dimethylphosphoryl)acetate, methyl 2-(diethylphosphoryl)acetate, ethyl 2-(diethylphosphoryl)acetate, 2-propynyl 2-(dimethylphosphoryl)acetate, 2-propynyl 2-(diethylphosphoryl)acetate, methyl 2-(dimethoxyphosphoryl)acetate, ethyl 2-(dimethoxyphosphoryl)acetate, methyl 2-(diethoxyphosphoryl)acetate, ethyl 2-(diethoxyphosphoryl)acetate, 2-propynyl 2-(dimethoxyphosphoryl)acetate, and 2-propynyl 2-(diethoxyphosphoryl)acetate are preferred; and tris(2,2,2-trifluoroethyl) phosphate, tris(1,1,1,3,3,3-hexafluoropropan-2-yl) phosphate, ethyl 2-(diethylphosphoryl)acetate, 2-propynyl 2-(dimethylphosphoryl)acetate, 2-propynyl 2-(diethylphosphoryl)acetate, ethyl 2-(diethoxyphosphoryl)acetate, 2-propynyl 2-(dimethoxyphosphoryl)acetate, and 2-propynyl 2-(diethoxyphosphoryl)acetate are more preferred.

As (H) the cyclic acid anhydride, succinic anhydride, maleic anhydride, and 3-allylsuccinic anhydride are preferred, and succinic anhydride and 3-allylsuccinic anhydride are more preferred.

As (I) the cyclic phosphazene compound, cyclic phosphazene compounds, such as methoxypentafluorocyclotriphosphazene, ethoxypentafluorocyclotriphosphazene, phenoxypentafluorocyclotriphosphazene, etc., are preferred, and methoxypentafluorocyclotriphosphazene and ethoxypentafluorocyclotriphosphazene are more preferred.

A content of each of the aforementioned additives (D) to (I) is preferably 0.001 to 5% by mass in the nonaqueous electrolytic solution. When the content falls within this range, a surface film is sufficiently formed without causing an excessive increase of the thickness, and stability of the surface film at a high temperature is much more improved. The content is more preferably 0.01% by mass or more, and still more preferably 0.1% by mass or more in the nonaqueous electrolytic solution, and an upper limited thereof is more preferably 3% by mass or less, and still more preferably 2% by mass or less.

For the purpose of much more improving stability of a surface film at a high temperature, it is preferred that at least one selected from lithium salts having an oxalate skeleton, lithium salts having a phosphate skeleton, and lithium salts having an S=O group is included in the nonaqueous electrolytic solution.

As specific examples of the lithium salt, there are suitably exemplified at least one lithium salt having an oxalate skeleton, which is selected from lithium bis(oxalate)borate (LiBOB), lithium difluoro(oxalate)borate (LiDFOB), lithium tetrafluoro(oxalate)phosphate (LiTFOP), and lithium difluorobis(oxalate)phosphate (LiDFOP); a lithium salt having a phosphate skeleton, such as $LiPO_2F_2$, $Li_2PO_3F$, etc.; and at least one lithium salt having an S=O group, which is selected from lithium trifluoro((methanesulfonyl)oxy)borate (LiTFMSB), lithium pentafluoro((methanesulfonyl)oxy)phosphate (LiPFMSP), lithium methyl sulfate (LMS), lithium ethyl sulfate (LES), lithium 2,2,2-trifluoroethyl sulfate (LFES), and $FSO_3Li$.

Among those, it is more preferred that a lithium salt selected from LiBOB, LiDFOB, LiTFOP, LiDFOP, $LiPO_2F_2$, LiTFMSB, LMS, LES, LFES, and $FSO_3Li$ is included.

A total content of at least one selected from lithium salts having an oxalate skeleton, lithium salts having a phosphate skeleton, and lithium salts having an S=O group, in particular at least one lithium salt selected from LiBOB, LiDFOB, LiTFOP, LiDFOP, $LiPO_2F_2$, $Li_2PO_3F$, LiTFMSB, LiPFMSP, LMS, LES, LFES, and $FSO_3Li$, is preferably 0.001 to 10% by mass in the nonaqueous electrolytic solution. When the content is 10% by mass or less, there is less concern that a surface film is excessively formed on an electrode, so that the storage characteristics are worsened, and when it is 0.001% by mass or more, the formation of a surface film is sufficient, and in the case of using a battery at a high temperature and at a high voltage, an improving effect of the characteristics is enhanced. The content is preferably 0.05% by mass or more, more preferably 0.1% by mass or more, and still more preferably 0.3% by mass or more in the nonaqueous electrolytic solution. An upper limit thereof is preferably 5% by mass or less, more preferably 3% by mass or less, and especially preferably 2% by mass or less.

(Lithium Salt)

As the electrolyte salt which is used in the present invention, there are suitably exemplified the following lithium salts.

As the lithium salt, there are suitably exemplified inorganic lithium salts, such as $LiPF_6$, $LiBF_4$, $LiClO_4$, etc.; linear fluoroalkyl group-containing lithium salts, such as $LiN(SO_2F)_2$, $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; and cyclic fluoroalkylene chain-containing lithium salts, such as $(CF_2)2(SO2)2NLi$, $(CF_2)_3(SO_2)_2NLi$, etc.; and the like. At least one lithium salt selected from these lithium salts is suitably exemplified, and one or more thereof may be solely or in admixture.

Among those, one or more selected from $LiPF_6$, $LiBF_4$, $LiN(SO_2CF_3)_2$, $LiN(SO_2C_2F_5)_2$, and $LiN(SO_2F)_2$ are preferred, and it is most preferred to use $LiPF_6$.

In general, a concentration of the lithium salt is preferably 0.3 M or more, more preferably 0.7 M or more, and still more preferably 1.1 M or more relative to the nonaqueous solvent. An upper limit thereof is preferably 2.5 M or less, more preferably 2.0 M or less, and still more preferably 1.6 M or less.

As for a suitable combination of these lithium salts, the case of including $LiPF_6$ and further including at least one lithium salt selected from $LiBF_4$. $LiN(SO_2CF_3)_2$, and $LiN(SO_2F)_2$ in the nonaqueous electrolytic solution is preferred.

When a proportion of the lithium salt other than $LiPF_6$ occupying in the nonaqueous solvent is 0.001 M or more, an improving effect of the electrochemical characteristics in the case of using the battery at a high temperature is liable to be exhibited, and when it is 1.0 M or less, there is less concern that the improving effect of the electrochemical characteristics in the case of using the battery at a high temperature is worsened, and hence, such is preferred. The proportion is preferably 0.01 M or more, especially preferably 0.03 M or more, and most preferably 0.04 M or more. An upper limit thereof is preferably 0.8 M or less, more preferably 0.6 M or less, and especially preferably 0.4 M or less.

[Production of Nonaqueous Electrolytic Solution]

The nonaqueous electrolytic solution of the present invention may be obtained, for example, by mixing the aforementioned nonaqueous solvent, adding the aforementioned electrolyte salt thereto, and further adding the carboxylic acid ester compound represented by the foregoing general formula (I), in particular the carboxylic acid ester compound represented by the foregoing general formula (I-1), (I-2), or (I-3) to the resulting nonaqueous electrolytic solution.

At this time, the nonaqueous solvent to be used and the compounds to be added to the nonaqueous electrolytic solution are preferably purified in advance to decrease impurities as far as possible within the range where the productivity is not remarkably worsened.

The nonaqueous electrolytic solution of the present invention may be used in first to fourth energy storage devices shown below, in which the nonaqueous electrolytic solution may be used as the nonaqueous electrolyte not only in the form of a liquid but also in the form of gel. Furthermore, the nonaqueous electrolytic solution of the present invention may also be used for a solid polymer electrolyte. Above all, the nonaqueous electrolytic solution is preferably used in the first energy storage device using a lithium salt as the electrolyte salt (namely, for a lithium battery) or in the fourth energy storage device (namely, for a lithium ion capacitor), more preferably used in a lithium battery, and still more preferably used in a lithium secondary battery.

[First Storage Device (Lithium Battery)]

The lithium battery as referred to in the present specification is a generic name for a lithium primary battery and a lithium secondary battery. In the present specification, the term "lithium secondary battery" is used as a concept also including a so-called lithium ion secondary battery. The lithium battery of the present invention includes a positive electrode, a negative electrode, and the aforementioned nonaqueous electrolytic solution having an electrolyte salt dissolved in a nonaqueous solvent. Other constitutional members than the nonaqueous electrolytic solution, such as the positive electrode, the negative electrode, etc., may be used without being particularly limited.

For example, examples of a positive electrode active material used for a lithium secondary battery include a complex metal oxide containing lithium and one or more selected from cobalt, manganese, and nickel. These positive electrode active materials may be used solely or in combination of two or more thereof.

Examples of the lithium complex metal oxide include one or more selected from $LiCoO_2$, $LiMn_2O_4$, $LiNiO_2$, $LiCo_{1-x}Ni_xO_2$ (0.01<x<1), $LiCo_{1/3}Ni_{1/3}Mn_{1/3}O_2$, $LiNi_{1/2}Mn_{3/2}O_4$, and $LiCo_{0.98}Mg_{0.02}O_2$. These materials may be used as a combination, such as a combination of $LiCoO_2$ and $LiMn_2O_4$, a combination of $LiCoO_2$ and $LiNiO_2$, and a combination of $LiMn_2O_4$ and $LiNiO_2$.

For improving the safety on overcharging and the cycle characteristics, and for enabling the use at a charge potential of 4.3 V or more, a part of the lithium complex metal oxide may be substituted with other elements. For example, a part of cobalt, manganese, or nickel may be substituted with at least one element selected from Sn, Mg, Fe, Ti, Al, Zr, Cr, V, Ga, Zn, Cu, Bi, Mo, and La, a part of O may be substituted with S or F, or the oxide may be coated with a compound containing any of such other elements.

Among those, a lithium complex metal oxide capable of being used at a charge potential of the positive electrode in a fully-charged state of 4.3 V or more based on Li, such as $LiCoO_2$, $LiMn_2O_4$, and $LiNiO_2$, is preferred; and a lithium complex metal oxide capable of being used at 4.4 V or more, such as $LiCo_{1-x}M_xO_2$ (wherein M represents one or more elements selected from Sn, Mg, Fe, Ti, Al, Zr, Cr, V, Ga, Zn, and Cu, and 0.001≤x≤0.05), $LiCo_{1/3}Ni_{1/3}Mn_{1/3}O_2$, $LiNi_{1/2}Mn_{3/2}O_4$, and a solid solution of $Li_2MnO_3$ and $LiMO_2$ (wherein M represents a transition metal, such as Co, Ni, Mn, Fe, etc.), is more preferred. The use of the lithium complex metal oxide capable of acting at a high charge voltage is liable to worsen the electrochemical characteristics particularly in a broad temperature range due to the reaction with the electrolytic solution on charging, but in the lithium secondary battery according to the present invention, worsening of the electrochemical characteristics can be inhibited. In particular, a battery with a positive electrode containing Mn tends to have an increased resistance due to elution of Mn ions from the positive electrode, thereby providing the tendency of worsening the electrochemical characteristics in a broad temperature range. However, the lithium secondary battery according to the present invention is preferred because worsening of the electrochemical characteristics can be inhibited.

Furthermore, a lithium-containing olivine-type phosphate may also be used as the positive electrode active material. In particular, a lithium-containing olivine-type phosphate including one or more selected from iron, cobalt, nickel, and manganese is preferred. As specific examples thereof, there are exemplified one or more selected from $LiFePO_4$, $LiCoPO_4$, $LiNiPO_4$, and $LiMnPO_4$. A part of such a lithium-containing olivine-type phosphate may be substituted with other element. A part of iron, cobalt, nickel, or manganese may be substituted with one or more elements selected from Co, Mn, Ni, Mg, Al, B, Ti, V, Nb, Cu, Zn, Mo, Ca, Sr, W, Zr, and the like, or the phosphate may be coated with a compound containing any of these other elements or with a carbon material. Among those, $LiFePO_4$ and $LiMnPO_4$ are preferred. The lithium-containing olivine-type phosphate may also be used, for example, in admixture with the aforementioned positive electrode active material.

Examples of the positive electrode for a lithium primary battery include oxides or chalcogen compounds of one or more metal elements, such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, and the like; a sulfur compound, such as $SO_2$, $SOCl_2$, etc.; and a carbon fluoride (graphite fluoride) represented by a general formula $(CF_x)_n$. Among those, $MnO_2$, $V_2O_5$, graphite fluoride, and the like are preferred.

In the case where when 10 g of the aforementioned positive electrode active material is dispersed in 100 mL of distilled water, a pH of a supernatant thereof is 10.0 to 12.5, the improving effect of the electrochemical characteristics in a much broader temperature range is liable to be obtained, and hence, such is preferred. The case where the pH is 10.5 to 12.0 is more preferred.

In the case where Ni is included as an element in the positive electrode, the content of impurities, such as LiOH, etc., in the positive electrode active material tends to increase, and the improving effect of the electrochemical characteristics in a much broader temperature range is liable to be obtained, and hence, such is preferred. The case where an atomic concentration of Ni in the positive electrode active material is 5 to 25 atomic % is more preferred, and the case where the atomic concentration of Ni is 8 to 21 atomic % is especially preferred.

An electroconductive agent of the positive electrode is not particularly limited as far as it is an electron-conductive material that does not undergo chemical change. Examples thereof include graphite, such as natural graphite (e.g., flaky graphite, etc.), artificial graphite, etc.; one or more carbon blacks selected from acetylene black, Ketjen black, channel black, furnace black, lamp black, and thermal black; and the like. The graphite and the carbon black may be appropriately mixed and used. An amount of the electroconductive agent added to a positive electrode mixture is preferably from 1 to 10% by mass, and especially preferably from 2 to 5% by mass.

The positive electrode can be produced in such a manner that the positive electrode active material is mixed with an electroconductive agent, such as acetylene black, carbon black, etc., and then mixed with a binder, such as polytetrafluoroethylene (PTFE), polyvinylidene fluoride (PVDF), a copolymer of styrene and butadiene (SBR), a copolymer of acrylonitrile and butadiene (NSR), carboxymethyl cellulose (CMC), an ethylene-propylene-diene terpolymer, etc., to which is then added a high-boiling point solvent, such as 1-methyl-2-pyrrolidone, etc., followed by kneading to provide a positive electrode mixture, and the positive electrode mixture is applied onto a collector, such as an aluminum foil, a stainless steel-made lath plate, etc., dried, shaped under pressure, and then heat-treated in vacuum at a temperature of about 50° C. to 250° C. for about 2 hours.

A density of the positive electrode except for the collector is generally 1.5 g/cm³ or more, and for the purpose of further increasing a capacity of the battery, the density is preferably 2 g/cm$^3$ or more, more preferably 3 g/cm$^3$ or more, and still more preferably 3.6 g/cm$^3$ or more. An upper limit thereof is preferably 4g/cm$^3$ or less.

As a negative electrode active material for a lithium secondary battery, one or more selected from lithium metal, a lithium alloy, a carbon material capable of absorbing and releasing lithium [e.g., graphitizable carbon, non-graphitizable carbon having a spacing of a (002) plane of 0.37 nm or more, graphite having a spacing of the (002) plane of 0.34 nm or less, etc.], tin (elemental substance), a tin compound, silicon (elemental substance), a silicon compound, and a lithium titanate compound, such as $Li_4Ti_5O_{12}$, etc., may be used.

Among the aforementioned negative electrode active materials, in the ability of absorbing and releasing lithium ions, the use of a high-crystalline carbon material, such as artificial graphite, natural graphite, etc., is more preferred, and the use of a carbon material having a graphite-type crystal structure in which a lattice (002) spacing ($d_{002}$) is 0.340 nm (nanometers) or less, and especially from 0.335 to 0.337 nm, is still more preferred. In particular, the use of artificial graphite particles having a bulky structure containing plural flattened graphite fine particles that are aggregated or bonded non-parallel to each other, or graphite particles produced through a spheroidizing treatment of flaky natural graphite particles by repeatedly applying a mechanical action, such as a compression force, a friction force, a shear force, etc., is preferred.

When a ratio $I(110)/I(004)$ of a peak intensity $I(110)$ of the (110) plane to a peak intensity $I(004)$ of the (004) plane of the graphite crystal obtained through X-ray diffractometry of a negative electrode sheet that is shaped under pressure to such an extent that a density of the negative electrode except for the collector is 1.5 g/cm$^3$ or more, is 0.01 or more, the electrochemical characteristics are improved in a much broader temperature range, and hence, such is preferred. The ratio $I(110)/I(004)$ is more preferably 0.05 or more, and still more preferably 0.1 or more. An upper limit of the ratio $I(110)/I(004)$ of the peak intensity is preferably 0.5 or less, and more preferably 0.3 or less because there may be the case where the crystallinity is worsened to lower the discharge capacity of the battery due to an excessive treatment.

When the high-crystalline carbon material (core material) is coated with a carbon material having lower crystallinity than the core material, the electrochemical characteristics in a broad temperature range become much more favorable, and hence, such is preferred. The crystallinity of the carbon material in the coating may be confirmed through TEM.

When the high-crystalline carbon material is used, there is a tendency that it reacts with the nonaqueous electrolytic solution on charging, thereby worsening the electrochemical characteristics at a low temperature or a high temperature due to an increase of interfacial resistance. However, in the lithium secondary battery according to the present invention, the electrochemical characteristics in a broad temperature range become favorable.

As the metal compound capable of absorbing and releasing lithium as a negative electrode active material, there are suitably exemplified compounds containing at least one metal element, such as Si, Ge, Sn, Pb, P, Sb, Bi, Al, Ga, In, Ti, Mn, Fe, Co, Ni, Cu, Zn, Ag, Mg, Sr, Ba, etc. The metal compound may be in any form including an elemental substance, an alloy, an oxide, a nitride, a sulfide, a boride, an alloy with lithium, and the like, and any of an elemental substance, an alloy, an oxide, and an alloy with lithium is preferred because the battery capacity can be increased. Above all, compounds containing at least one element selected from Si, Ge, and Sn are preferred, and compounds containing at least one element selected from Si and Sn are more preferred because the battery capacity can be increased.

The negative electrode can be produced in such a manner that the same electroconductive agent, binder, and high-boiling point solvent as in the production of the positive electrode as described above are used and kneaded to provide a negative electrode mixture, and the negative electrode mixture is then applied on a collector, such as a copper foil, etc., dried, shaped under pressure, and then heat-treated in vacuum at a temperature of about from 50° C. to 250° C. for about 2 hours.

A density of the negative electrode except for the collector is generally 1.1 g/cm$^3$ or more, and for the purpose of further increasing a capacity of the battery, the density is preferably 1.5 g/cm$^3$ or more, and more preferably 1.7 g/cm$^3$ or more. An upper limit thereof is preferably 2 g/cm$^3$ or less.

Examples of the negative electrode active material for a lithium primary battery include lithium metal and a lithium alloy.

The structure of the lithium battery is not particularly limited, and may be a coin-type battery, a cylinder-type battery, a prismatic battery, a laminate-type battery, or the like, each having a single-layered or multi-layered separator.

The separator for the battery is not particularly limited, and a single-layered or laminated micro-porous film of a polyolefin, such as polypropylene, polyethylene, etc., a woven fabric, a nonwoven fabric, and the like may be used.

The lithium secondary battery in the present invention has excellent electrochemical characteristics in a broad temperature range even when a final charging voltage is 4.2 V or more, particularly 4.3 V or more, and furthermore, the characteristics are favorable even at 4.4 V or more. A final discharging voltage may be generally 2.8 V or more, and further 2.5 V or more, and the final discharging voltage of the lithium secondary battery in the present invention may be 2.0 V or more. An electric current is not particularly limited, and in general, the battery may be used within a range of from 0.1 to 30 C. The lithium battery in the present invention may be charged and discharged at from −40 to 100° C., and preferably from −10 to 80° C.

In the present invention, as a countermeasure against the increase in the internal pressure of the lithium battery, there may also be adopted such a method that a safety valve is provided in a battery cap, or a cutout is provided in a component, such as a battery can, a gasket, etc. As a safety countermeasure for prevention of overcharging, a circuit cut-off mechanism capable of detecting the internal pressure of the battery to cut off the current may be provided in the battery cap.

[Second Energy Storage Device (Electric Double Layer Capacitor)]

The second energy storage device of the present invention is an energy storage device including the nonaqueous electrolytic solution of the present invention and storing energy by utilizing an electric double layer capacitance in an interface between the electrolytic solution and the electrode. One example of the present invention is an electric double layer capacitor. A most typical electrode active material which is used in this energy storage device is active carbon. The double layer capacitance increases substantially in proportion to a surface area.

[Third Energy Storage Device]

The third energy storage device of the present invention is an energy storage device including the nonaqueous electrolytic solution of the present invention and storing energy by utilizing a doping/dedoping reaction of the electrode. Examples of the electrode active material which is used in this energy storage device include a metal oxide, such as ruthenium oxide, iridium oxide, tungsten oxide, molybdenum oxide, copper oxide, etc., and a n-conjugated polymer, such as polyacene, a polythiophene derivative, etc. A capacitor using such an electrode active material is capable of storing energy following the doping/de doping reaction of the electrode.

[Fourth Energy Storage Device (Lithium Ion Capacitor)]

The fourth energy storage device of the present invention is an energy storage device including the nonaqueous electrolytic solution of the present invention and storing energy by utilizing intercalation of lithium ions into a carbon material, such as graphite, etc., as the negative electrode. This energy storage device is called a lithium ion capacitor (LIC). Examples of the positive electrode include one utilizing an electric double layer between an active carbon electrode and an electrolytic solution, one utilizing a doping/dedoping reaction of a π-conjugated polymer electrode, and the like. The electrolytic solution contains at least a lithium salt, such as $LiPF_6$, etc.

One of the carboxylic acid ester compounds as a novel compound of the present invention is represented by the following general formula (II).

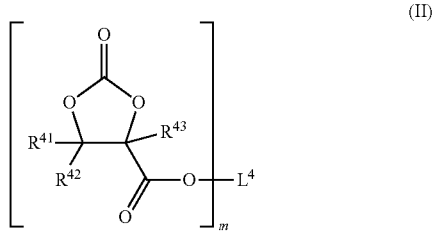

In the formula, each of $R^{41}$ and $R^{42}$ independently represents a hydrogen atom, a halogen atom, an alkyl group having 1 to 6 carbon atoms, in which at least one hydrogen atom may be substituted with a halogen atom, a cycloalkyl group having 3 to 6 carbon atoms, an alkenyl group having 2 to 6 carbon atoms, an alkynyl group having 3 to 6 carbon atoms, an aralkyl group having 7 to 13 carbon atoms, in which at least one hydrogen atom may be substituted with a halogen atom, an aryl group having 6 to 12 carbon atoms, in which at least one hydrogen atom may be substituted with a halogen atom, or a —C(=O)—$OR^{44}$ group, and when $R^{41}$ and $R^{42}$ are each an alkyl group, then $R^{41}$ and $R^{42}$ may be bonded to each other to form a ring structure. $R^{43}$ represents a hydrogen atom, a halogen atom, or an alkyl group having 1 to 6 carbon atoms, and m represents 1 or 2.

When m is 1, then $L^4$ and $R^{44}$ may be the same as or different from each other and represent a halogenated alkyl group having 1 to 6 carbon atoms, in which at least one hydrogen atom is substituted with a halogen atom, a halogenated cycloalkyl group having 3 to 6 carbon atoms, in which at least one hydrogen atom is substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 3 to 6 carbon atoms, a cyanoalkyl group having 2 to 6 carbon atoms, a halogenated aralkyl group having 7 to 13 carbon atoms, in which at least one hydrogen atom is substituted with a halogen atom, or a halogenated aryl group having 6 to 12 carbon atoms, in which at least one hydrogen atom is substituted with a halogen atom, and when in is 2, then $L^4$ represents an alkylene group having 2 to 6 carbon atoms, in which at least one hydrogen atom is substituted with a halogen atom, an alkenylene group having 4 to 8 carbon atoms, or an alkynylene group having 4 to 8 carbon atoms, and $R^{44}$ is the same as described above, provided that when m is 1, then $L^4$ is not a 3-methyl-2-buten-1-yl group.

In the general formula (II), the substituents $R^{41}$, $R^{42}$, and $R^{43}$ are synonymous with $R^1$, $R^2$, and $R^3$ in the general formula (I), respectively.

m is corresponding to a part of n of the general formula (I) and represents 1 or 2. Detailed thereof have already been explained in the foregoing general formula (I), and hence, in this section, the explanation is omitted in order to avoid overlapping. In this case, the substituents $R^4$ and L of the general formula (I) can be designated as the substituents $R^{44}$ and $L^4$ of the general formula (II), respectively.

Specific carboxylic ester compounds represented by the foregoing general formula (II) are the same as the specific compounds and preferred compounds described with respect to the general formula (I), exclusive of the compounds having any one of the structural formulae of 1 to 11, 56 to 58, 61 to 63, 64 to 68, 83, 87, 89, 91, 93, 95, 91, 97, 101, 103, 105, 107, 109, 111, 113, 115, 117, 119 to 121, 128 to 136, and 147 to 149.

The carboxylic acid ester compound represented by the general formula (II) of the present invention may be synthesized by the following two methods, but the present invention is not limited to these production methods.

(a) Dehydration Condensation Method:

The carboxylic acid ester compound is obtained by subjecting a carboxylic acid compound obtained by the method described in WO2013/092011 and an alcohol compound to dehydration condensation in a solvent or non-solvent in the presence of a dehydration condensing agent.

(b) Acid Chloride Method:

The carboxylic acid ester compound is obtained by allowing an acid chloride of a carboxylic acid compound to react with an alcohol compound in a solvent in the presence or absence of a base.

Another one of the carboxylic acid ester compounds as a novel compound of the present invention is represented by the following general formula (III).

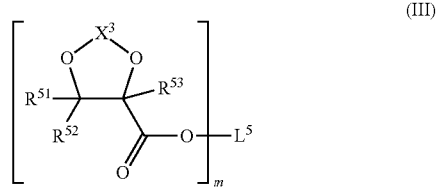

In the formula, each of $R^{51}$ and $R^{52}$ independently represents a hydrogen atom, a halogen atom, an alkyl group having 1 to 6 carbon atoms, a cycloalkyl group having 3 to 6 carbon atoms, an alkenyl group having 2 to 6 carbon atoms, an alkynyl group having 3 to 6 carbon atoms, an aralkyl group having 7 to 13 carbon atoms, an aryl group having 6 to 12 carbon atoms, or a —C(=O)—$OR^{54}$ group, and when $R^{51}$ and $R^{52}$ are each an alkyl group, then $R^{51}$ and $R^{52}$ may be bonded to each other to form a ring structure. $R^{53}$ represents a hydrogen atom, a halogen atom, or an alkyl group having 1 to 6 carbon atoms, and m represents 1 or 2.

When m is 1, then $L^5$ and $R^{54}$ may be the same as or different from each other and represent an alkyl group having 1 to 6 carbon atoms, a cycloalkyl group having 3 to 6 carbon atoms, an alkenyl group having 2 to 6 carbon atoms, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, or an aryl group having 6 to 12 carbon atoms, and when m is 2, then $L^5$ represents an alkylene group having 2 to 8 carbon atoms, an alkenylene group having 4 to 8 carbon atoms, or an alkynylene group having 4 to 8 carbon atoms, at least one hydrogen atom of $L^5$ may be substituted with a halogen atom, and $R^{54}$ is the same as described above.

$X^3$ represents an $-S(=O)_2-R^{55}-S(=O)_2-$ group, and $R^{55}$ represents an alkylene group having 1 to 4 carbon atoms, in which at least one hydrogen atom may be substituted with a halogen atom or an alkyl group having 1 to 4 carbon atoms.

At least one hydrogen atom of the alkyl group having 1 to 6 carbon atoms, the cycloalkyl group having 3 to 6 carbon atoms, the alkenyl group having 2 to 6 carbon atoms, the alkynyl group having 3 to 6 carbon atoms, the alkoxyalkyl group having 2 to 6 carbon atoms, the cyanoalkyl group having 2 to 6 carbon atoms, the aralkyl group having 7 to 13 carbon atoms, or the aryl group having 6 to 12 carbon atoms as $R^{51}$, $R^{52}$, $R^{54}$, or $L^5$, may be substituted with a halogen atom.

Specific compounds represented by the foregoing general formula (III) are the same as the description of specific compounds and preferred description for the general formula (I).

The compound represented by the general formula (III) may be synthesized by a method of allowing an alkanedisulfonyl dihalide compound to react with a corresponding diol compound in a solvent or non-solvent in the presence of a base, but the present invention is not limited to such a method.

As for effects of the compound represented by the general formula (III), for example, an effect as an additive for an energy storage device shown in the following Examples, but the invention is not limited thereto.

The compound represented by the general formula (III) is a novel carboxylic acid ester compound, and in view of a special structure thereof, it includes an application as an electrolyte, and so on in the fields of general chemistry, particularly organic chemistry, electrochemistry, biochemistry, and polymer chemistry.

In consequence, the compound represented by the general formula (III) is a useful compound as intermediate raw materials of drugs, agricultural chemicals, electronic materials, polymer materials, and the like, and also as electronic materials.

EXAMPLES

Synthesis Examples of the carboxylic acid ester compound which is used in the present invention and Examples of the electrolytic solution of the present invention are hereunder described, but it should not be construed that the present invention is limited to these Synthesis Examples and Examples.

Synthesis Example I-1

Synthesis of 2-Propynyl 2-Oxo-1,3-dioxolane-4-carboxylate (Synthetic Compound 1)

7.1 g (0.054 mol) of 2-oxo-1,3-dioxolane-4-carboxylic acid, 30 mL of ethyl acetate, and 3.0 g (0.054 mol) of propargyl alcohol were added at room temperature and then cooled to 10° C. To this solution, 12.4 g (0.065 mol) of 1-(3-dimethylaminopropyl)-3-ethylcarbodiimide hydrochloride was added at 10 to 20° C. over 10 minutes, followed by stirring at room temperature for 3 hours. The reaction solution was washed with water and extracted with ethyl acetate, and the solvent was concentrated under reduced pressure. The resulting residue was purified by means of silica gel column chromatography (elution with ethyl acetate/hexane=½), thereby obtaining 4.9 g (yield: 53%) of the targeted 2-propynyl 2-oxo-1,3-dioxolane-4-carboxylate.

The obtained 2-propynyl 2-oxo-1,3-dioxolane-4-carboxylate was subjected to $^1$H-NMR and melting point measurement, thereby confirming its structure. The results are shown below.

$^1$H-NMR (400 MHz, CDCl$_3$): δ=5.14 (dd, J=5.4 Hz, 9.0 Hz, 1H), δ=4.86 (d, J=2.5 Hz, 2H), δ=4.71 (t, J=9.0 Hz, 1H), δ=4.56 (dd, J=5.4 Hz, 9.0 Hz, 1H), 2.58 (t, J=2.5 Hz, 1H)

Melting point: 35° C.

Examples I-1 to I-46 and Comparative Examples I-1 to I-3

[Production of Lithium Ion Secondary Battery]

94% by mass of LiNi$_{1/3}$Mn$_{1/3}$Co$_{1/3}$O$_2$ and 3% by mass of acetylene black (electroconductive agent) were mixed and then added to and mixed with a solution which had been prepared by dissolving 3% by mass of polyvinylidene fluoride (binder) in 1-methyl-2-pyrrolidone in advance, thereby preparing a positive electrode mixture paste. This positive electrode mixture paste was applied onto one surface of an aluminum foil (collector), dried, and treated under pressure, followed by cutting into a predetermined size, thereby producing a positive electrode sheet in a belt-like form. A density of the positive electrode except for the collector was 3.6 g/cm$^3$.

10% by mass of silicon (elemental substance), 80% by mass of artificial graphite (d$_{002}$=0.335 nm, negative electrode active material), and 5% by mass of acetylene black (electroconductive agent) were mixed and then added to and mixed with a solution which had been prepared by dissolving 5% by mass of polyvinylidene fluoride (binder) in 1-methyl-2-pyrrolidone in advance, thereby preparing a negative electrode mixture paste. This negative electrode mixture paste was applied onto one surface of a copper foil (collector), dried, and treated under pressure, followed by cutting into a predetermined size, thereby producing a negative electrode sheet. A density of the negative electrode except for the collector was 1.5 g/cm$^3$.

The electrode sheet was analyzed by X-ray diffractometry, and a ratio [I(110)/I(004)] of the peak intensity I(110) of the (110) plane to the peak intensity I(004) of the (004) plane of the graphite crystal was 0.1.

The above-obtained positive electrode sheet, a microporous polyethylene-made film separator and the above-obtained negative electrode sheet were laminated in this order, and the nonaqueous electrolytic solution having each of compositions shown in Tables 1 and 2 was added, thereby producing a laminate-type battery.

[Discharge Capacity Retention Rate After High-Temperature Charged Storage]

<Initial Discharge Capacity>

In a thermostatic chamber at 25° C., the laminate-type battery produced by the aforementioned method was charged up to a final voltage of 4.35 V with a constant current of 1 C and under a constant voltage for 3 hours and then discharged down to a final voltage of 2.75 V with a constant current of 1 C, thereby determining an initial discharge capacity.

<High-Temperature Charged Storage Test>

Subsequently, in a thermostatic chamber at 60° C., this laminate-type battery was charged up to a final voltage of 4.35 V with a constant current of 1 C and under a constant voltage for 3 hours, and then stored for 7 days while being kept at 4.35 V. Thereafter, the battery was placed in a thermostatic chamber at 25° C., and once discharged under a constant current of 1 C to a final voltage of 2.75 V.

<Discharge Capacity After High-Temperature Charged Storage>

Further thereafter, the discharge capacity after the high-temperature charged storage was determined in the same manner as in the measurement of the initial discharge capacity.

<Discharge Capacity Retention Rate After High-Temperature Charged Storage>

A discharge capacity retention rate (%) after the high-temperature charged storage was determined according to the following equation.

Discharge capacity retention rate (%) after high-temperature charged storage=(Discharge capacity after high-temperature charged storage)/(Initial discharge capacity)×100

[Evaluation of Gas Generation Amount After High-Temperature Charged Storage]

A gas generation amount after the high-temperature charged storage was measured by the Archimedean method. As for the gas generation amount, a relative gas generation amount was evaluated on the basis of defining the gas generation amount of Comparative Example I-1 as 100%.

In addition, the production condition and battery characteristics of each of the batteries are shown in Tables 1 to 4.

In Table 2, LiBOB (Example I-25) is lithium bis(oxalate)borate, GBL (Example I-26) is γ-butyrolactone, and EA (Example I-27) is ethyl acetate.

TABLE 1

| | Composition of electrolyte salt Composition of nonaqueous electrolytic solution (volume ratio of solvent) | Compound represented by formula (I-1) Kind | Content in nonaqueous electrolytic solution (% by mass) | Discharge capacity retention rate (%) | Gas generation amount (%) |
|---|---|---|---|---|---|
| Example I-1 | 1.15M LiPF$_6$ EC/DMC/MEC (30/40/30) | (structure A) | 1 | 80 | 55 |
| Example I-2 | 1.15M LiPF$_6$ EC/MEC (30/70) | | 1 | 77 | 58 |
| Example I-3 | 1.15M LiPF$_6$ EC/VC/DMC/MEC (29/1/40/30) | | 0.05 | 72 | 62 |
| Example I-4 | 1.15M LiPF$_6$ EC/VC/DMC/MEC (29/1/40/30) | | 0.1 | 76 | 58 |
| Example I-5 | 1.15M LiPF$_6$ EC/VC/DMC/MEC (29/1/40/30) | | 0.5 | 80 | 55 |
| Example I-6 | 1.15M LiPF$_6$ EC/VC/DMC/MEC (29/1/40/30) | | 1 | 82 | 52 |
| Example I-7 | 1.15M LiPF$_6$ EC/VC/DMC/MEC (29/1/40/30) | | 3 | 76 | 57 |
| Example I-8 | 1.15M LiPF$_6$ EC/VC/DMC/MEC (29/1/40/30) | | 5 | 72 | 63 |
| Example I-9 | 1.15M LiPF$_6$ EC/VC/DMC/MEC (29/1/40/30) | | 10 | 70 | 65 |
| Example I-10 | 1.15M LiPF$_6$ EC/VC/DMC/MEC (29/1/40/30) | (structure B) | 20 | 68 | 70 |
| Example I-11 | 1.15M LiPF$_6$ EC/VC/DMC/MEC (29/1/40/30) | | 30 | 30 | 75 |

TABLE 2

| | Composition of electrolyte salt Composition of nonaqueous electrolytic solution (volume ratio of solvent) | Compound represented by formula (I-1) | | Discharge capacity retention rate (%) | Gas generation amount (%) |
|---|---|---|---|---|---|
| | | Kind | Content in nonaqueous electrolytic solution (% by mass) | | |
| Example I-12 | 1.15M LiPF$_6$ EC/VC/DMC/MEC (29/1/40/30) | 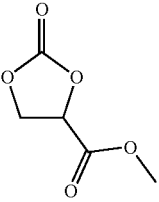 | 1 | 77 | 56 |
| Example I-13 | 1.15M LiPF$_6$ EC/VC/DMC/MEC (29/1/40/30) | 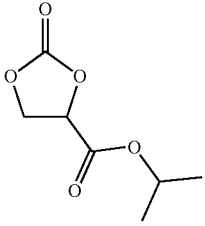 | 1 | 76 | 58 |
| Example I-14 | 1.15M LiPF$_6$ EC/VC/DMC/MEC (29/1/40/30) | 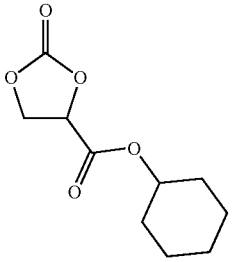 [SMILES: O=C1OCC(C(=O)OC2CCCCC2)O1] | 1 | 75 | 59 |
| Example I-15 | 1.15M LiPF$_6$ EC/VC/DMC/MEC (29/1/40/30) | 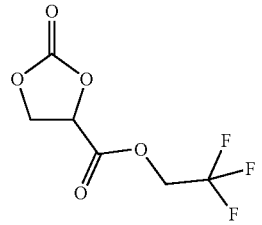 [SMILES: O=C1OCC(C(=O)OCC(F)(F)F)O1] | 1 | 78 | 54 |
| Example I-16 | 1.15M LiPF$_6$ EC/VC/DMC/MEC (29/1/40/30) | 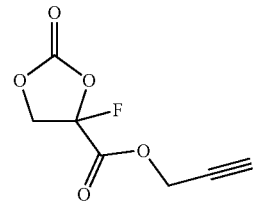 | 1 | 78 | 55 |
| Example I-17 | 1.15M LiPF$_6$ EC/VC/DMC/MEC (29/1/40/30) | 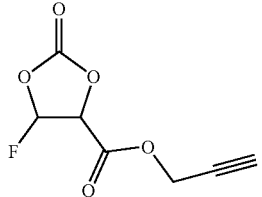 | 1 | 80 | 53 |

TABLE 2-continued

| | Composition of electrolyte salt Composition of nonaqueous electrolytic solution (volume ratio of solvent) | Compound represented by formula (I-1) | | Discharge capacity retention rate (%) | Gas generation amount (%) |
|---|---|---|---|---|---|
| | | Kind | Content in nonaqueous electrolytic solution (% by mass) | | |
| Example I-18 | 1.15M LiPF$_6$ EC/VC/DMC/MEC (29/1/40/30) | 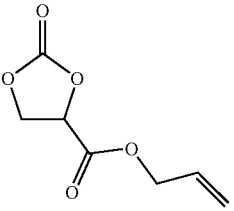 | 1 | 80 | 54 |
| Example I-19 | 1.15M LiPF$_6$ EC/VC/DMC/MEC (29/1/40/30) | 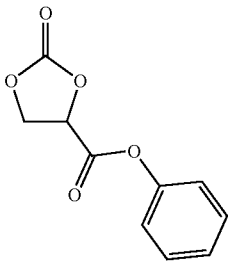 [SMILES: O=C1OCC(C(=O)Oc2ccccc2)O1] | 1 | 73 | 57 |
| Example I-20 | 1.15M LiPF$_6$ EC/VC/DMC/MEC (29/1/40/30) | 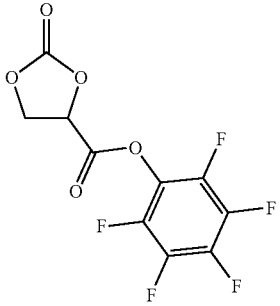 [SMILES: O=C1OCC(C(=O)Oc2c(F)c(F)c(F)c(F)c2F)O1] | 1 | 79 | 56 |
| Example I-21 | 1.15M LiPF$_6$ EC/VC/DMC/MEC (29/1/40/30) | 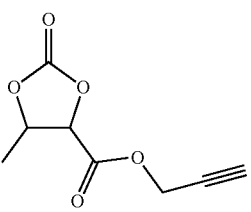 | 1 | 81 | 53 |
| Example I-22 | 1.15M LiPE$_6$ EC/VC/DMC/MEC (29/1/40/30) | 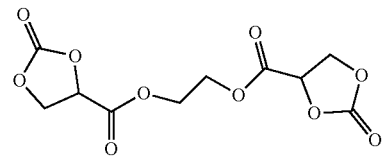 [SMILES: O=C1OCC(C(=O)OCCOC(=O)C2COC(=O)O2)O1] | 1 | 74 | 55 |
| Example I-23 | 1.15M LiPF$_6$ EC/VC/DMC/MEC (29/1/40/30) | 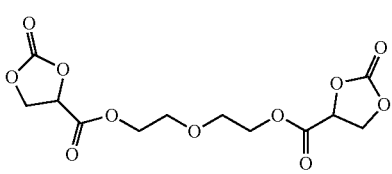 [SMILES: O=C1OCC(C(=O)OCCOCCOC(=O)C2COC(=O)O2)O1] | 1 | 73 | 53 |

TABLE 2-continued

| | Composition of electrolyte salt Composition of nonaqueous electrolytic solution (volume ratio of solvent) | Compound represented by formula (I-1) Kind | Content in nonaqueous electrolytic solution (% by mass) | Discharge capacity retention rate (%) | Gas generation amount (%) |
|---|---|---|---|---|---|
| Example I-24 | 1.15M LiPF$_6$ EC/VC/DMC/MEC (29/1/40/30) | (structure) | 1 | 80 | 54 |
| Example I-25 | 1.15M LiPF$_6$ + 0.05M LiBOB EC/FEC/VC/DMC/MEC (19/10/1/40/30) | (structure) | 1 | 84 | 52 |
| Example I-26 | 1.15M LiPF$_6$ + 0.05M LiPO$_2$F$_2$ EC/VC/DMC/MEC/GBL (29/1/37/30/3) | (structure) | 1 | 82 | 51 |
| Example I-27 | 1.1M LiPF$_6$ + 0.05M LES EC/VC/DMC/MEC/EA (29/1/35/30/5) | (structure) | 1 | 85 | 51 |

TABLE 3

| | Composition of electrolyte salt Composition of nonaqueous electrolytic solution (volume ratio of solvent) | Compound represented by formula (I-1) Kind | Content in nonaqueous electrolytic solution (% by mass) | Discharge capacity retention rate (%) | Gas generation amount (%) |
|---|---|---|---|---|---|
| Example I-28 | 1.15M LiPF$_6$ EC/VC/DMC/MEC (29/1/40/30) | (structure) | 0.1 | 70 | 65 |
| Example I-29 | 1.15M LiPF$_6$ EC/VC/DMC/MEC (29/1/40/30) | | 0.5 | 74 | 62 |
| Example I-30 | 1.15M LiPF$_6$ EC/VC/DMC/MEC (29/1/40/30) | | 1 | 76 | 59 |
| Example I-31 | 1.15M LiPF$_6$ EC/VC/DMC/MEC (29/1/40/30) | | 3 | 71 | 64 |
| Example I-32 | 1.15M LiPF$_6$ EC/VC/DMC/MEC (29/1/40/30) | | 5 | 67 | 68 |
| Example I-33 | 1.15M LiPF$_6$ EC/VC/DMC/MEC (29/1/40/30) | | 10 | 65 | 70 |

TABLE 3-continued

| | Composition of electrolyte salt Composition of nonaqueous electrolytic solution (volume ratio of solvent) | Compound represented by formula (I-1) | | Discharge capacity retention rate (%) | Gas generation amount (%) |
|---|---|---|---|---|---|
| | | Kind | Content in nonaqueous electrolytic solution (% by mass) | | |
| Example I-34 | 1.15M LiPF$_6$ EC/VC/DMC/MEC (29/1/40/30) | | 20 | 66 | 73 |
| Example I-35 | 1.15M LiPF$_6$ EC/VC/DMC/MEC (29/1/40/30) | | 30 | 64 | 79 |
| Example I-36 | 1.15M LiPF$_6$ EC/VC/DMC/MEC (29/1/40/30) | 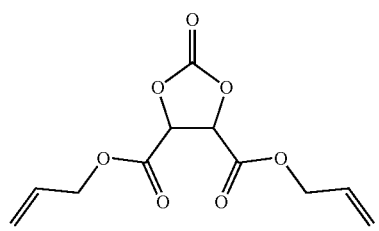 [SMILES: C=CCOC(=O)C1OC(=O)OC1C(=O)OCC=C] | 1 | 77 | 54 |
| Example I-37 | 1.15M LiPF$_6$ EC/VC/DMC/MEC (29/1/40/30) | 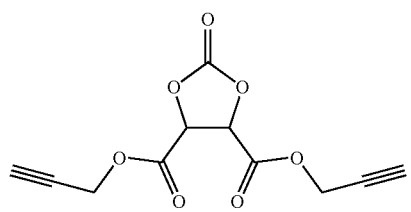 [SMILES: C#CCOC(=O)C1OC(=O)OC1C(=O)OCC#C] | 1 | 81 | 54 |
| Comparative Example I-1 | 1.15M LiPF$_6$ EC/VC/DMC/MEC (29/1/40/30) | None | — | 56 | 100 |
| Comparative Example I-2 | 1.15M LiPF$_6$ EC/VC/DMC/MEC (29/1/40/30) | 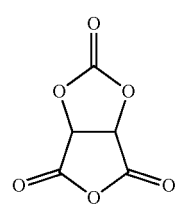 [SMILES: O=C1OC2C(=O)OC(=O)C2O1] | 1 | 55 | 101 |
| Comparative Example I-3 | 1.15M LiPF$_6$ EC/VC/DMC/MEC (29/1/40/30) | 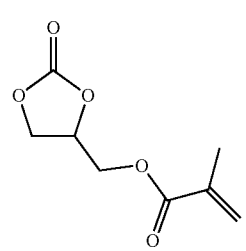 | 1 | 61 | 98 |

TABLE 4

| | Composition of electrolyte salt Composition of nonaqueous electrolytic solution (volume ratio of solvent) | Compound represented by formula (I-1) | | Group of other additive | Other additive (content in nonaqueous electrolytic solution (% by mass)) | Discharge capacity retention rate (%) | Gas generation amount (%) |
|---|---|---|---|---|---|---|---|
| | | Kind | Content in nonaqueous electrolytic solution (% by mass) | | | | |
| Example I-38 | 1.15M LiPF$_6$ EC/VC/DMC/MEC (29/1/40/30) | 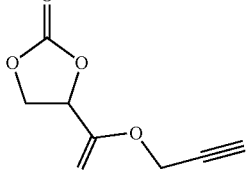 | 1 | A | Adiponitrile (1) | 79 | 45 |
| Example I-39 | | | | B | Cyclohexylbenzene (2) + o-terphenyl (1) | 85 | 54 |
| Example I-40 | | | | C | 1,6-Hexamethylene diisocyanate (1) | 80 | 46 |
| Example I-41 | | | | D | 2-Butyne-1,4-diyl dimethanesulfonate (1) | 87 | 52 |
| Example I-42 | | | | E | 5,5-Dimethyl-1,2-oxathiolane-4-one 2,2-dioxide (0.5) | 81 | 49 |
| Example I-43 | | | | F | 1,3-Dioxane (1) | 82 | 44 |
| Example I-44 | | | | G | Tris(2,2,2-trifluoroethyl) phosphate (1.5) | 81 | 46 |
| Example I-45 | | | | H | Succinic anhydride (1) | 86 | 54 |
| Example I-46 | | | | I | Ethoxypentafluoro-cyclotriphosphazene (1) | 83 | 50 |

Examples I-47 and Comparative Example I-4

A positive electrode sheet was produced by using LiNi$_{1/2}$Mn$_{3/2}$O$_4$ (positive electrode active material) in place of the positive electrode active material used in Example I-1 and Comparative Example I-1. 94% by mass of LiNi$_{1/2}$Mn$_{3/2}$O$_4$ coated with amorphous carbon and 3% by mass of acetylene black (electroconductive agent) were mixed and then added to and mixed with a solution which had been prepared by dissolving 3% by mass of polyvinylidene fluoride (binder) in 1-methyl-2-pyrrolidone in advance, thereby preparing a positive electrode mixture paste. A laminate-type battery was produced and subjected to battery evaluation in the same manners as in Example I-1 and Comparative Example I-1, except that this positive electrode mixture paste was applied onto one surface of an aluminum foil (collector), dried, and treated under pressure, followed by cutting into a predetermined size, thereby producing a positive electrode sheet; and that in evaluating the battery, the final charging voltage and the final discharging voltage were set to 4.9 V and 2.7 V, respectively. The results are shown in Table 5.

TABLE 5

| | Composition of electrolyte salt Composition of nonaqueous electrolytic solution (volume ratio of solvent) | Compound represented by formula (I-1) | | Discharge capacity retention rate (%) | Gas generation amount (%) |
|---|---|---|---|---|---|
| | | Kind | Content in nonaqueous electrolytic solution (% by mass) | | |
| Example I-47 | 1.15M LiPF$_6$ EC/FEC/MEC/DEC (20/10/45/25) | 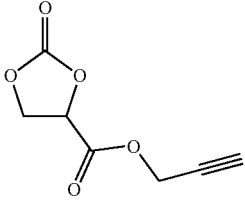 | 1 | 77 | 62 |
| Comparative Example I-4 | | None | — | 49 | 100 |

Example I-48 and Comparative Example I-5

A negative electrode sheet was produced by using lithium titanate $Li_4Ti_5O_{12}$ (negative electrode active material) in place of the negative electrode active material used in Example I-1 and Comparative Example I-1. 80% by mass of lithium titanate $Li_4Ti_5O_{12}$ and 15% by mass of acetylene black (electroconductive agent) were mixed and then added to and mixed with a solution which had been prepared by dissolving 5% by mass of polyvinylidene fluoride (binder) in 1-methyl-2-pyrrolidone in advance, thereby preparing a negative electrode mixture paste. A laminate-type battery was produced and subjected to battery evaluation in the same manners as in Example I-1 and Comparative Example I-1, except that this negative electrode mixture paste was applied onto one surface of a copper foil (collector), dried, and treated under pressure, followed by cutting into a predetermined size, thereby producing a negative electrode sheet; that in evaluating the battery, the final charging voltage and the final discharging voltage were set to 2.8 V and 1.2 V, respectively; and that the composition of the nonaqueous electrolyte was changed to a predetermined composition. The results are shown in Table 6.

In consequence, it is evident that the effects of the present invention according to Embodiment 1 are not an effect relying upon a specified positive electrode or negative electrode.

Furthermore, the nonaqueous electrolytic solution containing the compound represented by the general formula (I-1) of the present invention also has an effect for improving the discharging properties in the case of using a lithium primary battery at a high voltage.

Examples II-1 to II-25 and Comparative Examples II-1 to II-4

[Production of Lithium Ion Secondary Battery]

94% by mass of $LiNi_{1/3}Mn_{1/3}Co_{1/3}O_2$ and 3% by mass of acetylene black (electroconductive agent) were mixed and then added to and mixed with a solution which had been prepared by dissolving 3% by mass of polyvinylidene fluoride (binder) in 1-methyl-2-pyrrolidone in advance, thereby preparing a positive electrode mixture paste. This positive electrode mixture paste was applied onto one surface of an aluminum foil (collector), dried, and treated under pressure, followed by cutting into a predetermined size, thereby

TABLE 6

| | | Compound represented by formula (I-1) | | | |
|---|---|---|---|---|---|
| | Composition of electrolyte salt Composition of nonaqueous electrolytic solution (volume ratio of solvent) | Kind | Content in nonaqueous electrolytic solution (% by mass) | Discharge capacity retention rate (%) | Gas generation amount (%) |
| Example I-48 | 1.15M $LiPF_6$ PC/DEC (30/70) | 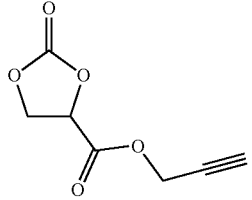 | 1 | 89 | 49 |
| Comparative Example I-5 | | None | — | 79 | 100 |

All of the lithium secondary batteries of Examples I-1 to I-46 as described above are improved in the storage characteristics at a high temperature and at a high voltage and inhibited in the gas generation amount, as compared with the lithium secondary batteries of Comparative Example I-1 which is in the case of not containing the compound represented by the general formula (I-1) and Comparative Examples I-2 and I-3 which are in the case of adding the compounds described in PTLs 1 and 2, respectively.

In the light of the above, it has become clear that the effects brought in the case of using the energy storage device of the present invention at a high voltage are peculiar effects brought in the case where the nonaqueous electrolytic solution contains the compound represented by the general formula (I-1).

In addition, from the comparison of Example I-47 with Comparative Example I-4 in the case of using lithium nickel manganate ($LiNi_{1/2}Mn_{3/2}O_4$) for the positive electrode and also from the comparison of Example I-48 with Comparative Example I-5 in the case of using lithium titanate ($Li_4Ti_5O_{12}$) for the negative electrode, the same effects are brought.

producing a positive electrode sheet in a belt-like form. A density of the positive electrode except for the collector was 3.6 g/cm³.

10% by mass of silicon (elemental substance), 80% by mass of artificial graphite ($d_{002}$=0.335 nm, negative electrode active material), and 5% by mass of acetylene black (electroconductive agent) were mixed and then added to and mixed with a solution which had been prepared by dissolving 5% by mass of polyvinylidene fluoride (binder) in 1-methyl-2-pyrrolidone in advance, thereby preparing a negative electrode mixture paste. This negative electrode mixture paste was applied onto one surface of a copper foil (collector), dried, and treated under pressure, followed by cutting into a predetermined size, thereby producing a negative electrode sheet. A density of the negative electrode except for the collector was 1.5 g/cm³.

The electrode sheet was analyzed by X-ray diffractometry, and a ratio [I(110)/I(004)] of the peak intensity I(110) of the (110) plane to the peak intensity I(004) of the (004) plane of the graphite crystal was 0.1.

The above-obtained positive electrode sheet, a microporous polyethylene-made film separator and the above-obtained negative electrode sheet were laminated in this order, and the nonaqueous electrolytic solution having each of compositions shown in Tables 7 and 8 was added, thereby producing a laminate-type battery.

[Discharge Capacity Retention Rate After High-Temperature Charged Storage]

<Initial Discharge Capacity>

In a thermostatic chamber at 25° C., the laminate-type battery produced by the aforementioned method was charged up to a final voltage of 4.35 V with a constant current of 1 C and under a constant voltage for 3 hours and then discharged down to a final voltage of 2.75 V with a constant current of 1 C, thereby determining an initial discharge capacity.

<High-Temperature Charged Storage Test>

Subsequently, in a thermostatic chamber at 65° C., this laminate-type battery was charged up to a final voltage of 4.35 V with a constant current of 1 C and under a constant voltage for 3 hours, and then stored for 5 days while being kept at 4.35 V. Thereafter, the battery was placed in a thermostatic chamber at 25° C., and once discharged under a constant current of 1 C to a final voltage of 2.75 V.

<Discharge Capacity After High-Temperature Charged Storage>

Further thereafter, the discharge capacity after the high-temperature charged storage was determined in the same manner as in the measurement of the initial discharge capacity.

<Discharge Capacity Retention Rate After High-Temperature Charged Storage>

A discharge capacity retention rate (%) after the high-temperature charged storage was determined according to the following equation.

Discharge capacity retention rate (%) after high-temperature charged storage=(Discharge capacity after high-temperature charged storage)/(Initial discharge capacity)×100

[Evaluation of Gas Generation Amount After High-Temperature Charged Storage]

A gas generation amount after the high-temperature charged storage was measured by the Archimedean method. As for the gas generation amount, a relative gas generation amount was evaluated on the basis of defining the gas generation amount of Comparative Example II-1 as 100%.

In addition, the production condition and battery characteristics of each of the batteries are shown in Tables 7 and 8.

In Table 7, GBL (Example II-14) is γ-butyrolactone, MPiv (Example II-15) is methyl pivalate, and MP (Example II-16) is methyl propionate.

TABLE 7

| | Composition of electrolyte salt Composition of nonaqueous electrolytic solution (volume ratio of solvent) | Compound represented by formula (I-2) Kind | Content in nonaqueous electrolytic solution (% by mass) | Discharge capacity retention rate (%) | Gas generation amount (%) |
|---|---|---|---|---|---|
| Example II-1 | 1M LiPF$_6$ EC/PC/MEC/DEC (26/4/30/40) | (cyclic sulfate) | 1 | 71 | 64 |
| Example II-2 | 1M LiPF$_6$ EC/MEC (30/70) | | 1 | 67 | 67 |
| Example II-3 | 1M LiPF$_6$ EC/PC/VC/MEC/DEC (20/9/1/30/40) | (dimethyl ester) | 0.01 | 63 | 72 |
| Example II-4 | 1M LiPF$_6$ EC/PC/VC/MEC/DEC (20/9/1/30/40) | | 0.1 | 72 | 64 |
| Example II-5 | 1M LiPF$_6$ EC/PC/VC/MEC/DEC (20/9/1/30/40) | | 1 | 78 | 59 |
| Example II-6 | 1M LiPF$_6$ EC/PC/VC/MEC/DEC (20/9/1/30/40) | | 4 | 73 | 57 |
| Example II-7 | 1M LiPF$_6$ EC/PC/VC/MEC/DEC (20/9/1/30/40) | (cyclic sulfate methyl ester) | 1 | 75 | 61 |
| Example II-8 | 1M LiPF$_6$ EC/PC/VC/MEC/DEC (20/9/1/30/40) | (cyclic sulfate propargyl ester) | 1 | 81 | 60 |

TABLE 7-continued

| | Composition of electrolyte salt Composition of nonaqueous electrolytic solution (volume ratio of solvent) | Compound represented by formula (I-2) | | | |
|---|---|---|---|---|---|
| | | Kind | Content in nonaqueous electrolytic solution (% by mass) | Discharge capacity retention rate (%) | Gas generation amount (%) |
| Example II-9 | 1M LiPF$_6$ EC/PC/VC/MEC/DEC (20/9/1/30/40) | 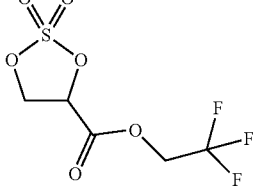 | 1 | 77 | 59 |
| Example II-10 | 1M LiPF$_6$ EC/PC/VC/MEC/DEC (20/9/1/30/40) | 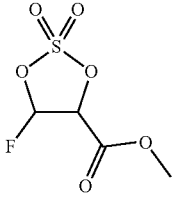 | 1 | 79 | 58 |
| Example II-11 | 1M LiPF$_6$ EC/PC/VC/MEC/DEC (20/9/1/30/40) | 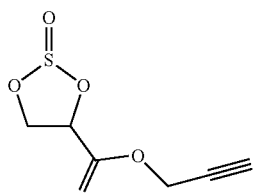 | 1 | 79 | 66 |
| Example II-12 | 1M LiPF$_6$ EC/PC/VC/MEC/DEC (20/9/1/30/40) | 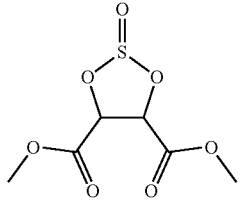 | 1 | 76 | 63 |
| Example II-13 | 1M LiPF$_6$ + 0.05M LiFOP EC/PC/FEC/VC/DEC/MEC (16/3/10/1/45/25) | 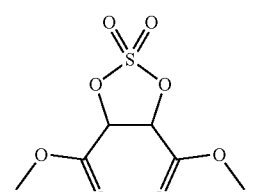 | 1 | 81 | 58 |
| Example II-14 | 1M LiPF$_6$ + 0.05M LiPO$_2$F$_2$ EC/PC/VC/DEC/MEC/GBL (26/3/1/42/25/3) | 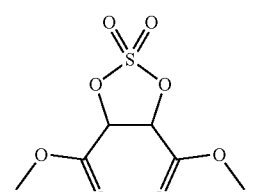 | 1 | 80 | 55 |
| Example II-15 | 1M LiPF$_6$ + 0.05M LES EC/PC/VC/DEC/MEC/MPiv (20/9/1/40/25/5) | 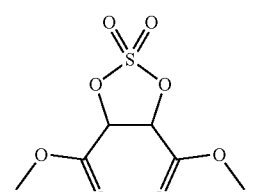 | 1 | 83 | 54 |
| Example II-16 | 0.70M LiPF$_6$ + 0.35M FSI EC/PC/VC/DMC/MEC/MP (20/9/1/40/25/5) | | 1 | 84 | 56 |

TABLE 8

| | Composition of electrolyte salt Composition of nonaqueous electrolytic solution (volume ratio of solvent) | Compound represented by formula (I-2) | | Discharge capacity retention rate (%) | Gas generation amount (%) |
|---|---|---|---|---|---|
| | | Kind | Content in nonaqueous electrolytic solution (% by mass) | | |
| Example II-17 | 1M LiPF$_6$ EC/PC/MEC/DMC (20/10/30/40) | 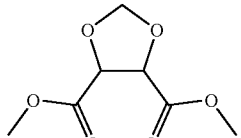 | 1 | 68 | 68 |
| Example II-18 | 1M LiPF$_6$ EC/MEC (30/70) | | 1 | 65 | 70 |
| Example II-19 | 1M LiPF$_6$ EC/PC/VC/MEC/DEC (20/9/1/30/40) | | 0.01 | 61 | 73 |
| Example II-20 | 1M LiPF$_6$ EC/PC/VC/MEC/DEC (20/9/1/30/40) | | 0.1 | 69 | 70 |
| Example II-21 | 1M LiPF$_6$ EC/PC/VC/MEC/DEC (20/9/1/30/40) | | 1 | 74 | 65 |
| Example II-22 | 1M LiPF$_6$ EC/PC/VC/MEC/DEC (20/9/1/30/40) | | 4 | 71 | 62 |
| Example II-23 | 1M LiPF$_6$ EC/PC/VC/MEC/DEC (20/9/1/30/40) | 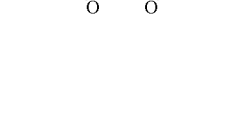 | 1 | 73 | 68 |
| Example II-24 | 1M LiPF$_6$ EC/PC/VC/MEC/DEC (20/9/1/30/40) |  | 1 | 72 | 70 |
| Example II-25 | 1M LiPF$_6$ EC/PC/VC/MEC/DEC (20/9/1/30/40) | 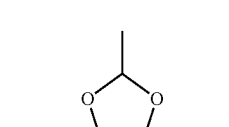 | 1 | 70 | 67 |
| Comparative Example II-1 | 1M LiPF$_6$ EC/PC/VC/MEC/DEC (20/9/1/30/40) | None | 1 | 51 | 100 |
| Comparative Example II-2 | 1M LiPF$_6$ EC/PC/VC/MEC/DEC (20/9/1/30/40) | 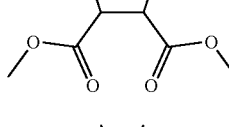 | 1 | 59 | 88 |
| Comparative Example II-3 | 1M LiPF$_6$ EC/PC/VC/MEC/DEC (20/9/1/30/40) | 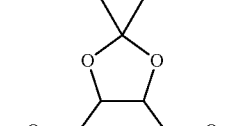 | 1 | 54 | 92 |
| Comparative Example II-4 | 1M LiPF$_6$ EC/PC/VC/MEC/DEC (20/9/1/30/40) | 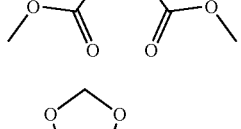 | 1 | 51 | 83 |

Examples II-26 and II-27 and Comparative Example II-5

A positive electrode sheet was produced by using $LiNi_{1/2}Mn_{3/2}O_4$ (positive electrode active material) in place of the positive electrode active material used in Example II-1 and Comparative Example II-1. 94% by mass of $LiNi_{1/2}Mn_{3/2}O_4$ coated with amorphous carbon and 3% by mass of acetylene black (electroconductive agent) were mixed and then added to and mixed with a solution which had been prepared by dissolving 3% by mass of polyvinylidene fluoride (binder) in 1-methyl-2-pyrrolidone in advance, thereby preparing a positive electrode mixture paste. A laminate-type battery was produced and subjected to battery evaluation in the same manners as in Example II-1 and Comparative Example II-1, except that this positive electrode mixture paste was applied onto one surface of an aluminum foil (collector), dried, and treated under pressure, followed by cutting into a predetermined size, thereby producing a positive electrode sheet; and that in evaluating the battery, the final charging voltage and the final discharging voltage were set to 4.9 V and 2.7 V, respectively. The results are shown in Table 9.

In Table 9, FEC is 4-fluoro-1,3-dioxolan-2-one, and MTFEC is methyl (2,2,2-trifluoroethyl)carbonate.

Examples II-28 and II-29 and Comparative Example II-6

A negative electrode sheet was produced by using lithium titanate $Li_4Ti_5O_{12}$ (negative electrode active material) in place of the negative electrode active material used in Example II-1 and Comparative Example II-1. 80% by mass of lithium titanate $Li_4Ti_5O_{12}$ and 15% by mass of acetylene black (electroconductive agent) were mixed and then added to and mixed with a solution which had been prepared by dissolving 5% by mass of polyvinylidene fluoride (binder) in 1-methyl-2-pyrrolidone in advance, thereby preparing a negative electrode mixture paste. A laminate-type battery was produced and subjected to battery evaluation in the same manners as in Example II-1 and Comparative Example II-1, except that this negative electrode mixture paste was applied onto one surface of a copper foil (collector), dried, and treated under pressure, followed by cutting into a predetermined size, thereby producing a negative electrode sheet; and that in evaluating the battery, the final charging voltage and the final discharging voltage were set to 2.8 V and 1.2 V, respectively; and that the composition of the nonaqueous electrolyte was changed to a predetermined composition. The results are shown in Table 10.

TABLE 9

|  | Composition of electrolyte salt Composition of nonaqueous electrolytic solution (volume ratio of solvent) | Compound represented by formula (I-2) | | Discharge capacity retention rate (%) | Gas generation amount (%) |
|---|---|---|---|---|---|
|  |  | Kind | Content in nonaqueous electrolytic solution (% by mass) |  |  |
| Example II-26 | 1M $LiPF_6$ FEC/MTFEC (30/70) | 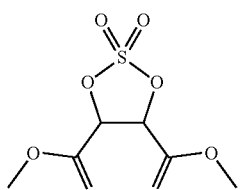 | 1 | 71 | 75 |
| Example II-27 |  | 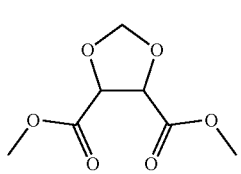 | 1 | 64 | 78 |
| Comparative Example II-5 |  | None | — | 45 | 100 |

TABLE 10

| | | Compound represented by formula (I-2) | | | |
|---|---|---|---|---|---|
| | Composition of electrolyte salt Composition of nonaqueous electrolytic solution (volume ratio of solvent) | Kind | Content in nonaqueous electrolytic solution (% by mass) | Discharge capacity retention rate (%) | Gas generation amount (%) |
| Example II-28 | 1M LiPF$_6$ PC/DEC (30/70) | 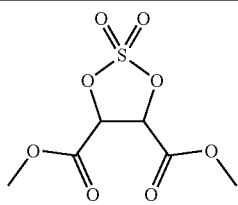 | 1 | 87 | 64 |
| Example II-29 | | 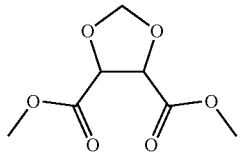 | 1 | 82 | 68 |
| Comparative Example II-6 | | None | — | 74 | 100 |

All of the lithium secondary batteries of Examples II-1 to II-25 as described above are improved in the storage characteristics at a high temperature and at a high voltage and inhibited in the gas generation amount, as compared with the lithium secondary batteries of Comparative Example II-1 which is in the case of not containing the compound represented by the general formula (I-2) and Comparative Example II-2 which is in the case of adding the compound described in PTL 4, respectively, the lithium secondary battery of Comparative Example II-3 which is in the case of adding the compound described in PTL 5, and the lithium secondary battery of Comparative Example II-4 which is in the case of adding the compound described in PTL 6.

In the light of the above, it has become clear that the effects brought in the case of using the energy storage device of the present invention at a high voltage are peculiar effects brought in the case where the nonaqueous electrolytic solution contains the compound represented by the general formula (I-2).

In addition, from the comparison of Examples II-26 and II-27 with Comparative Example II-5 in the case of using lithium nickel manganate (LiNi$_{1/2}$Mn$_{3/2}$O$_4$) for the positive electrode and also from the comparison of Examples II-28 and II-29 with Comparative Example II-6 in the case of using lithium titanate (Li$_4$Ti$_5$O$_{12}$) for the negative electrode, the same effects are brought.

In consequence, it is evident that the effects of the present invention according to Embodiment 2 are not an effect relying upon a specified positive electrode or negative electrode.

Furthermore, the nonaqueous electrolytic solution containing the compound represented by the general formula (I-2) of the present invention also has an effect for improving the discharging properties in the case of using a lithium primary battery at a high voltage.

Synthesis Example III-1

Synthesis of Dimethyl 1,5,2,4-Dioxadithiepane-6,7-dicarboxylate 2,2,4,4-Tetraoxide (Synthetic Compound 3)

4.19 g (23.5 mmol) of dimethyl tartrate and 5.00 g (23.5 mmol) of methanedisulfonyl dichloride were dissolved in 140 mL of ethyl acetate and then cooled to 15° C. To this solution, 4.93 g (48.7 mmol) of triethylamine was added dropwise at 13 to 17° C. over 10 minutes, followed by stirring at room temperature for 3 hours. The produced salt was filtered off, the solvent was concentrated under reduced pressure, and the resulting residue was purified by means of silica gel column chromatography (elution with ethyl acetate/hexane=⅕), thereby obtaining 1.72 g (yield: 23%) of dimethyl 1,5,2,4-dioxadithiepane-6,7-dicarboxylate 2,2,4,4-tetraoxide as a white solid.

The obtained dimethyl 1,5,2,4-dioxadithiepane-6,7-dicarboxylate 2,2,4,4-tetraoxide was subjected to $^1$H-NMR and melting point measurement. The results are shown below.

$^1$H-NMR (400 MHz, CDCl$_3$): δ=5.73 (s, 2H), δ=5.04 (s, 2H), δ=3.90 (s, 6H)

Examples III-1 to III-15 and Comparative Examples III-1 to III-2

[Production of Lithium Ion Secondary Battery]

94% by mass of LiCoO$_2$ and 3% by mass of acetylene black (electroconductive agent) were mixed and then added to and mixed with a solution which had been prepared by dissolving 3% by mass of polyvinylidene fluoride (binder) in 1-methyl-2-pyrrolidone in advance, thereby preparing a positive electrode mixture paste. This positive electrode mixture paste was applied onto one surface of an aluminum foil (collector), dried, and treated under pressure, followed by cutting into a predetermined size, thereby producing a positive electrode sheet in a belt-like form. A density of the positive electrode except for the collector was 3.6 g/cm$^3$.

10% by mass of silicon (elemental substance), 80% by mass of artificial graphite ($d_{002}$=0.335 nm, negative electrode active material), and 5% by mass of acetylene black (electroconductive agent) were mixed and then added to and mixed with a solution which had been prepared by dissolving 5% by mass of polyvinylidene fluoride (binder) in 1-methyl-2-pyrrolidone in advance, thereby preparing a negative electrode mixture paste. This negative electrode mixture paste was applied onto one surface of a copper foil (collector), dried, and treated under pressure, followed by cutting into a predetermined size, thereby producing a negative electrode sheet. A density of the negative electrode except for the collector was 1.5 g/cm³.

The electrode sheet was analyzed by X-ray diffractometry, and a ratio [I(110)/I(004)] of the peak intensity I(110) of the (110) plane to the peak intensity I(004) of the (004) plane of the graphite crystal was 0.1.

The above-obtained positive electrode sheet, a microporous polyethylene-made film separator and the above-obtained negative electrode sheet were laminated in this order, and the nonaqueous electrolytic solution having each of compositions shown in Tables 11 and 12 was added, thereby producing a laminate-type battery.

[Discharge Capacity Retention Rate After High-Temperature Charged Storage]
<Initial Discharge Capacity>

In a thermostatic chamber at 25° C., the laminate-type battery produced by the aforementioned method was charged up to a final voltage of 4.35 V with a constant current of 1 C and under a constant voltage for 3 hours and then discharged down to a final voltage of 2.75 V with a constant current of 1 C, thereby determining an initial discharge capacity.

<High-Temperature Charged Storage Test>

Subsequently, in a thermostatic chamber at 55° C., this laminate-type battery was charged up to a final voltage of 4.35 V with a constant current of 1 C and under a constant voltage for 3 hours, and then stored for 10 days while being kept at 4.35 V. Thereafter, the battery was placed in a thermostatic chamber at 25° C., and once discharged under a constant current of 1 C to a final voltage of 2.75 V.

<Discharge Capacity After High-Temperature Charged Storage>

Further thereafter, the discharge capacity after the high-temperature charged storage was determined in the same manner as in the measurement of the initial discharge capacity.

<Discharge Capacity Retention Rate After High-Temperature Charged Storage>

A discharge capacity retention rate (%) after the high-temperature charged storage was determined according to the following equation.

Discharge capacity retention rate (%) after high-temperature charged storage=(Discharge capacity after high-temperature charged storage)/(Initial discharge capacity)×100

[Evaluation of Gas Generation Amount After High-Temperature Charged Storage]

A gas generation amount after the high-temperature charged storage was measured by the Archimedean method. As for the gas generation amount, a relative gas generation amount was evaluated on the basis of defining the gas generation amount of Comparative Example III-1 as 100%.

In addition, the production condition and battery characteristics of each of the batteries are shown in Tables 11 to 12.

TABLE 11

| | | Compound represented by formula (I-3) | | | |
|---|---|---|---|---|---|
| | Composition of electrolyte salt Composition of nonaqueous electrolytic solution (volume ratio of solvent) | Kind | Content in nonaqueous electrolytic solution (% by mass) | Discharge capacity retention rate (%) | Gas generation amount (%) |
| Example III-1 | 1.2M LiPF$_6$ EC/DMC/MEC (30/45/25) | 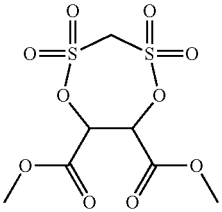 | 1 | 73 | 62 |
| Example III-2 | 1.2M LiPF$_6$ EC/MEC (30/70) | | 1 | 71 | 64 |
| Example III-3 | 1.2M LiPF$_6$ EC/VC/DMC/MEC (29/1/45/25) | | 0.005 | 66 | 65 |
| Example III-4 | 1.2M LiPF$_6$ EC/VC/DMC/MEC (29/1/45/25) | | 0.1 | 75 | 56 |
| Example III-5 | 1.2M LiPF$_6$ EC/VC/DMC/MEC (29/1/45/25) | | 1 | 81 | 51 |
| Example III-6 | 1.2M LiPF$_6$ EC/VC/DMC/MEC (29/1/45/25) | | 3 | 75 | 55 |
| Example III-7 | 1.2M LiPF$_6$ EC/VC/DMC/MEC (29/1/45/25) | | 6 | 69 | 60 |

TABLE 11-continued

| | Composition of electrolyte salt Composition of nonaqueous electrolytic solution (volume ratio of solvent) | Compound represented by formula (I-3) | | | |
|---|---|---|---|---|---|
| | | Kind | Content in nonaqueous electrolytic solution (% by mass) | Discharge capacity retention rate (%) | Gas generation amount (%) |
| Example III-8 | 1.2M LiPF$_6$ EC/VC/DMC/MEC (29/1/45/25) | 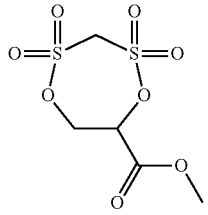 | 1 | 77 | 53 |
| Example III-9 | 1.2M LiPF$_6$ EC/VC/DMC/MEC (29/1/45/25) | 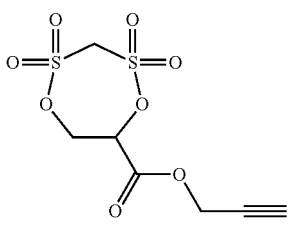 [SMILES: C#CCOC(=O)C1COS(=O)(=O)CS(=O)(=O)O1] | 1 | 83 | 53 |
| Example III-10 | 1.2M LiPF$_6$ EC/VC/DMC/MEC (29/1/45/25) | 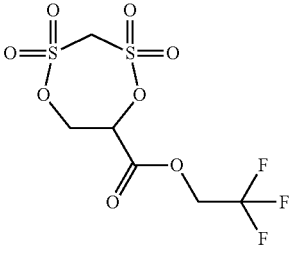 [SMILES: O=C(OCC(F)(F)F)C1COS(=O)(=O)CS(=O)(=O)O1] | 1 | 80 | 51 |
| Example III-11 | 1.2M LiPF$_6$ EC/VC/DMC/MEC (29/1/45/25) | 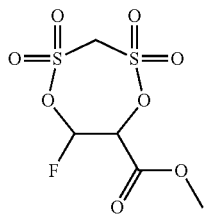 [SMILES: COC(=O)C1OS(=O)(=O)CS(=O)(=O)OC1F] | 1 | 81 | 53 |

| | Composition of electrolyte salt Composition of nonaqueous electrolytic solution (volume ratio of solvent) | Compound represented by formula (I-3) | | | |
|---|---|---|---|---|---|
| | | Kind | Content in nonaqueous electrolytic solution (% by mass) | Discharge capacity retention rate (%) | Gas generation amount (%) |
| Example III-8 | 1.2M LiPF$_6$ EC/VC/DMC/MEC (29/1/45/25) | 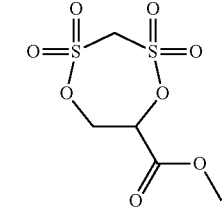 | 1 | 77 | 53 |

-continued

| | Composition of electrolyte salt Composition of nonaqueous electrolytic solution (volume ratio of solvent) | Compound represented by formula (I-3) Kind | Content in nonaqueous electrolytic solution (% by mass) | Discharge capacity retention rate (%) | Gas generation amount (%) |
|---|---|---|---|---|---|
| Example III-9 | 1.2M LiPF$_6$ EC/VC/DMC/MEC (29/1/45/25) | (structure) | 1 | 83 | 53 |
| Example III-10 | 1.2M LiPF$_6$ EC/VC/DMC/MEC (29/1/45/25) | (structure) | 1 | 80 | 51 |
| Example III-11 | 1.2M LiPF$_6$ EC/VC/DMC/MEC (29/1/45/25) | (structure) | 1 | 81 | 53 |
| Example III-12 | 1.2M LiPF$_6$ + 0.05M LiFOP EC/FEC/VC/DMC/MEC (19/10/1/45/25) | (structure) | 1 | 83 | 53 |
| Example III-13 | 1.2M LiPF$_6$ + 0.05M LiPO$_2$F$_2$ EC/VC/DMC/MEC/GBL (29/1/42/25/3) | | 1 | 82 | 50 |
| Example III-14 | 1.2M LiPF$_6$ + 0..05M LES EC/VC/DMC/MEC/EA (29/1/40/25/5) | | 1 | 85 | 49 |
| Example III-15 | 0.7M LiPF$_6$ + 0.55M FSI EC/VC/DMC/MEC (29/1/45/25) | | 1 | 84 | 46 |
| Comparative Example III-1 | 1.2M LiPF$_6$ EC/VC/DMC/MEC (29/1/45/25) | None | — | 54 | 100 |
| Comparative Example III-2 | 1.2M LiPF$_6$ EC/VC/DMC/MEC (29/1/45/25) | (structure) | 1 | 60 | 85 |

Example III-16 and Comparative Example III-3

A positive electrode sheet was produced by using LiNi$_{1/2}$Mn$_{3/2}$O$_4$ (positive electrode active material) in place of the positive electrode active material used in Example III-1 and Comparative Example III-1. 94% by mass of LiNi$_{1/2}$Mn$_{3/2}$O$_4$ coated with amorphous carbon and 3% by mass of acetylene black (electroconductive agent) were mixed and then added to and mixed with a solution which had been prepared by dissolving 3% by mass of polyvinylidene fluoride (binder) in 1-methyl-2-pyrrolidone in advance, thereby preparing a positive electrode mixture paste. A laminate-type battery was produced and subjected to battery evaluation in the same manners as in Example III-1 and Comparative Example III-1, except that this positive electrode mixture paste was applied onto one surface of an aluminum foil (collector), dried, and treated under pressure, followed by cutting into a predetermined size, thereby producing a positive electrode sheet; and that in evaluating the battery, the final charging voltage and the final discharging voltage were set to 4.9 V and 2.7 V, respectively. The results are shown in Table 13.

TABLE 13

| | Composition of electrolyte salt Composition of nonaqueous electrolytic solution (volume ratio of solvent) | Compound represented by formula (I-3) Kind | Content in nonaqueous electrolytic solution (% by mass) | Discharge capacity retention rate (%) | Gas generation amount (%) |
|---|---|---|---|---|---|
| Example III-16 | 1.2M LiPF$_6$ EC/FEC/MEC/DEC (20/10/40/30) | 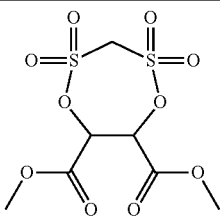 | 1 | 77 | 68 |
| Comparative Example III-3 | | None | — | 51 | 100 |

Example III-17 and Comparative Example III-4

A negative electrode sheet was produced by using lithium titanate Li$_4$Ti$_5$O$_{12}$ (negative electrode active material) in place of the negative electrode active material used in Example III-1 and Comparative Example III-1. 80% by mass of lithium titanate Li$_4$Ti$_5$O$_{12}$ and 15% by mass of acetylene black (electroconductive agent) were mixed and then added to and mixed with a solution which had been prepared by dissolving 5% by mass of polyvinylidene fluoride (binder) in 1-methyl-2-pyrrolidone in advance, thereby preparing a negative electrode mixture paste. A laminate-type battery was produced and subjected to battery evaluation in the same manners as in Example III-1 and Comparative Example III-1, except that this negative electrode mixture paste was applied onto one surface of a copper foil (collector), dried, and treated under pressure, followed by cutting into a predetermined size, thereby producing a negative electrode sheet; and that in evaluating the battery, the final charging voltage and the final discharging voltage were set to 2.8 V and 1.2 V, respectively; and that the composition of the nonaqueous electrolytic solution was changed to a predetermined composition. The results are shown in Table 14.

All of the lithium secondary batteries of Examples III-1 to III-15 as described above are improved in the storage characteristics at a high temperature and at a high voltage and inhibited in the gas generation amount, as compared with the lithium secondary batteries of Comparative Example III-1 which is in the case of not containing the compound represented by the general formula (I-3) and Comparative Example III-2 which is in the case of adding the compound described in PTL 7, respectively.

In the light of the above, it has become clear that the effects brought in the case of using the energy storage device of the present invention at a high voltage are peculiar effects brought in the case where the nonaqueous electrolytic solution contains the compound represented by the general formula (I-3).

In addition, from the comparison of Example III-16 with Comparative Example III-3 in the case of using lithium nickel manganate (LiNi$_{1/2}$Mn$_{3/2}$O$_4$) for the positive electrode and also from the comparison of Example III-17 with Comparative Example III-4 in the case of using lithium titanate (Li$_4$Ti$_5$O$_{12}$) for the negative electrode, the same effects are brought.

TABLE 14

| | Composition of electrolyte salt Composition of nonaqueous electrolytic solution (volume ratio of solvent) | Compound represented by formula (I-3) Kind | Content in nonaqueous electrolytic solution (% by mass) | Discharge capacity retention rate (%) | Gas generation amount (%) |
|---|---|---|---|---|---|
| Example III-17 | 1.15M LiPF$_6$ PC/DEC (30/70) | 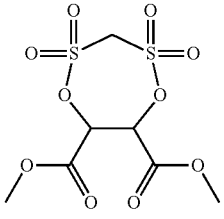 | 1 | 90 | 52 |
| Comparative Example III-4 | | None | — | 80 | 100 |

In consequence, it is evident that the effects of the present invention according to Embodiment 3 are not an effect relying upon a specified positive electrode or negative electrode.

Furthermore, the nonaqueous electrolytic solution containing the compound represented by the general formula (I-3) of the present invention also has an effect for improving the discharging properties in the case of using a lithium primary battery at a high voltage.

INDUSTRIAL APPLICABILITY

The energy storage device using the nonaqueous electrolytic solution of the present invention is useful as an energy storage device, such as a lithium secondary battery, etc., having excellent electrochemical characteristics in the case of using a battery at a high temperature and at a high voltage.

The invention claimed is:

1. A nonaqueous electrolytic solution having an electrolyte salt dissolved in a nonaqueous solvent, the nonaqueous electrolytic solution comprising from 0.001 to 10% by mass of a carboxylic acid ester compound represented by the following general formula (I):

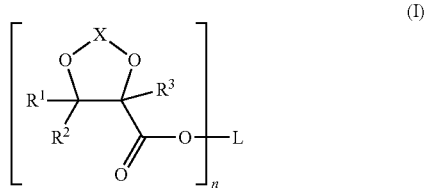

wherein:
each of $R^1$ and $R^2$ independently represents a hydrogen atom, a halogen atom, an alkyl group having 1 to 6 carbon atoms, a cycloalkyl group having 3 to 6 carbon atoms, an alkenyl group having 2 to 6 carbon atoms, an alkynyl group having 3 to 6 carbon atoms, an aralkyl group haying 7 to 13 carbon atoms, or an aryl group having 6 to 12 carbon atoms, and when $R^1$ and $R^2$ are each an alkyl group, then $R^1$ and $R^2$ may be bonded to each other to form a ring structure;
$R^3$ represents a hydrogen atom, a halogen atom, or an alkyl group having 1 to 6 carbon atoms;
n represents an integer of 1 to 3;
when n is 1, then L represents an alkyl group having 1 to 6 carbon atoms, a cycloalkyl group having 3 to 6 carbon atoms, an alkenyl group having 2 to 6 carbon atoms, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, or an aryl group having 6 to 12 carbon atoms, and when n is 2 or 3, then L represents an n-valent connecting group constituted of a carbon atom and a hydrogen atom, which may contain an ether bond, a thioether bond, or an $SO_2$ bond; and
X represents a —C(=O)— group,
wherein at least one hydrogen atom of the alkyl group having 1 to 6 carbon atoms, the cycloalkyl group having 3 to 6 carbon atoms, the alkenyl group having 2 to 6 carbon atoms, the alkynyl group having 3 to 6 carbon atoms, the alkoxyalkyl group having 2 to 6 carbon atoms, the cyanoalkyl group having 2 to 6 carbon atoms, the aralkyl group having 7 to 13 carbon atoms, or the aryl group having 6 to 12 carbon atoms as $R^1$, $R^2$, or L, may be substituted with a halogen atom.

2. The nonaqueous electrolytic solution according to claim 1, wherein in the general formula (I), the compound wherein X is a —C(=O)— group, and n is an integer of 1 to 3 is a carboxylic acid ester compound represented by the following general formula (I-1):

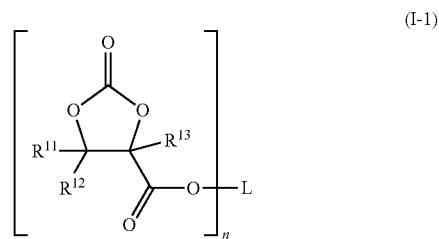

wherein:
each of $R^{11}$ and $R^{12}$ independently represents a hydrogen atom, a halogen atom, an alkyl group having 1 to 6 carbon atoms, in which at least one hydrogen atom may be substituted with a halogen atom, a cycloalkyl group having 3 to 6 carbon atoms, an alkenyl group having 2 to 6 carbon atoms, an alkynyl group having 3 to 6 carbon atoms, an aralkyl group having 7 to 13 carbon atoms, in which at least one hydrogen atom may be substituted with a halogen atom, or an aryl group having 6 to 12 carbon atoms, in which at least one hydrogen atom may be substituted with a halogen atom, and when $R^{11}$ and $R^{12}$ are each an alkyl group, then $R^{11}$ and $R^{12}$ may be bonded to each other to form a ring structure;
$R^{13}$ represents a hydrogen atom, a halogen atom, or an alkyl group having 1 to 6 carbon atoms:
n represents an integer of 1 to 3; and
when n is 1, then L represents an alkyl group having 1 to 6 carbon atoms, in which at least one hydrogen atom may be substituted with a halogen atom, a cycloalkyl group having 3 to 6 carbon atoms, in which at least one hydrogen atom may be substituted with a halogen atom, an alkenyl group having 2 to 6 carbon atoms, in which at least one hydrogen atom may be substituted with a halogen atom, an alkynyl group having 3 to 6 carbon atoms, an alkoxyalkyl group having 2 to 6 carbon atoms, a cyanoalkyl group having 2 to 6 carbon atoms, an aralkyl group having 7 to 13 carbon atoms, in which at least one hydrogen atom may be substituted with a halogen atom, or an aryl group having 6 to 12 carbon atoms, in which at least one hydrogen atom may be substituted with a halogen atom, and when n is 2 or 3, then L represents an n-valent connecting group constituted of a carbon atom and a hydrogen atom, which may contain an ether bond, a thioether bond, or an $SO_2$ bond, at least one hydrogen atom of L may be substituted with a halogen atom.

3. The nonaqueous electrolytic solution according to claim 1, wherein the nonaqueous electrolytic solution having an electrolyte salt dissolved in a nonaqueous solvent comprises the carboxylic acid ester compound represented by the general formula (I) and further comprises at least one cyclic carbonate having an unsaturated bond selected from the group consisting of a carbon-carbon double bond and a carbon-carbon triple bond, or a fluorine atom.

4. The nonaqueous electrolytic solution according to claim 1, wherein the nonaqueous electrolytic solution having an electrolyte salt dissolved in a nonaqueous solvent comprises 0.01 to 5% by mass of the carboxylic acid ester compound represented by the general formula (I).

5. The nonaqueous electrolytic solution according to claim 1, wherein the nonaqueous electrolytic solution having an electrolyte salt dissolved in a nonaqueous solvent comprises the carboxylic acid ester compound represented by the general formula (I) and further comprises $LiPF_6$ as an electrolyte salt.

6. The nonaqueous electrolytic solution according to claim 1, wherein the nonaqueous electrolytic solution having an electrolyte salt dissolved in a nonaqueous solvent comprises 0.3 to 5% by mass of the carboxylic acid ester compound represented by the general formula (I).

7. An energy storage device comprising a positive electrode, a negative electrode, and a nonaqueous electrolytic solution having an electrolyte salt dissolved in a nonaqueous solvent, the nonaqueous electrolytic solution comprising the nonaqueous electrolytic solution according to claim 1.

8. The energy storage device according to claim 7, wherein the positive electrode comprises, as a positive electrode active material, a complex metal oxide containing lithium and one or more selected from cobalt, manganese, and nickel, or a lithium-containing olivine-type phosphate.

9. The energy storage device according to claim 7, wherein the negative electrode comprises, as a negative electrode active material, one or more selected from lithium metal, a lithium alloy, a carbon material capable of absorbing and releasing lithium, tin, a tin compound, silicon, a silicon compound, and a lithium titanate compound.

* * * * *